US007867739B2

(12) United States Patent
Dicosimo et al.

(10) Patent No.: US 7,867,739 B2
(45) Date of Patent: Jan. 11, 2011

(54) PROCESS FOR ENZYMATICALLY CONVERTING GLYCOLONITRILE TO GLYCOLIC ACID

(75) Inventors: Robert Dicosimo, Chadds Ford, PA (US); Anna Panova, Hockessin, DE (US); Samuel D. Arthur, Wilmington, DE (US); Henry Keith, Hockessin, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 12/429,576

(22) Filed: Apr. 24, 2009

(65) Prior Publication Data

US 2009/0233339 A1 Sep. 17, 2009

Related U.S. Application Data

(62) Division of application No. 11/931,069, filed on Oct. 31, 2007.

(51) Int. Cl.
*C12P 7/62* (2006.01)
*C12N 9/00* (2006.01)
*C12N 9/78* (2006.01)
*C07K 14/00* (2006.01)

(52) U.S. Cl. .............. 435/135; 435/183; 435/227; 530/350

(58) Field of Classification Search ............... None
See application file for complete search history.

(56) References Cited

U.S. PATENT DOCUMENTS

| 2,175,805 | A | 10/1939 | Jacobson |
| 2,890,238 | A | 6/1959 | Sexton |
| 3,940,316 | A | 2/1976 | Commeyras et al. |
| 5,187,301 | A | 2/1993 | Cullen et al. |
| 5,223,416 | A | 6/1993 | Endo et al. |
| 5,234,826 | A | 8/1993 | Yamagami et al. |
| 5,296,373 | A | 3/1994 | Endo et al. |
| 5,326,702 | A | 7/1994 | Endo et al. |
| 5,508,181 | A | 4/1996 | Hashimoto |
| 5,605,793 | A | 2/1997 | Stemmer |
| 5,756,306 | A | 5/1998 | Yamaguchi et al. |
| 5,811,238 | A | 9/1998 | Stemmer et al. |
| 5,814,508 | A | 9/1998 | DiCosimo et al. |
| 5,830,721 | A | 11/1998 | Stemmer et al. |
| 5,837,458 | A | 11/1998 | Minshull et al. |
| 6,037,155 | A | 3/2000 | Kobayashi et al. |
| 6,291,708 | B1 | 9/2001 | Cockrem |
| 6,383,786 | B1 | 5/2002 | Chauhan et al. |
| 6,416,980 | B1 | 7/2002 | Chauhan et al. |
| 6,870,038 | B2 | 3/2005 | Dicosimo et al. |
| 7,148,051 | B2 | 12/2006 | Payne et al. |
| 7,198,927 | B2 | 4/2007 | DiCosimo et al. |
| 7,473,545 | B2 | 1/2009 | DiCosimo et al. |
| 7,638,617 | B2 | 12/2009 | DiCosimo et al. |

| 2004/0138409 | A1 | 7/2004 | Hayashi et al. |
| 2004/0210087 | A1 | 10/2004 | Meng et al. |
| 2006/0160196 | A1 | 7/2006 | Foo |
| 2006/0247467 | A1 | 11/2006 | DiCosimo |

FOREIGN PATENT DOCUMENTS

| EP | 0486289 A | 5/1992 |
| EP | 546049 | 7/1995 |
| EP | 0610048 | 9/1999 |
| EP | 0610049 | 11/1999 |
| JP | 4099495 | 3/1992 |
| JP | 4099496 | 3/1992 |
| JP | 4099497 | 3/1992 |
| JP | 4218386 | 8/1992 |
| JP | 5095795 | 4/1993 |
| JP | 5192189 | 8/1993 |
| JP | 6/0156086 | 6/1994 |
| JP | 6237789 | 8/1994 |
| JP | 6284899 | 10/1994 |
| JP | 7/213295 | 8/1995 |
| JP | 09028390 | 2/1997 |
| WO | WO93/24631 | 12/1993 |
| WO | WO 99/30781 | * 6/1999 |
| WO | WO01/75077 | 10/2001 |
| WO | WO 2002/068658 A1 | 9/2002 |
| WO | WO2005106005 | 11/2005 |
| WO | WO 2006/069114 | * 6/2006 |
| WO | WO2006068110 | 6/2006 |

OTHER PUBLICATIONS

Metz et al., "Identification of Formaldehyde-induced Modifications in Proteins," J. Biol. Chem., 279(8), 6235-6243, 2004.
Asano et al., "Aliphatic Nitrile Hydratase from Arthrobacter sp. J-1 Purification and Characterization," Agricultural Biological Chemistry, 46(5), 1165-1174, 1982.
Mowry, David, "The Preparation of Nitriles," Chemical Reviews, 42, 189-283, 1948.
Tourneix et al., Antonie van Leeuwenhoek, 52, 173-182, 1986.
Chauhan et al., Purification, cloning, sequencing and over-expression in *Escherichia coli* of a regioselective aliphatic . . . , Appl. Microbiol Biotechnol., 61, 118-122, 2003.
Athel Cornish-Bowden,"Nomenclature for incompletely specified bases in nucleic acid Sequences: recommendations 1984,"Nucleic Acids Res. 13, 3021-3030, 1985.
"Nomenclature and Symbolism for Amino Acids and Peptides," Biochemical Journal, 219(2), 345-373, 1984.

(Continued)

*Primary Examiner*—Christian L Fronda

(57) ABSTRACT

A process is provided to improve the specific activity of an enzyme catalyst having nitrilase activity when converting glycolonitrile to glycolic acid under aqueous reaction conditions. Inclusion of an effective amount of at least one amine protectant improves the specific activity and catalytic productivity of the enzyme catalyst.

19 Claims, 7 Drawing Sheets

OTHER PUBLICATIONS

Bickerstaff, G.F., Immobilization of Enzymes and Cells, Methods in Biotechnology, Ch. 4, Ch. 5, Ch. 17, Ch. 32, pp. 27-40, 41-51, 133-141, 289-298,1997. (respectively).

Wong, S.S., "Chemistry of Protein Conjugation and Crosslinking," CRC Press, Inc., Ch. 12, pp. 295-317, 1991.

Outchkourov et al., "Optimization of the Expression of Equistatin in Pichia pastoris," Protein Expr.Purif, 24(1), 18-24, 2002.

Feng at al., High-Level Expression and Mutagenesis of Recombinant Human Phophatidylcholine Transder Protein Using a Synthetic Gene . . . , Biochemistry, 39(50), 15399-15409, 2000.

Pace et al., "The nitrilase superfamily: classification, structure and function," Genome Biol., 2(1), reviews 0001.1-0001.9, 2001.

Cowan et al., "Biochemistry and Biotechnology of mesophilic and thermophilic nitrile metabolizing enzymes," Extremophiles, 2, 207-216, 1998.

Deshpande, M. V., Ethanol Production from Cellulose by Couple Saccharification/Fermentation . . . , Appl. Biochem. Biotechnol., 36(3), 227-234, 1992.

Chica et al., Semi-rational approaches to engineering enzyme activity . . . , Curr. OpIn. BIotechnol., Aug. 16(4):378-84, 2005.

Sen et al., Developments in Directed Evolution for Improving Enzyme Functions, Appl. Biochem. Biotechnol., Dec:143(3):212:23, 2007.

Desantis, et al., "Creation of a productive, highly enantioselective nitrilase through gene site saturation mutagenesis", J. Am. Chem. Soc., vol. 125, pp. 11476-11477 (2003).

Fromant, M., et al., "Direct random mutagenesis of gene-sized DNA fragments using polymerase chain reaction", Analytical Biochem., vol. 224, pp. 347-353 (1995).

Guthrie, J.P., et al., "Effect of the ACYL substituent on the equilibrium constant for hydration of esters", Canadian J. Chem., vol. 58, pp. 1281-1294 (1980).

Inci, I., "Distribution of glycolic acid between water and different organic solutions", Chem. Biochem. Eng. Q., vol. 16, pp. 81-85 (2002).

Inci, I., et al., "Extraction of glycolic acid from aqueous solutions by trioctyl methylammonium chloride and organic . . . ", J. Chem. Eng. Data, vol. 50, pp. 536-540 (2005).

Lin-Goerke, "PCR-based random mutagenesis using manganese and reduced DNTP concentration", Biotechniques, vol. 23, pp. 409-412 (1997).

Melnikov, A., et al., "Random mutagenesis by recombinational capture of PCR products in *Bacillus subtilis* and . . .", Nucleic Acids Res., vol. 27, pp. 1056-1062 (1999).

O'Reilly, C., et al., "The nitrilase family of CN hydrolyzing enzymes-a comparative study", J. Appl. Microbiol., vol. 95, pp. 1161-1174 (2003).

Tamada, J.A., et al., "Extraction of carboxylic acids with amine extractants. 1. Equilibria and law of mass action . . . ", Ind. Eng. Chem. Res., vol. 29, pp. 1319-1326 (1990).

Tamada, J.A., et al., "Extraction of carboxylic acids with amine extractants. 2. Chemical interactions and . . . ", Ind. Eng. Chem. Res., vol. 29, pp. 1327-1333 (1990).

Wasewar, K.L., et al., "Reactive extraction of lactic acid using alamine 336 in MIBK: equilibria and kinetics", J. Biotechnol., vol. 97, pp. 59-68 (2002).

Yanisch-Perron, C., et al., "Improved M13 phage cloning vectors and host strains: nucleotide sequences . . . ", NCBI Gen. ID No. 20141090, Accession No. L09137, May 22, 2002.

Notice of Allowance in U.S. Appl. No. 12/210,618, now U.S. Pat. No. 7,638,617, mailed Aug. 27, 2009.

Requirement for Restriction/Election in U.S. Appl. No. 11/712,336, now U.S. Pat. No. 7,473,545, mailed Mar. 28, 2008.

Notice of Allowance in U.S. Appl. No. 11/712,336, now U.S. Pat. No. 7,473,545, mailed Aug. 29, 2008.

Requirement for Restriction/Election in U.S. Appl. No. 11/313,541, now U.S. Pat . No. 7,198,927, mailed Aug. 14, 2006.

Notice of Allowance in U.S. Appl. No. 11/313,541, now U.S. Pat . No. 7,198,927, mailed Nov. 30, 2006.

* cited by examiner

CLUSTAL W (1.83) multiple sequence alignment

```
SEQ ID NO:4   ------------MVSYNSKFLAATVQAEPVWLDADATIDKSIGIIEEAAQKGASLIAFPEVF
SEQ ID NO:5   ------------MQTRKIVRAAAVQAASPNYDLATGVDKTIELARQARDEGCDLIVFGETW
SEQ ID NO:6   ------------MVEYTNTFKVAAVQAQPVWFDAAKTVDKTVSIIAEAARNGCELVAFPEVF
SEQ ID NO:7   ------------MVEYTNTFKVKVATVQAEPVILDADATIDKAIGFIEEAAKNGAEFLAFPEVW
SEQ ID NO:8   -----------------MKVATVQAEPVILDADATIDKAIGYIEEASKNGAEFIAFPEVW
SEQ ID NO:9   ------------MTTHRIAVIQDGPVPGDAMATAEKMSRLAASAKAQGARLALFPEAF
SEQ ID NO:10  MSTSENTPFNGVASSTIVRATIVQASTVYNDTPATLEKANKFIVEAASKGSELVVFPEAF
SEQ ID NO:11  ------------MADKIIVAAAQIRPVLFESLEGSVARVLAAMAEAAAAGVQLIVFPETF
SEQ ID NO:12  ------------MADKIIVAAAQIRPVLFESLEGSVARVLAAMAEAAAAGVQLIVFPETF
SEQ ID NO:13  ----MLGKIMLNYTKNIRAAAAQISPVLFSQQGTMEKVLDAIANAAKKGVELIVFPETF
SEQ ID NO:14  ------------MPKSIVAALQVGSLPEGKAATLEQILGYEQAIREAGARLVVMPEAL
SEQ ID NO:15  ------------MSCHRVAVIQAGTSLFDTEKTLDRMEALCRQAAEQNVELAVFPEAY
SEQ ID NO:16  ------------MSNYPKYRVAAVQASPVLLDLDATIDKTCRLVDEAAANGAKVIAFPEAF
SEQ ID NO:17  ------------MKNYPTVKVAAVQAAPVFMNLEATVDKTCKLIAEAASMGAKVIGFPEAF
SEQ ID NO:18  ------------MTTVKVAAAQIRPVLFSLDGSLQKVLDAMAEAAAQGVELIVFPETF
SEQ ID NO:19  ------------MPKSVVAALQIGALPEGKAATLEQILSYEAAIIEAGAQLVVMPEAL
SEQ ID NO:20  ------------MSQRDSFRAAAVQAAPVWLDGAATVDKCVALIEEAADNGAALIAFPETF
SEQ ID NO:21  ------------MQTRKIVRAAAVQAASPNYDLATGVDKTIELARQARDEGCDLIVFGETW
SEQ ID NO:22  ------------MKEPLKVACVQAAPVFLDLDATVDKTITLMEQAAAAGAGLIAFPEVF
SEQ ID NO:23  ----LAHPKYKVAVVQAAPAWLDDASIKKTIALIEEAADKGAKLIAFPEVF
SEQ ID NO:24  ------------MVEYTNTFKVAAVQAQPVWFDAAKTVDKTVSIIAEAARNGCELVAFPEVF
SEQ ID NO:25  ------------MVEYTNTFKVAAVQAQPVWFDAAKTVDKTVSIIAEAARNGCELVAFPEVF
                                *    :             :         :  *::
```

FIGURE 1A

| | | |
|---|---|---|
| SEQ ID NO:4 | IPGYP-----YWAWLGDVKYSLS--FTSRYHENSLELGDDRMRRLQLAARRNKIALVMGYS |
| SEQ ID NO:5 | LPGYP-----FHVWLGAPAWSLK--YSARYYANSLSLDSAEFQRIAQAARTLGIFIALGYS |
| SEQ ID NO:6 | IPGYP-----YHIWVDSPLAGMAK-FAVRYHENSLTMDSPHVQRLLDAARDHNIAVVVGIS |
| SEQ ID NO:7 | IPGYP-----YWAWIGDVKWAVSD-FIPKYHENSLTLGDDRMRRLQLAARQNNIALVMGYS |
| SEQ ID NO:8 | IPGYP-----YWAWIGDVKWAVSE-FIPKYHENSLTLGDDRMRRLQLAARQHNIAMVGYS |
| SEQ ID NO:9 | VGGYPKGADFHIELGGRTPQGRA-QYQRYAETAIAVPGPVTERIGQIAAEQDMFIVVGVI |
| SEQ ID NO:10 | IGGYPRGFRFGLGVGVHNEEGRD-EFRKYHASAIKVPGPEVEKLAELAGKNNVYLVMGAI |
| SEQ ID NO:11 | LPYYP-----YFSFVEPPVLMGRS--HLKLYEQAFTMTGPELQQIARAARQHRLFVLLGVN |
| SEQ ID NO:12 | LPYYP-----YFSFVEPPVLMGRS--HLKLYEQAFTMTGPELQQIARAARQHRLFVLLGVN |
| SEQ ID NO:13 | VPYYP-----YFSFVEPPVLMGKS--HLKLYQEAVTVPGKVTQAIAQAAKTHGMVVVLGVN |
| SEQ ID NO:14 | LGGYPKGEGFGTQLGYRLPEGRE-AFARYFANAIDVPGSETAALAGLSARTGASLVLGVI |
| SEQ ID NO:15 | IGGYPKGLDFGARMGTRTEAGRE-DFLRYWKAAIDVPGKETARIGSFAAKMKAYLVVGVI |
| SEQ ID NO:16 | IPGYP-----WWIWLGNADYGMK--YYIQLYKNSVEIPSLAVQKLSSAG-TNKVYFCVSVT |
| SEQ ID NO:17 | IPGYP-----YWIWTSNMDFTGM--MWAVLFKNAIEIPSKEVQQISDAAKKNGVYVCVSVS |
| SEQ ID NO:18 | LPYYP-----YFSFVEPPVLMGRS--HLALYEQAVVVPGPVTDAVAAAASQYGMQVLLGVN |
| SEQ ID NO:19 | LGGYPKGEGFGTQLGYRLPEGRE-AFARYFANAIEVPGVETDALAALSARTGANLVLGVI |
| SEQ ID NO:20 | VPGYP-----WWLWLDSPAWGMQ--FVARYFDNSLALDGPLFARLREAARRSAITVTGHS |
| SEQ ID NO:21 | LPGYP-----FHVWLGAPAWSLK--YSARYYANSLSLDSAEFQRIAQAARTLGIFIALGYS |
| SEQ ID NO:22 | IPGYP-----WFLWLDAPAWNMP--LVQRYHQQSLVLDSVQARRISDAARHLGLYVVLGYS |
| SEQ ID NO:23 | IPGYP-----WHIWMDSPAWCIGRGFVQRYFDNSLAYDSPQAEALRAAVRKAQLTAVLGLS |
| SEQ ID NO:24 | IPGYP-----YHIWVDSPLAGMAK-FAVRYHENSLTMDSPHVQRLLDAARDHNIAVVVGIS |
| SEQ ID NO:25 | IPGYP-----YHIWVDSPLAGMAK-FAVRYHENSLTMDSPHVQRLLDAARDHNIAVVVGIS |

FIGURE 1B

| | |
|---|---|
| SEQ ID NO:4 | EREAGSRYLSQVFIDERGEIVANRRKLKPTHVERTIYGEGNGTDFLTHDFA-FGRV |
| SEQ ID NO:5 | ERSGGSLYLGQCLIDDKGQMLWSRRKLKPTHVERTVFGEGYARDLIVSDTE-LGRV |
| SEQ ID NO:6 | ERDGGSLYMTQLVIDADGQLVARRRKLKPTHVERSVYGEGNGSDISVYDMP-FARL |
| SEQ ID NO:7 | EKDGASRYLSQVFIDQNGDIVANRRKLKPTHVERTIYGEGNGTDFLTHDFG-FGRV |
| SEQ ID NO:8 | EKDGASRYLSQVFIDQNGDIVANRRKLKPTHVERTIYGEGNGTDFLTHDFG-FGRV |
| SEQ ID NO:9 | ERDGGTLYCTILFFSPEGELLGKHRKLMPTALERLLWGYGDGSTFPVYDTP-LGKL |
| SEQ ID NO:10 | EKDGYTLYCTALFFSPQGQFLGKHRKLMPTSLERCIWGQGDGSTIPVYDTP-IGKL |
| SEQ ID NO:11 | ERDGGSLYNTQLLISDQGDLLLKRRKITPTYHERMVWGQGGAGLTVVETV-LGKV |
| SEQ ID NO:12 | ERDGGSLYNTQLLISDQGDLLLKRRKITPTYHERMVWGQGGAGLTVVETV-LGKV |
| SEQ ID NO:13 | EREEGSLYNTQLIFDADGALVLKRRKITPTYHERMVWGQGDGAGLRTVDTT-VGRL |
| SEQ ID NO:14 | ERSGNTLYCTVLFFEPEGGLVAKHRKLMPTGTERLIWGKGDGSTLPVVDGR-AGRI |
| SEQ ID NO:15 | ERSEATLYCTALFFAPDGTLIGKHRKLMPTATERLVWGQGDGSTIEILDTA-VGKL |
| SEQ ID NO:16 | EKDGGSLYLTQLWFDPNGDLIGKHRKLKATNAEKTIWGDGDGSMMPVFETE-FGNL |
| SEQ ID NO:17 | EKDNASLYLTQLWFDPNGNLIGKHRKFKPTSSERAVWGDGDGSMAPVFKTE-YGNL |
| SEQ ID NO:18 | ERDGGTLYNTQLLFNSCGELVLKRRKITPTYHERMVWGQGDGSGLKVVQTP-LARV |
| SEQ ID NO:19 | ERSGSTLYCTALYFDPQQGLSGKHRKLMPTGTERLIWGKGDGSTLPVLDTQ-VGRV |
| SEQ ID NO:20 | ERDGGSLYMGQAIIGADGEVLAARRKLKPTHVERTVFGESDGSNLTVVDTE-LGRL |
| SEQ ID NO:21 | ERSGGSLYLGQCLIDDKGEMLWSRRKLKPTHVERTVFGEGYARDLIVSDTE-LGRV |
| SEQ ID NO:22 | ERNKASLYIGQWIIDDHGETVGVRRKLKATHVERTMFGEGDGASLRTEFTP-VGVL |
| SEQ ID NO:23 | ERDGGSLYIAQWLIGADGETIAKRRKLRPTHAERTVYGEGDGSDLAVHERPDIGRI |
| SEQ ID NO:24 | ERDGGSLYMTQLIIDADGQLVARRRKLKPTHVERSVYGEGNGSDISVYDMP-FARL |
| SEQ ID NO:25 | ERDGGSLYMTQLIIDADGQLVARRRKLKPTHVERSVYGEGNGSDISVYDMP-EARL |

FIGURE 1C

| | | |
|---|---|---|
| SEQ ID NO:4 | ...SKFMMYSLGEQVHVASWPAMSPLQPDVFQLSIEANATV------ | TRSYAIE |
| SEQ ID NO:5 | ...SKYALYSQHEAIHIAAWPSFSLYSEQAHALSAKVNMAA------ | SQIYSVE |
| SEQ ID NO:6 | ...TKYAMYSMHEQVHVASWPGMSLYQPEVPAFGVDAQLTA------ | TRMYALE |
| SEQ ID NO:7 | ...SKYMMYSLNEQIHVASWPAMFALTPDVHQLSVEANDTV------ | TRSYAIE |
| SEQ ID NO:8 | ...SKYMMYSLNEQIHVASWPAMFALTPDVHQLSVEANDTV------ | TRSYAIE |
| SEQ ID NO:9 | ...LRMAMYGKQIQIYCAPTADDKPTWVSTMQ--------------- | HVALE |
| SEQ ID NO:10 | ...YRTALYAKGIELYCAPTADGSKEWQSSML--------------- | HIAIE |
| SEQ ID NO:11 | ...ARFSLMTQGEEIHCAQFPGSLVGPIFSEQTAVT----------- | LRHHALE |
| SEQ ID NO:12 | ...ARFSLMTQGEEIHCAQFPGSLVGPIFSEQTAVT----------- | LRHHALE |
| SEQ ID NO:13 | ...ARYALMAQHEQIHCGQFPGSMVGQIFADQMEVT----------- | MRHHALE |
| SEQ ID NO:14 | ...LRTAMYAKGVQLWCAPTVDERELWQVSMR-------------- | HVAAE |
| SEQ ID NO:15 | ...LRQVMYAGGVNIWCAPTVDQREIWQVSMR--------------- | HIAYE |
| SEQ ID NO:16 | ...NVAAMASMNEQVHVASWPIGMPQ--EGHLFGPEQCVTA------ | TKYYAIS |
| SEQ ID NO:17 | ...NIAAMGSLNEQVHVASWPAFVPKGAVSSRVSSSVCASTNAMHQIISQFYAIS |
| SEQ ID NO:18 | ...ARYALMAQGEEIHCAQFPGSLVGPIFTEQTAVT----------- | MRHHALE |
| SEQ ID NO:19 | ...LRTAMYAQGIEVWCAPTVDEREMWQVSMR--------------- | HIAHE |
| SEQ ID NO:20 | ...TKYAMYSQHEQIHVAAWPSFSVYRGAAYALGPEVNTGA------ | ARQYAVE |
| SEQ ID NO:21 | ...SKYALYSQHEAIHIAAWPSFSLYSEQAHALSAKVNMAA------ | SQIYSVE |
| SEQ ID NO:22 | ...SKYAMYAQNEQIHVAAWPSFSLYRNATSALGPEVNTAA------ | SRVYAAE |
| SEQ ID NO:23 | ...SKYAMYAQNEQVHVAAWPSFSLYDPFAPALGAEVNNAA------ | SRVYAVE |
| SEQ ID NO:24 | ...TKYAMYSMHEQVHVASWPGMSLYQPEVPAFGVDAQLTA------ | TRMYALE |
| SEQ ID NO:25 | ...TKYAMYSMHEQVHVASWPGMSLYQPEVPAFGVDAQLTA------ | TRMYALE |

FIGURE 1D

```
SEQ ID NO:4   GQTFVLCSTQVIG----PSAIETFCLNDE--QRALLPQGCGWARIYGPDGSELAKPLAED
SEQ ID NO:5   GQCFTIAASSVVT----QETLDMLEVGEH--NASLLKVGGGSSMIFAPDGRTLAPYLPHD
SEQ ID NO:6   GQTFVVCTTQVVT----PEAHEFFCDNDE--QRKLIGRGGFARIIGPDGRDLATPLAED
SEQ ID NO:7   GQTFVLASTHVIG----KATQDLFAGDDDA-KRALLPLGQGWARIYGPDGKSLAEPLPED
SEQ ID NO:8   GQTFVLAATHVIG----KATQDLFAGDDEA-KRALLPLGQGWARIYGPDGKSLAEPLAEN
SEQ ID NO:9   GRCFVLSACQHLRGKDFPPEFHNALDVQP---DTVLMRGGSCIVDPMGQLLAGPVY-D
SEQ ID NO:10  GGCFVLSACQFCLRKDFPDHPDYLFTDWYDDKEPDSIVSQGGSVIISPLGQVLAGPNF-E
SEQ ID NO:11  AGCFVLSSTAWLD----PADYDTITPDRS--LHKAFQGGCHTAIISPEGRYLAGPLP-E
SEQ ID NO:12  AGCFVLSSTAWLD----PADYDTITPDRS--LHKAFQGGCHTAIISPEGRYLAGPLP-E
SEQ ID NO:13  SGCFVINATGWLT----AEQKLQITTDEK--MHQALSGGCYTAIISPEGKHLCEPIA-E
SEQ ID NO:14  GRCFVISACQVQ-----DSPAALGMEVANWPA--ERPLINGGSLIVGPLGDVLAGPLL-G
SEQ ID NO:15  GRLFVLSACQYMTRADAPADYDCIQGNDP----ETELIAGGSVIIDPMGNILAGPLY-G
SEQ ID NO:16  NQVFCLLSSQIWT----EEQRDKICETEE--QRNFMKVGHGFSKIIAPNGMEIGNKLAHD
SEQ ID NO:17  NQVYVIMSTNLVG----QDMIDMIGKDEF--SKNFLPLGSGNTAIISNTG-EILASIPQD
SEQ ID NO:18  AGCFVICSTGWLH----PDDYASITSESG--LHKAFQGGCHTAVISPEGRYLAGPLP-D
SEQ ID NO:19  GRCFVVSACQVQ-----ASPEELGIEIANWPA--QRPLIAGGSVIVGPMGDVLAGPLV-G
SEQ ID NO:20  GQCFVLSPCAVID----EAGVELFCDTPA--KRELLPGGGFAQIYGPDGRELGTALPET
SEQ ID NO:21  GQCFTIAASSVVT----QETLDMLEVGEH--NAPLLKVGGGSSMIFAPDGRTLAPYLPHD
SEQ ID NO:22  GQCFVLAPCAIVS----PEMIEMLCDSDA--KRSLLQAGGGHARIFGPDGSDLATPLGEH
SEQ ID NO:23  GSCFVLAPCATVS----QAMIDELCDRPD--KHALLHAGGGHAAIFGPDGSALAAQLPPD
SEQ ID NO:24  GQTFVVCTTQVVT----PEAHEFFCENEE--QRKLIGRGGFARIIGPDGRDLATPLAED
SEQ ID NO:25  GQTFVVCTTQVVT----PEAHEFFCENEE--QRMLIGRGGFARIIGPDGRDLATPLAED
                 :      :             :                   *         :  :
```

FIGURE 1E

| | | |
|---|---|---|
| SEQ ID NO:4  | AEGILYAEIDLEQILLAKAGADPVGHYSRPDVLSVQFDPRNHTPVHRIGIDGRLDVNTRS | |
| SEQ ID NO:5  | AEGLIIADLNMEEIAFAKAINDPVGHYSKPEATRLVLDLGHREPMTRVHSK----SVIQEE | |
| SEQ ID NO:6  | EEGILYADIDLSAITLAKQAADPVGHYSRPDVLSLNFNQRHTTPVN-------TAISTI | |
| SEQ ID NO:7  | AEGLLYAELDLEQIILAKAAADPAGHYSRPDVLSLKIDTRNHTPVQYITADGRTSLNSNS | |
| SEQ ID NO:8  | AEGLLYAELDLEQIIVAKAAADPAGHYSRPDVLSLKVDTRNHTPVQYVTEDGGSSLNSNS | |
| SEQ ID NO:9  | EDAILVADIDLDAVTRGKMDFDVVGHYARPDIFSLTVDERPKPPVTTL--------K | |
| SEQ ID NO:10 | SEGLITADIDLDLGDVARAKLYFDSVGHYSRPDVLHLTVNEHPKKPVTFI---------S | |
| SEQ ID NO:11 | GEGLAIAELDKSLITKRKRMMDSVGHYSRPDLLSLRINRSPATQVQAIG----------S | |
| SEQ ID NO:12 | GEGLAIAELDKSLITKRKRMMDSVGHYSRPDLLSLRINRSPATQVQAIG----------S | |
| SEQ ID NO:13 | GEGLAIADLDFSLIAKRKRMMDSVGHYARPDLLQLTLNNQPWSALEAN----------P | |
| SEQ ID NO:14 | ARGLVCAEVDTELVRARYDFDVVGHYARPDVFELSVDERPRPGVR-----------F | |
| SEQ ID NO:15 | QEGVLVADIDLSDTIKARYDLDVSGHYGRPDIFEIKVDRQSHQVITDQ----------F | |
| SEQ ID NO:16 | EEGITYADIDLEQIIPGKFLIDSAGHYSTPGFLSLSFDRTEKKPIKHIG----------E | |
| SEQ ID NO:17 | AEGIAVAEIDLNQIIYGKWLLDPAGHYSTPGFLSLTFDQSEHVPVKKIG--------E | |
| SEQ ID NO:18 | GEGLAIADLDLALITKRKRMMDSVGHYSRPELLSLQINSSPAVPVQNM---------S | |
| SEQ ID NO:19 | RAGLISAQIDTADLVRARYDYDVVGHYARPDVFELTVDQRPRPGVR----------F | |
| SEQ ID NO:20 | EEGLLVYADLEASAVAVAKSAADPVGHYGHYSRPDVLQLLWDP----RPRSVVR-------Q | |
| SEQ ID NO:21 | AEGLIIADLNMEEIAFAKAINDPVGHYSKPEATRLVLDLGHRDPMTRVHSK----SVTREE | |
| SEQ ID NO:22 | EEGLLYATLDPAALTLAKVAADPAGHYSRPDVTRLMFNP-----NPTPCVV--------D | |
| SEQ ID NO:23 | QEGLLIAEIDLGMIGIAKNAADPAGHYSRPDVTRLLLNK---KPLNRVE---------H | |
| SEQ ID NO:24 | EEGILYADIDLSAITLAKQAADPVGHYSRPDVLSLNFNQRRTTPVN-------TPLSTI | |
| SEQ ID NO:25 | EEGILYADIDLSAITLAKQAADPVGHYSRPDVLSLNFNQRRTTPVN-------TPLSTI | |
| | :  * ::      * .::      ***.     *           :    :  | |

FIGURE 1F

```
SEQ ID NO:4   RVENFRLRQAAEQERQASKRLGTKLFEQS------------------------------LLAEEPVPAK-----
SEQ ID NO:5   APEPHVQSTAAPVAVSQTQDSDTLLVQEPS----------------------------------------------
SEQ ID NO:6   HATHTLVPQSGALDGVRELNGADEQRALPS-------------------------------THSDETDRATASI
SEQ ID NO:7   RVENYRLHQLADIEKYENAEAATLPLDAPAPAP-----------------------------APEQKSGRAKAEA
SEQ ID NO:8   RVENYRLRQLADIEKYENADSATVPLDVTTPEKQSGDVNANGNAKVNTNPSAKAKA
SEQ ID NO:9   P---------------------------------------------------------------------------
SEQ ID NO:10  KVEKAEDDSNK-----------------------------------------------------------------
SEQ ID NO:11  AAALPELPNLEAAPAETAEDYLHA----------------------------------------------------
SEQ ID NO:12  AAALPELPNLEAAPAETAEDYLHA----------------------------------------------------
SEQ ID NO:13  VTPNAIPAVSDPELTETIEALPNNPIFSH-----------------------------------------------
SEQ ID NO:14  IG--------------------------------------------------------------------------
SEQ ID NO:15  SRDQATEKKPVSDSEISQLD--------------------------------------------------------
SEQ ID NO:16  SAQETVTYEEIQYGNKANVKVHS-----------------------------------------------------
SEQ ID NO:17  QTNHFISYEDLHEDKMDMLTIPPRRVATA-----------------------------------------------
SEQ ID NO:18  TASVPLEPATATDALSSMEALNHV----------------------------------------------------
SEQ ID NO:19  T---------------------------------------------------------------------------
SEQ ID NO:20  VA-LSVASPAESAD---------------DAEPAVR----------------------------------------
SEQ ID NO:21  APEQGVQSKIASVAISHPQDSDTLLVQEPS----------------------------------------------
SEQ ID NO:22  LPDLPISSESIELL-----------RPDIALEV-------------------------------------------
SEQ ID NO:23  FS-LPVDSAAAALPGEAAVARPDQSI--------------------------------------------------
SEQ ID NO:24  HATHTFVPQFGALDGVRELNGADEQRALPS-------------------------------THSDETDRATATL
SEQ ID NO:25  HATHTFVPQFGALDGVRELNGADEQRALPS-------------------------------THSDETDRATATL
```

FIGURE 1G

PROCESS FOR ENZYMATICALLY CONVERTING GLYCOLONITRILE TO GLYCOLIC ACID

FIELD OF THE INVENTION

This invention relates to the field of organic acid synthesis, molecular biology, and microbiology. More specifically, a process is provided to protect and/or increase the specific activity of an enzyme catalyst comprising a polypeptide having nitrilase activity when converting glycolonitrile to glycolic acid by conducting the reaction in the presence of an amine protectant.

BACKGROUND OF THE INVENTION

Glycolic acid (HOCH$_2$COOH; CAS Registry Number is 79-14-1) is the simplest member of the α-hydroxy acid family of carboxylic acids. Its properties make it ideal for a broad spectrum of consumer and industrial applications, including use in water well rehabilitation, the leather industry, the oil and gas industry, the laundry and textile industry, as a monomer in the preparation of polyglycolic acid (PGA), and as a component in personal care products. Glycolic acid also is a principle ingredient for cleaners in a variety of industries (dairy and food processing equipment cleaners, household and institutional cleaners, industrial cleaners [for transportation equipment, masonry, printed circuit boards, stainless steel boiler and process equipment, cooling tower/heat exchangers], and metals processing [for metal pickling, copper brightening, etching, electroplating, electropolishing]). Recently, it has been reported that polyglycolic acid is useful as a gas barrier material (i.e., exhibits high oxygen barrier characteristics) for packing foods and carbonated drinks (WO 2005/106005A1). However, traditional chemical synthesis of glycolic acid produces a significant amount of impurities that must be removed prior to use in preparing polyglycolic acid for gas barrier materials. New technology to commercially produce glycolic acid, especially one that produces glycolic acid in high purity and at low cost; would be eagerly received by industry.

Microbial catalysts can hydrolyze a nitrile (e.g., glycolonitrile) directly to the corresponding carboxylic acids (e.g., glycolic acid) using a nitrilase (EC 3.5.5.7), where there is no intermediate production of the corresponding amide (Equation 1), or by a combination of nitrile hydratase (EC 4.2.1.84) and amidase (EC 3.5.1.4) enzymes, where a nitrile hydratase (NHase) initially converts a nitrile to an amide, and then the amide is subsequently converted by the amidase to the corresponding carboxylic acid (Equation 2):

(1)

(2)

Enzymatic synthesis of glycolic acid typically requires a substantially pure form of glycolonitrile. Methods to synthesize glycolonitrile by reacting aqueous solutions of formaldehyde and hydrogen cyanide have previously been reported (U.S. Pat. No. 2,175,805; U.S. Pat. No. 2,890,238; and U.S. Pat. No. 5,187,301; Equation 3).

(3)

However, these methods typically result in an aqueous glycolonitrile reaction product that requires significant purification (e.g., distillative purification) as many of the impurities and/or byproducts of the reaction (including excess reactive formaldehyde) may interfere with the enzymatic conversion of glycolonitrile to glycolic acid, including suppression of catalyst activity (i.e., decreased specific activity). In particular, it is well known that formaldehyde can create undesirable modifications in proteins by reacting with amino groups from N-terminal amino acid residues and the side chains of arginine, cysteine, histidine, and lysine residues (Metz et al., *J. Biol. Chem.*, 279 (8): 6235-6243 (2004)). Suppression of catalyst activity decreases the overall productivity of the catalyst (i.e., total grams of glycolic acid formed per gram of catalyst), adding a significant cost to the overall process that may make enzymatic production economically non-viable when compared to chemical synthesis. As such, reaction conditions are needed that can help to protect the enzymatic activity against undesirable impurities reported decrease the activity of the catalyst.

A method of producing high purity glycolonitrile has been reported by subjecting the formaldehyde to a heat treatment prior to the glycolonitrile synthesis reaction (U.S. Ser. No. 11/314,386 and U.S. Ser. No. 11/314,905; Equation 3). However, glycolonitrile can reversibly disassociate into formaldehyde and hydrogen cyanide. As such, there remains a need to protect a catalyst having nitrilase activity against the undesirable effects of free formaldehyde.

Various methods are known for preparing α-hydroxy acids using the corresponding α-hydroxy nitrite as the starting material and a microorganism as the catalyst. Examples of α-hydroxy acids produced include: glycolic acid, lactic acid, 2-hydroxyisobutyric acid, 2-hydroxy-2-phenyl propionic acid, mandelic acid, 2-hydroxy-3,3-dimethyl-4-butyrolactone, and 4-methylthiobutyric acid. These products are synthesized using microorganisms, such as those belonging to the genera *Nocardia, Bacillus, Brevibacterium, Aureobacterium, Pseudomonas, Caseobacter, Alcaligenes, Acinetobacter, Enterobacter, Arthrobacter, Escherichia, Micrococcus, Streptomyces, Flavobacterium, Aeromonas, Mycoplana, Cellulomonas, Erwinia, Candida, Bacteridium, Aspergillus, Penicillium, Cochliobolus, Fusarium, Rhodopseudomonas, Rhodococcus, Corynebacterium, Microbacterium, Obsumbacterium* and *Gordona*, (JP-A4-994951, JP-A-4-99496 and JP-A-4-218385 corresponding to U.S. Pat. No. 5,223,416; JP-A-4-99497 corresponding to U.S. Pat. No. 5,234,826; JP-A-5-95795 corresponding to U.S. Pat. No. 5,296,373; JP-A-5-21987; JP-A-5-19189 corresponding to U.S. Pat. No. 5,326,702; JP-A-6-237789 corresponding to EP-A-0610048, JP-A-6-284899 corresponding to EP-A-0610049; JP-A-7-213296 corresponding to U.S. Pat. No. 5,508,181).

However, most known methods for preparing α-hydroxy acids from the corresponding α-hydroxy nitriles as mentioned above do not produce and accumulate a product at a sufficiently high concentration to meet commercial needs. This is frequently a result of enzyme inactivation early in the reaction period. U.S. Pat. No. 5,756,306 teaches that "When an α-hydroxy nitrite is enzymatically hydrolyzed or hydrated using nitrilase or nitrite hydratase to produce an α-hydroxy acid or α-hydroxy amide, a problem occurs in that the enzyme is inactivated within a short period of time. It is therefore difficult to obtain the α-hydroxy acid or α-hydroxy amide in high concentration and high yield." (col. 1, lines 49-54). Maintaining the aldehyde concentration (formed by the disassociation of α-hydroxy nitrite to aldehyde and hydrogen cyanide) and/or the α-hydroxy nitrite concentration in the reaction mixture within a specified range is one method to avoid this problem.

U.S. Pat. No. 5,508,181 addresses further difficulties relating to rapid enzyme inactivation. Specifically, U.S. Pat. No. 5,508,181 mentions that α-hydroxy nitrite compounds partially disassociate into the corresponding aldehydes, according to the disassociation equilibrium. These aldehydes were reported to inactivate the enzyme within a short period of time by binding to the protein, thus making it difficult to obtain α-hydroxy acid or α-hydroxy amide in a high concentration with high productivity from α-hydroxy nitriles (col. 2, lines 16-29). As a solution to prevent enzyme inactivation due to accumulation of aldehydes, phosphate or hypophosphite ions were added to the reaction mixture. U.S. Pat. No. 5,326,702 reports the use of sulfite, disulfite, or dithionite ions to sequester aldehyde and prevent enzyme inactivation, but concludes that the concentration of α-hydroxy acid produced and accumulated even by using such additives as described above is not great.

U.S. Pat. No. 6,037,155 teaches that low accumulation of α-hydroxy acid product is related to enzyme inactivation within a short time due to the disassociated-aldehyde accumulation. These inventors suggest that enzymatic activity is inhibited in the presence of hydrogen cyanide (Asano et al., *Agricultural Biological Chemistry*, Vol. 46, pages 1165-1174 (1982)) generated in the partial disassociation of the α-hydroxy nitrite in water together with the corresponding aldehyde or ketone (Mowry, David T., *Chemical Reviews*, Vol. 42, pages 189-283 (1948)). The inventors solved the problem of aldehyde-induced enzyme inactivation by using microorganisms whose enzyme activity could be improved by adding a cyanide substance to the reaction mixture. The addition of a cyanide substance limited the disassociation of α-hydroxy nitrite to aldehyde and hydrogen cyanide.

With specific respect to the production of glycolic acid, glycolonitrile is known to reversibly disassociate to hydrogen cyanide and formaldehyde, either of which may be involved in reducing catalyst activity. U.S. Pat. No. 3,940,316 describes a process for preparing an organic acid from the corresponding nitrite using bacteria with "nitrilasic" activity, and lists glycolonitrile as a substrate. In particular, this patent describes the use of *Bacillus, Bacteridium, Micrococcus*, and *Brevibacterium* for this purpose. Though described as having nitrilasic activity, *Brevibacterium* R312 is the only strain used in all of the U.S. Pat. No. 3,940,316 examples. *Brevibacterium* R312 is known to have nitrite hydratase and amidase activities, but no nitrilase activity (Tourneix et al., *Antonie van Leeuwenhoek*, 52:173-182 (1986)).

A method for preparing lactic acid, glycolic acid, and 2-hydroxyisobutyric acid by using a microorganism belonging to *Corynebacterium* spp. is disclosed in Japanese Patent Laid-open No. Sho 61-56086. JP 09028390 discloses a method for manufacturing glycolic acid from glycolonitrile by the action of *Rhodococcus* or *Gordona* hydrolase. Selectivity for glycolic acid is reported as almost 100%, without formation of glycolic acid amide. U.S. Pat. No. 6,037,155 discloses examples of methods for producing α-hydroxy acids from α-hydroxy nitriles, including glycolic acid. This disclosure acknowledges that not all microbial catalysts can produce high concentrations of glycolic acid due to the aforementioned problems and instructs that screening studies must be conducted in order to find industrially advantageous microorganisms. U.S. Pat. No. 6,037,155 specifically identifies *Variovorax* spp. and *Arthrobacter* spp. microorganisms that are resistant to the suppressing effect of α-hydroxy nitrile or α-hydroxy acid, have durable activity, and can produce the desired product at high concentration.

*Acidovorax facilis* 72W (ATCC 55746) is characterized by aliphatic nitrilase (EC 3.5.5.7) activity, as well as a combination of nitrile hydratase (EC 4.2.1.84) and amidase (EC 3.5.1.4) activities. The gene encoding the *A. facilis* 72W (ATCC 55746) nitrilase has been cloned and recombinantly expressed (WO 01/75077 corresponding to U.S. Pat. No. 6,870,038) and Chauhan et al., *Appl Microbiol Biotechnol*, 61:118-122 (2003)).

The *A. facilis* 72W nitrilase converts α-hydroxynitriles to the corresponding α-hydroxycarboxylic acids in high yield (U.S. Pat. No. 6,383,786), including glycolic acid (U.S. Pat. No. 6,416,980). An improved process to produce glycolic acid from glycolonitrile using mutants derived from the *A. facilis* 72W nitrilase is disclosed in WO2006/068110 and WO2006/069114 (corresponding to U.S. Pat. No. 7,198,927 and U.S. patent application Ser. No. 11/314,905, respectively). In co-pending and commonly owned U.S. patent application Ser. No. 11/314,905, various means to improve production of glycolic acid are disclosed including (1) the use of *A. facilis* 72W mutants having improved activity, (2) the addition of at least one stabilizing agent (e.g. potassium thiosulfate, sodium dithionite, excess HCN), (3) running the reaction under oxygen free conditions, (4) controlling the glycolonitrile feed rate, and (5) the use of high purity glycolonitrile. Even though many of these means improved glycolic acid productivity, a decrease in enzymatic activity was generally observed over time. This decrease in activity is typically attributed, at least in part, to the presence of formaldehyde (albeit at low levels) in the reaction mixture. A process to protect the specific activity of an enzyme catalyst having nitrilase activity when converting glycolonitrile to glycolic acid in the presence of formaldehyde would significantly improve the economics of glycolic acid synthesis.

The problem to be solved is to provide a process to stabilize and/or increase the specific activity of an enzyme catalyst having nitrilase activity when converting glycolonitrile to glycolic acid in the presence of formaldehyde.

SUMMARY OF THE INVENTION

The present problem has been solved by providing a process for stabilizing and/or increasing the specific activity of a nitrilase catalyst comprising a polypeptide having nitrilase activity when enzymatically converting glycolonitrile to glycolic acid, said process comprising:
    (a) providing a set of reaction components comprising:
      (i) an aqueous solution of glycolonitrile comprising at least 0.01 ppm formaldehyde;
      (ii) an enzyme catalyst comprising a polypeptide having nitrilase activity wherein said polypeptide comprises a catalytic signature motif of SEQ ID NO: 1; wherein said enzyme catalyst comprises a specific activity for hydrolyzing glycolonitrile to glycolic acid; and
      (iii) an effective amount of at least one amine protectant selected from the group consisting of:
        a) a compound of the formula

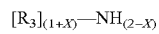

wherein X is 0 or 1 and $R_3$ is independently C1 to C20 hydrocarbyl group or substituted hydrocarbyl group; wherein R3 optionally comprises one or more ether linkages; with the proviso that (i) the substituted group is preferably not a cyano group capable of reacting with the enzyme catalyst and (ii) $R_3$ is not a carbonyl group,
        b) a polyamine polymer comprising an effective number of free amine groups; and
        c) an amine-functionalized material comprising an effective number of free amine groups;
      wherein the amine protectant is not naturally-produced by said enzyme catalyst;
    (b) combining the set of reaction components under suitable aqueous reaction conditions whereby glycolic acid is produced; wherein said specific activity is increased by the addition of said at least one amine protectant; and (c) recovering the glycolic acid or salt thereof produced in (b).

BRIEF DESCRIPTION OF THE FIGURE, SEQUENCE LISTING, AND THE BIOLOGICAL DEPOSITS

The invention can be more fully understood from the sequence listing, the biological deposits, the FIGURE, and the detailed description that together form this application.

FIGURE

FIG. 1, panels A-G, is a CLUSTALW alignment (version 1.83 using default parameters) of various nitrilase sequences. The conserved catalyst signature sequence surrounding the catalyst cysteine residue is highlighted in gray shading. The amino acids representing the catalytic triad ($Glu_{48}$, $Lys_{130}$, and $Cys_{164}$; numbering based on the amino acid sequence SEQ ID NO: 4) are underlined.

SEQUENCE LISTING

The following sequence descriptions and sequences listings attached hereto comply with the rules governing nucleotide and/or amino acid sequence disclosures in patent applications as set forth in 37 C.F.R. §1.821-1.825. The Sequence Descriptions contain the one letter code for nucleotide sequence characters and the three letter codes for amino acids as defined in conformity with the IUPAC-IYUB standards described in Nucleic Acids Research 13:3021-3030 (1985) and in the Biochemical Journal 219 (No. 2):345-373 (1984) which are herein incorporated by reference. The symbols and format used for nucleotide and amino acid sequence data comply with the rules set forth in 37 C.F.R. §1.822.

SEQ ID NO: 1 is the amino acid sequence of the catalytic signature motif encompassing the essential cysteine residue of nitrilase enzymes (Formula 1).

SEQ ID NO: 2 is the amino acid sequence of a preferred catalyst signature motif encompassing the essential cysteine residue of nitrilase enzymes (Formula 2)

SEQ ID NO: 3 is the nucleotide sequence of the *Acidovorax facilis* 72W nitrilase coding sequence comprising a change in the start codon from TTG to ATG to facilitate recombinant expression in *E. coli*.

SEQ ID NO: 4 is the deduced amino acid sequence of the *Acidovorax* facilis 72W nitrilase (ATCC 55746).

SEQ ID NO: 5 is the amino acid sequence of the *Alcaligenes faecalis* JM3 nitrilase (GENBANK® BAA02684.1).

SEQ ID NO. 6 is the amino acid sequence of the *Rhodococcus rhodochrous* J1 nitrilase (GENBANK® Q03217).

SEQ ID NO; 7 is the amino acid sequence of the *Rhodococcus rhodochrous* K22 nitrilase (GENBANK® Q02068).

SEQ ID NO: 8 is the amino acid sequence of the *Nocardia* sp. C-14-1 nitrilase (GENBANK® AAX18182.1).

SEQ ID NO: 9 is the amino acid sequence of the *Bordetella bronchiseptica* RB50 nitrilase (GENBANK® NP-887662.1).

SEQ ID NO: 10 is the amino acid sequence of the *Arabidopsis thaliana* nitrilase (GENBANK® AAB60275.1 and AMA19627.1).

SEQ ID NO: 11 is the amino acid sequence of the *Synechococcus elongatus* PCC 7942 nitrilase (GENBANK®YP_399857.1).

SEQ ID NO: 12 is the amino acid sequence of the *Synechococcus elongatus* PCC 6301 nitrilase (GENBANK®YP_171411.1).

SEQ ID NO: 13 is the amino acid sequence of the *Synechocystis* sp. PCC 6803 nitrilase (GENBANK® NP_442646.1).

SEQ ID NO: 14 is the amino acid sequence of the *Pseudomonas entomophila* L48 nitrilase (GENBANK®YP_6090481.1).

SEQ ID NO: 15 is the amino acid sequence of the *Zymomonas moblis* nitrilase (GENBANK® YP_162942.1).

SEQ ID NO: 16 is the amino acid sequence of the *Bacillus* sp. OxB-1 nitrilase (GENBANK® BAA90460.1).

SEQ ID NO: 17 is the amino acid sequence of the *Comamonas testosteroni* nitrilase (GENBANK® AAA82085.1).

SEQ ID NO: 18 is the amino acid sequence of the *Synechococcus* sp. CC9605 nitrilase (GENBANK® YP_381420.1).

SEQ ID NO: 19 is the amino acid sequence of the *Pseudomonas fluorescens* Pf-5 nitrilase (GENBANK® YP_260015.1).

SEQ ID NO: 20 is the amino acid sequence of the *Nocardia farcinica* IFM 10152 nitrilase (GENBANK® YP_119480.1).

SEQ ID NO: 21 is the amino acid sequence of the *Alcaligenes faecalis* 1650 nitrilase (GENBANK® AAY06506.1).

SEQ ID NO: 22 is the amino acid sequence of the *Pseudomonas syringae* pv. *syringae* B728a nitrilase (GENBANK® AAY35081.1).

SEQ ID NO: 23 is the amino acid sequence of the *Bradyrhizobium* sp. BTAi1 nitrilase (GENBANK®ZP_00859948.1).

SEQ ID NO: 24 is the amino acid sequence of the *Rhodococcus rhodochrous* NCIMB 11216 nitrilase (GENBANK® CAC88237).

SEQ ID NO: 25 is the amino acid sequence of *Rhodococcus rhodochrous* ATCC™ 39484

SEQ ID NO: 26 is the nucleotide sequence of an *A. facilis* 72W nitritase mutant comprising a codon change which resulted in a single amino acid substitution at residue position 201 (L201Q; Leu➔Gln).

SEQ ID NO: 27 is the deduced amino acid sequence of the mutant nitrilase (SEQ ID NO: 26) comprising a single amino acid substitution at residue position 201 (Leu201➔Gln) of the *A. facilis* 72W nitrilase.

SEQ ID NO: 28 is the nucleotide sequence of an *A. facilis* 72W nitrilase mutant comprising a codon change which resulted in a single amino acid substitution at residue position 201 (L201A; Leu➔Ala).

SEQ ID NO: 29 is the deduced amino acid sequence of the mutant nitrilase (SEQ ID NO: 28) comprising a single amino acid substitution at residue position 201 (Leu20➔Ala) of the *A. facilis* 72W nitrilase.

SEQ ID NO: 30 is the nucleotide sequence of an *A. facilis* 72W nitrilase mutant comprising a codon change which resulted in a single amino acid substitution at residue position 201 (L201C; Leu➔Cys).

SEQ ID NO: 31 is the deduced amino acid sequence of the mutant nitrilase (SEQ ID NO: 30) comprising a single amino acid substitution at residue position 201 (Leu201➔Cys) of the *A. facilis* 72W nitrilase.

SEQ ID NO: 32 is the nucleotide sequence of an *A. facilis* 72W nitrilase mutant comprising a codon change which resulted in a single amino acid substitution at residue position 201 (L201T; Leu➔Thr).

SEQ ID NO: 33 is the deduced amino acid sequence of the mutant nitrilase (SEQ ID NO: 32) comprising a single amino acid substitution at residue position 201 (Leu201➔Thr) of the *A. facilis* 72W nitrilase.

SEQ ID NO: 34 is the nucleotide sequence of an *A. facilis* 72W nitrilase mutant comprising a codon change which resulted in a single amino acid substitution at residue position 201 (L201G; Leu➔Gly).

SEQ ID NO: 35 is the deduced amino acid sequence of the mutant nitrilase (SEQ ID NO: 34) comprising a single amino acid substitution at residue position 201 (Leu201➔Gly) of the *A. facilis* 72W nitrilase.

SEQ ID NO: 36 is the nucleotide sequence of an *A. facilis* 72W nitrilase mutant comprising a codon change which resulted in a single amino acid substitution at residue position 201 (L201H; Leu➔His).

SEQ ID NO: 37 is the deduced amino acid sequence of the mutant nitrilase (SEQ ID NO: 36) comprising a single amino acid substitution at residue position 201 (Leu201➔His) of the *A. facilis* 72W nitrilase.

SEQ ID NO: 38 is the nucleotide sequence of an *A. facilis* 72W nitrilase mutant comprising a codon change which resulted in a single amino acid substitution at residue position 201 (L201K; Leu➔Lys).

SEQ ID NO: 39 is the deduced amino acid sequence of the mutant nitrilase (SEQ ID NO: 38) comprising a single amino acid substitution at residue position 201 (Leu201➔Lys) of the *A. facilis* 72W nitrilase.

SEQ ID NO: 40 is the nucleotide sequence of an *A. facilis* 72W nitrilase mutant comprising a codon change which resulted in a single amino acid substitution at residue position 201 (L201N; Leu➔Asn).

SEQ ID NO: 41 is the deduced amino acid sequence of the mutant nitrilase (SEQ ID NO: 40) comprising a single amino acid substitution at residue position 201 (Leu201➔Asn) of the *A. facilis* 72W nitrilase.

SEQ ID NO: 42 is the nucleotide sequence of an *A. facilis* 72W nitrilase mutant comprising a codon change which resulted in a single amino acid substitution at residue position 201 (L201S; Leu➔Ser).

SEQ ID NO: 43 is the deduced amino acid sequence of the mutant nitrilase (SEQ ID NO: 42) comprising a single amino acid substitution at residue position 201 (Leu201➔Ser) of the *A. facilis* 72W nitrilase.

SEQ ID NO: 44 is the nucleotide sequence of an *A. facilis* 72W nitrilase mutant comprising a codon change which resulted in a single amino acid substitution at residue position 168 (F168K; Phe➔Lys).

SEQ ID NO: 45 is the deduced amino acid sequence of the mutant nitrilase (SEQ ID NO: 44) comprising a single amino acid substitution at residue position 168 (Phe168➔Lys) of the *A. facilis* 72W nitrilase.

SEQ ID NO: 46 is the nucleotide sequence of an *A. facilis* 72W nitrilase mutant comprising a codon change which resulted in a single amino acid substitution at residue position 168 (F168M; Phe➔Met).

SEQ ID NO: 47 is the deduced amino acid sequence of the mutant nitrilase (SEQ ID NO. 46) comprising a single amino acid substitution at residue position 168 (Phe168➔Met) of the *A. facilis* 72W nitrilase.

SEQ ID NO: 48 is the nucleotide sequence of an *A. facilis* 72W nitrilase mutant comprising a codon change which resulted in a single amino acid substitution at residue position 168 (F168T; Phe➔Thr).

SEQ ID NO: 49 is the deduced amino acid sequence of the mutant nitrilase (SEQ ID NO: 48) comprising a single amino acid substitution at residue position 168 (Phe168➔Thr) of the *A. facilis* 72W nitrilase.

SEQ ID NO: 50 is the nucleotide sequence of an *A. facilis* 72W nitrilase mutant comprising a codon change which resulted in a single amino acid substitution at residue position 168 (F168V; Phe➔Val).

SEQ ID NO: 51 is the deduced amino acid sequence of the mutant nitrilase (SEQ ID NO:50) comprising a single amino acid substitution at residue position 168 (Phe168➔Val) of the *A. facilis* 72W nitrilase.

SEQ ID NO: 52 is the nucleotide sequence of an *A. facilis* 72W nitrilase mutant comprising a codon change which resulted in a single amino acid substitution at residue position 168 (T210A; Thr➔Ala).

SEQ ID NO: 53 is the deduced amino acid sequence of the mutant nitrilase (SEQ ID NO: 52) comprising a single amino acid substitution at residue position 210 (Thr210➔Ala) of the *A. facilis* 72W nitrilase.

SEQ ID NO: 54 is the nucleotide sequence of an *A. facilis* 72W nitrilase mutant comprising a codon change which resulted in a single amino acid substitution at residue position 168 (T210C; Thr➔Cys).

SEQ ID NO, 55 is the deduced amino acid sequence of the mutant nitrilase (SEQ ID NO: 54) comprising a single amino acid substitution at residue position 210 (Thr210➔Cys) of the *A. facilis* 72W nitrilase.

SEQ ID NO: 56 is the nucleotide sequence of the *A. facilis* 72W nitrilase expressed in *E. coli* strain SS1001 (ATCC PTA-1177).

SEQ ID NO: 57 is the deduced amino acid sequence of the mutant *A. facilis* 72W nitrilase expressed in *E. coli* SS1001 (ATCC PTA-1177).

BIOLOGICAL DEPOSITS

The following biological deposits have been made under the terms of the Budapest Treaty on the International Recognition of the Deposit of Microorganisms for the Purposes of Patent Procedure:

| Depositor Identification Reference | Int'l. Depository Designation | Date of Deposit |
|---|---|---|
| *Acidovorax facilis* 72W | ATCC 55746 | 8 Mar. 1996 |
| *E. coli* SS1001 | ATCC PTA-1177 | 11 Jan. 2000 |

As used herein, "ATCC" refers to the American Type Culture Collection International Depository Authority located at ATCC, 10801 University Blvd., Manassas, Va. 20110-2209, USA. The "International Depository Designation" is the accession number to the culture on deposit with ATCC.

The listed deposits will be maintained in the indicated international depository for at least thirty (30) years and will be made available to the public upon the grant of a patent disclosing it. The availability of a deposit does not constitute a license to practice the subject invention in derogation of patent rights granted by government action.

DETAILED DESCRIPTION OF THE INVENTION

A process is provided to stabilize and/or increase the specific activity of an enzyme catalyst having nitrilase activity when converting glycolonitrile to glycolic acid under suitable aqueous reaction conditions, wherein the reaction conditions includes an effective amount of at least one amine protectant.

Definitions

In this disclosure, a number of terms and abbreviations are used. The following definitions apply unless specifically stated otherwise.

As used herein, the term "comprising" means the presence of the stated features, integers, steps, or components as referred to in the claims, but that it does not preclude the presence or addition of one or more other features, integers, steps, components or groups thereof.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like.

The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value, preferably within 5% of the reported numerical value.

As used herein, the terms "amine protectant", "exogenously added amine protectant", and "protectant" are used interchangeably to refer to a compound included in the reaction mixture that is not naturally-produced, isolated, or a naturally a portion of the nitrilase catalyst, wherein the amine protectant comprises an effective amount of at least one primary amine group (R—$NH_2$) and/or secondary amine group (R—NH—$R_2$) wherein R and $R_1$ may be the same or different and wherein neither R or $R_2$ are carbonyl groups (i.e., the primary or secondary amine group is not part of an amide group). In a preferred embodiment, the amine protectant comprises an effective number of primary amine groups. In one embodiment, the amine protectant is elected from the group consisting of polyamine polymers and amine-functionalized materials including amine-functionalized support materials and amine-functionalized polymers.

As used herein, the term "effective amount of an amine protectant" or "effective amount of at least one amine protectant" will refer to an amount of the amine protectant that improves the nitrilase catalyst stability, specific activity, and/or catalytic productivity when converting glycolonitrile to glycolic acid (or the ammonium salt thereof. In one embodiment, the "effective amount of amine protectant" refers to the amount of amine protectant present in the reaction mixture that results in a measured increase in the catalyst's specific activity when compared to the specific activity of the same catalyst in the absence of the amine protectant under identical reaction conditions. It is known that an aqueous solution of glycolonitrile typically contains free formaldehyde and formaldehyde-derived impurities produced during the synthesis of glycolonitrile or generated as the result of glycolonitrile dissociation. It is understood that the amine protectant will have an "effective amount of free primary and/or secondary amine groups" capable of reacting with the formaldehyde or formaldehyde-derived impurities. By proviso, the amine protectant does not include compounds naturally produced by or naturally present in the nitrilase catalyst (for example, natural compounds produced by or within a whole cell catalyst or those found within a whole cell extract).

As used herein, the term "amine-functionalized" or "amine functionalized material" refers to a compound or material that has been chemically modified to have one or more primary and/or secondary amine groups. In one embodiment, the amine-functionalized material is selected from the group consisting of amine-functionalized support materials and amine-functionalized polymers. Means to chemically-functionalize compounds to contain one or more amine groups are well-known in the art (see, for example, Bickerstaff, G. F., *Immobilization of Enzymes and Cells, Methods in Biotechnology*, Volume 1. 1997. Humana Press, Totowa, N. J., and Wong, S. S., *Chemistry of Protein Conjugation and Crosslinking*, 1991. CRC Press, Boca Raton, Fla.).

As used herein, "amine-functionalized support materials" include, but are not limited to inorganic materials such as controlled pore glass and glass beads (e.g. aminopropylsilated glass beads), silica, magnetite, and alumina as well as support materials often used weakly basic anion exchange resins as well as ω-aminohexylagarose, ω-aminododecylagarose, and ω-aminoethylagarose. In one embodiment, the amine-functionalized material comprises polyethylenimine (i.e. "a polyethylenimine-functionalized material").

As used herein, the term "amine-functionalized polymers" refers to polymers that have been modified to include one or more primary and/or secondary amine groups. Typically, the non-functionalized polymer does not normally contain an effective number of free amine groups.

As used herein, the terms "free amine group" refers to a primary amine group (R—$NH_2$) and/or a secondary amine group (R—NH—$R_2$) on the amine protectant that is capable of reacting with formaldehyde.

As used herein, the term "polyamine polymers" refers to polymers comprising one or more free amine groups. Polyamine polymers are prepared from at least one monomer comprising at least one primary and/or at least one secondary amine group. In one embodiment, the polyamine polymers include copolymers comprising at least one free amine group. Polyamine polymers may range in size from oligomers (typically less than 1,000 Daltons) to higher molecule weight polymers ranging from 1,000 Daltons to 10,000,000 Daltons, preferably from 1,000 Daltons to 2,000,000 Daltons, more preferably 1,000 Daltons to 1,000,000 Daltons, and more preferably from 10,000 Daltons to 1,000,000 Daltons.

As used herein, the term "glycolonitrile" is abbreviated as "GLN" and is synonymous with hydroxyacetonitrile, 2-hydroxyacetonitrile, hydroxymethylnitrile, and all other synonyms of CAS Registry Number 107-164.

As used herein, the term "glycolic acid" is abbreviated as 'GLA' and is synonymous with hydroxyacetic acid, hydroxyethanoic acid, and all other synonyms of CAS Registry Number 79-14-1. The glycolic acid produced by the present processes may in the form of the protonated carboxylic acid and/or the corresponding ammonium salt.

As used herein, the term 'ammonium glycolate' is abbreviated "$NH_4GLA$".

As used herein, the term "glycolamide" is the amide derived from the reaction of ammonia with glycolic acid and refers to all other synonyms of compounds having CAS Registry Number 598-42-5.

As used herein, the term "glycolide" refers to the compound of CAS Registry Number 502-97-6.

As used herein, the term "formaldehyde" is abbreviated as "FA" and is synonymous with formic aldehyde, methyl aldehyde, oxomethane, and all other synonyms of CAS Registry Number 50-00-0. Commercially available formaldehyde is typically comprised of a mixture of monomeric formaldehyde ("free formaldehyde") and various oligomers of formaldehyde along with some methanol (typically about 1 wt % to about 15 wt %).

As used herein, the term "hydrogen cyanide" is synonymous with prussic acid, hydrocyanic acid, and all other synonyms of CAS Registry Number 200-821-6.

As used herein, the term "recovering" means isolating, purifying, or transferring the product formed by the present process. Methods to isolate and purify the product(s) from the reaction mixture are well known in the art may include, but are not limited to selective precipitation, crystallization, filtration, reactive solvent extraction, ion exchange, electrodialysis, polymerization, distillation, thermal decomposition, alcoholysis, column chromatography, and combinations thereof. In one embodiment, the term "recovering" may also include transferring the product mixture (typically after filtering out the enzyme catalyst) to another reaction to create one or more additional products. In a preferred embodiment, ion exchange is used to recover the glycolic acid.

As used herein, the terms "enzyme catalyst", "nitrilase catalyst" or "microbial cell catalyst" refers to a catalyst that is characterized by a nitrilase activity (i.e., comprises at least one polypeptide having nitrilase activity) for converting glycolonitrile to glycolic acid and ammonia. A nitrilase enzyme directly converts a nitrile (preferably, an aliphatic nitrile) to the corresponding carboxylic acid, without forming the corresponding amide as intermediate (see Equation 1). Nitrilases share several conserved signature domains known in the art including a signature domain herein referred to as the "catalytic signature sequence" or "signature sequence". This region comprises an essential cysteine residue (e.g., $Cys_{164}$ of SEQ ID NO: 4). As such, polypeptides having nitrilase activity can be identified by the existence of the catalytic domain signature sequence (SEQ ID NO: 1). In a preferred embodiment, the signature sequence is SEQ ID NO: 2. The enzyme catalyst may be in the form of a whole microbial cell, permeabilized microbial cell(s), one or more cell components of a microbial cell extract, partially purified enzyme, or purified enzyme. The enzyme catalyst can be free (unimmobilized) or immobilized in or on a soluble or insoluble support. As used herein, "recycled enzyme catalyst" refers to an enzyme catalyst that is reused as an enzyme catalyst in batch reactions. In a preferred embodiment, the enzyme catalyst is a transformed microbial host cell recombinantly expressing at least one enzyme having nitrilase activity; wherein said enzyme comprises the catalytic signature motif of SEQ ID NO: 1 or SEQ ID NO: 2.

As used herein, the terms "*Acidovorax facilis*" and "*A. facilis*" are used interchangeably and refer to *Acidovorax facilis* 72W deposited to the American Type Culture Collection (an international depository authority) having accession number 55746 ("ATCC 55746"). The mutant nitrilases derived from *A. facilis* 72W characterized by improved nitrilase activity when converting glycolonitrile to glycolic acid have been previously reported (see co-owned U.S. Pat. No. 7,198,927). Examples of these *A. facilis* 72W-derived mutant nitrilases are provide by SEQ ID NOs: 27, 29, 31, 33, 35, 37, 39, 41, 43, 45, 47, 49, 51, 53, and 55.

As used herein, the terms "*Escherichia coli*" and "*E. coli*" are used interchangeably. Several strains of *E. coli* suitable for recombinant expression are described herein including, but not limited to *E. coli* MG1655 having international depository number ATCC 47076, *E. coli* FM5 having international depository number ATCC 53911, *E. Coli* W3110 having international depository number ATCC 27325, *E. coli* MC4100 having international depository number ATCC 35695, and *E. coli* W1485 having international depository number ATCC 12435, In one embodiment, suitable *Escherichia coli* strains include *E. coli* FM5 (ATCC 53911) and *E. coli* MG1655 (ATCC 47076).

As used herein, the terms "*E. coli* SS1001" or "SS1001" refer to a transformed *E. coli* strain expressing the *Acidovorax facilis* 72W nitrilase having ATCC Accession No. PTA-1177 (see U.S. Pat. No. 6,870,038; herein incorporated in its entirety by reference). The recombinantly expressed *E. coli* SS81001 nitrilase (SEQ ID NO: 57) contains 2 minor sequence changes in comparison to the wild-type 72W nitrilase sequence (SEQ ID NO: 4). The start codon was changed from GTG to ATG to facilitate recombinant expression and an artifact was introduced during cloning that resulted in a single amino acid change near the C-terminal (Pro367 [CCA]→Ser [TCA]).

As used herein, the terms "suitable aqueous glycolonitrile reaction mixture", "suitable aqueous reaction mixture", and "suitable reaction conditions" refer to the materials (including at least one amine protectant) and reaction conditions under which the present process is conducted. The components of the suitable aqueous reaction mixture are provided herein and those skilled in the art appreciate the range of component variations suitable for this process.

As used herein, the terms "aqueous ammonium glycolate solution", "aqueous solution comprising ammonium glycolate", and "aqueous solution of ammonium glycolate" will be used to describe an aqueous solution comprising ammonium glycolate produced by the enzymatic hydrolysis of glycolonitrile under typical enzymatic reaction conditions (i.e., a pH range of about 6 to about 8). The aqueous solution of ammonium glycolate comprises ammonium glycolate at a concentration of at least about 0.1 weight percent (wt %) to about 99 wt % ammonium glycolate. In another embodiment, the aqueous solution of ammonium glycolate is comprised of at least about 10 wt % to about 75 wt % ammonium glycolate. In a further embodiment, the aqueous solution of ammonium glycolate is comprised of at least about 20 wt % to about 50 wt % ammonium glycolate. The pH of the aqueous solution of ammonium glycolate can be about 2 to about 12, preferably 5 to about 10, more preferably 6 to about 8. The pH may be adjusted as needed prior to initiating process steps related to recovering glycolic acid (in the form of the acid or salt) from the aqueous ammonium glycolate solution.

As used herein, the terms "catalyst productivity" and "enzyme catalyst productivity" refer to the total amount of product produced per gram of catalyst. In the present process, the catalyst comprises a nitrilase enzyme (EC 3.5.5.7) and the product formed is glycolic acid and/or ammonium glycolate (depending upon the pH of the reaction). In general, the present methods are conducted under essentially pH neutral conditions so that the glycolic acid produced is predominantly in the form of the corresponding salt of glycolic acid (i.e. ammonium glycolate). Generally, in batch reactions with catalyst recycle, the catalyst activity decreases with each recycle reaction (enzyme inactivation). As shown in Example 6, and in one embodiment, the specific activity of the catalyst is increased over multiple recycle reactions, resulting in an increase in catalyst productivity.

The terms "catalyst specific activity", "specific activity", and "nitrilase specific activity" refers to the enzyme activity per unit mass (for example, milligram) of protein, dry cell weight, or bead weight (immobilized catalyst) when converting glycolonitrile to glycolic acid (or the corresponding ammonium glycolate). Comparisons in nitrilase activity were measured proportional to the dry cell weight or bead weight. Since the same catalyst and expression system was used to compare the specific activity between reactions with or without (i.e. the control) the amine protectant, comparisons and reported improvements/increases in nitrilase specific activity were measured relative to dry cell weight (dcw) or bead weight (bw). As used herein, the term "improved catalyst specific activity", and "improved specific activity" refers to the increase in specific activity observed relative to the specific activity of the corresponding control. The improvement in specific activity is measured under identical reaction conditions wherein the only different is the inclusion or omission of the amine protectant. In one embodiment, the improvement in specific activity is measured over multiple recycle reactions. In another embodiment, the improvement or increase in catalyst specific activity using the present process is increased at least 1%, preferably at least 5%, more preferably at least 10%, even more preferably at least 25%.

As used herein, the term "one unit of enzyme activity" or "one unit of nitrilase activity" or "U" is defined as the amount of enzyme activity required for the production of 1 µmol of glycolic acid product per minute (GLA U/g dry cell weight or bead weight) at a specified temperature (e.g. 25° C.).

As used herein, the terms "recombinant organism", "transformed host cell", "host cell", "transformant", "transgenic organism", and "transformed microbial host" refer to a host organism having been transformed with heterologous or foreign DNA. The recombinant organisms of the present invention express foreign coding sequences or genes that encode active nitrilase enzyme. "Transformation" refers to the transfer of a DNA fragment into the host organism. The transferred DNA fragment can be chromosomally or extrachromosomally incorporated (i.e., via a vector) into the host organism. As used herein, the term "transformation cassette" refers to a specific fragment of DNA containing a set of genetic elements conveniently arranged for insertion into a host cell, usually as part of a plasmid. As used herein, the term "expression cassette" refers to a specific fragment of DNA containing a set of genetic elements conveniently arranged for insertion into a host cell, usually as part of a plasmid, which also allows for enhanced gene expression in the host.

As used herein, the terms "nucleic acid fragment" and "nucleic acid molecule" refer to DNA molecule that may encode an entire gene, coding sequence, and/or regulatory sequences preceding (5', upstream) or following (3', downstream) the coding sequence. In one aspect, the present nucleic acid molecules encode for polypeptides having nitrilase activity.

As used herein, the term "gene" refers to a nucleic acid molecule that expresses a specific protein. As used herein, it may or may not including regulatory sequences preceding (5' non-coding sequences) and following (3' non-coding sequences) the coding sequence. 'Chimeric gene' refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

As used herein, the term "coding sequence" refers to a DNA sequence that codes for a specific amino acid sequence.

As used herein, 'suitable regulatory sequences' refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing sites, effector binding sites, and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. Promoters that cause a gene to be expressed in most cell types at most times or under most environmental conditions are commonly referred to as "constitutive promoters". Promoters that cause a gene to be expressed only in the presence of a particular compound or environmental condition are commonly referred to as "inducible promoters". Since in most cases the exact boundaries of regulatory sequences have not been completely defined, DNA fragments of different lengths may have identical promoter activity.

As used herein, the term "operably linked" refers to the association of nucleic acid sequences on a single nucleic acid molecule so that the function of one sequence is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

As used herein, the term "3' non-coding sequences" refers to DNA sequences located downstream of a coding sequence and include polyadenylation recognition sequences (normally limited to eukaryotes) and other sequences encoding regulatory signals capable of affecting mRNA processing or gene expression. The polyadenylation signal (normally limited to eukaryotes) is usually characterized by affecting the addition of polyadenylic acid tracts to the 3' end of the mRNA precursor.

The skilled artisan is well aware of the "codon-bias" exhibited by a specific host cell in using nucleotide codons to specify a given amino acid. Therefore, when synthesizing a gene for improved expression in a host cell, it is desirable to design the gene such that its codon usage reflects the preferred codon bias of the host cell. A survey of genes derived from the host cell where sequence information is available can determine its codon bias. Codon-optimization is well known in the art and has been described for various systems including, but not limited to yeast (Outchkourov et al, *Protein Expr Purif*, 24(1):18-24 (2002)) and *E. coli* (Feng et al., *Biochemistry*, 39(50):15399-15409 (2000)).

Nitrilase Catalysts

All nitrilases (EC 3.5.5.7) share a conserved catalytic triad (Glu, Lys, and Cys) (Chauhan et al., *Appl. Microbiol. Biotechnol.* 61:118-122 (2003); Pace, H. and Brenner, C., *Genome Biol.* 2(1):reviews 0001.1-0001.9 (2001)). All known nitrilases have a nucleophilic cysteine in the enzyme active site (Cowan et al., *Extremophiles*, 2.207-216 (1998); Pace, H. and Brenner, C., supra; and Chauhan et al, supra) and all are susceptible to inactivation by thiol reagents (1.0 mM concentrations of copper chloride, silver nitrate, mercuric acetate, or ferric chloride each produced major decreases in *A*.

facilis 72W nitrilase enzyme activity). Cysteine residues are also capable of being irreversibly oxidized to sulfinic acids, resulting in a loss of enzyme activity. Despite the sensitivity of nitrilase enzymes to various inactivating mechanisms, immobilized *A. facilis* 72W cells are robust, capable of retaining much of their nitrilase activity after numerous recycle reactions (U.S. Pat. No. 6,870,038; U.S. Pat. No. 7,148,051; U.S. Pat. No. 7,198,927; and Chauhan et al., supra). Nitrilase catalysts derived from the *A. facilis* 72W nitrilase also been shown to catalyze the conversion of α-hydroxynitriles (i.e., glycolonitrile) to α-hydroxycarboxylic acids (i.e., glycolic acid) (see U.S. Pat. No. 6,383,786; U.S. Pat. No. 6,416,980; and U.S. Pat. No. 7,198,927).

Sequence comparisons of the *A. facilis* 72W nitrilase to other bacterial nitrilases have been reported (U.S. Pat. No. 6,870,038; Chauhan et al., supra). The 72W nitrilase has several conserved signature domains including a 16-amino acid region near the amino terminus (amino acid residues 40-55 of SEQ ID NO: 4) and a 12 amino acid catalytic region (amino acid residues 160-171 of SEQ ID NO: 4) containing the essential cysteine residue. This essential cysteine residue ($Cys_{164}$ of SEQ ID NO: 4), along with conserved glutamic acid ($Glu_{48}$ of SEQ ID NO:4) and lysine residues ($Lys_{130}$ of SEQ ID NO:4), form the catalytic triad motif found in all nitrilases (Pace, H., and Brenner, C., supra).

The regions surrounding each of the catalytic triad residues are highly conserved, especially the region surrounding the catalytic cysteine residue. The essential catalytic cysteine residue is located with a highly conserved region referred to as the "catalytic signature motif" or "signature motif". As such, the present process is useful for protecting the enzymatic activity of any nitrilase comprising the catalytic signature motif defined by Formula 1 (bold indicates strictly conserved amino acid residues, italicized residues are those that exhibit minimal variability [i.e., minimal variation of 3 or fewer amino acid residues], the catalytic cysteine residue is underlined):

Formula 1
(SEQ ID NO: 1)
Gly-$Xaa_1$-$Xaa_2$-$Xaa_3$-<u>Cys</u>-Trp-Glu-$Xaa_4$-$Xaa_5$-$Xaa_6$-$Xaa_7$-$Xaa_8$.

wherein
$Xaa_1$=Ala or Gly;
$Xaa_2$=Leu, Val, or Ala;
$Xaa_3$=Ala, Asn, Ile, Cys, Val, or Gln;
$Xaa_4$=His or Asn;
$Xaa_5$=Leu, Tyr, Phe, Ala, Met, Lys, Val, Thr, or Arg;
$Xaa_6$=Asn, Gln, Met, Leu, or Ser;
$Xaa_7$=Pro or Thr; and
$Xaa_8$=Leu or Val.

In a preferred embodiment, the nitrilase signature motif of Formula 1 is $Xaa_1$=Ala or Gly; $Xaa_2$=Leu; $Xaa_3$=Ala, Asn, Ile, Cys, Val, or Gln; $Xaa_4$=His; $Xaa_4$=Leu, Tyr, Phe, Ala, Met, Lys, Val, Thr or Arg; $Xaa_6$=Ser, Gln, Asn, or Met; $Xaa_7$=Pro; and $Xaa_8$=Leu; resulting in the catalytic signature motif represented by the following:

(SEQ ID NO: 2)
Gly-$Xaa_1$-Leu-$Xaa_3$-Cys-Trp-Glu-His-$Xaa_5$-$Xaa_6$-Pro-Leu

Examples of nitrilases, including the sequences and position of the corresponding catalytic signature motif sequence, are provided in Table 1.

TABLE 1

Conserved Catalytic Cysteine Region-Catalytic Signature Motifs

| Nitrilase Source | GenBank® Accession Number | Amino Acid SEQ ID NO. | Sequence of Signature Motif (amino acid residue positions) |
|---|---|---|---|
| *Acidovorax Facilis* 72W | ABD98457.1 | 4 | GGLNCWEHFQPL (160-171) |
| *Alcaligenes faecalis* JM3 | BAA02684.1 | 5 | GALCCWEHLSPL (159-170) |
| *Rhodococcus rhodochrous* J1 | Q03217 | 6 | GALNCWEHFQTL (161-172) |
| *Rhodococcus rhodochrous* K22 | Q02068 | 7 | GGLNCWEHFQPL (166-177) |
| *Nocardia* sp. C-14-1 | AAX18182.1 | 8 | GGLNCWEHFQPL (154-165) |
| *Bordetella bronchiseptica* RB50 | NP_867662.1 | 9 | GAVVCWENYMPL (161-172) |
| *Arabidopsis thaliana* | AAB60275.1 AAA19627.1 | 10 | GAAICWENRMPL (175-186) |
| *Synechococcus elongatus* PCC 7942 | YP_399857.1 | 11 | GALACWEHYNPL (157-168) |
| *Synechococcus elongatus* PCC 6301 | YP_171411.1 | 12 | GALACWEHYNPL (157-168) |
| *Synechocystis* sp. PCC 6803 | NP_442646.1 | 13 | GALACWEHYNPL (165-176) |

TABLE 1-continued

Conserved Catalytic Cysteine Region-
Catalytic Signature Motifs

| Nitrilase Source | GenBank ® Accession Number | Amino Acid SEQ ID NO. | Sequence of Signature Motif (amino acid residue positions) |
|---|---|---|---|
| Pseudomonas entomophila L48 | YP_6090481.1 | 14 | GAAVCWENYMPL (161-172) |
| Zymomonas moblis | YP_162942.1 | 15 | GAAICWENYMPV (161-172) |
| Bacillus sp. OxB-1 | BAA90460.1 | 16 | GGLQCWEHFLPL (158-169) |
| Comamonas testosteroni | AAA82085.1 | 17 | GGLQCWEHALPL (159-170) |
| Synechococcus sp. CC9605 | YP_381420.1 | 18 | GALACWEHYNPL (156-167) |
| Pseudomonas fluorescens Pf-5 | YP_260015.1 | 19 | GAVICWENMMPL (161-172) |
| Nocardia farcinica IFM 10152 | YP_119480.1 | 20 | GALCCWEHLQPL (159-170) |
| Alcaligenes faecalis 1650 | AAY06506.1 | 21 | GALCCWEHLSPL (159-170) |
| Pseudomonas syringae pv. syringae B728a | AAY35081.1 | 22 | GALCCWEHLQPL (157-168) |
| Bradyrhizobium sp. BTAiI | ZP_00859948.1 | 23 | GALCCWEHLQPL (163-174) |
| Rhodococcus rhodochrous NCIMB 11216 | CAC88237 | 24 | GALNCWEHFQTL (161-172) |
| Rhodococcus rhodochrous ATCC 30494 ™ | N/A | 25 | GALNCWEHFQTL (161-172) |

In one embodiment, the nitrilase catalyst comprises a polypeptide having nitrilase activity isolated from a genera selected from the group consisting of *Acidovorax, Rhodococcus, Nocardia, Bacillus,* and *Alcaligenes.* In one embodiment, the nitrilase catalyst comprises a polypeptide having nitrilase activity isolated from a genera selected from the group consisting of *Acidovorax* and *Rhodococcus.*

In another embodiment, the polypeptide having nitrilase activity is derived from *Acidovorax facilis* 72W (ATCC 55746) or a polypeptide (having nitrilase activity) that is substantially similar to the *Acidovorax facilis* 72W nitrilase (SEQ ID NO: 4) or the *A. facilis* 72W derived enzyme represented by SEQ ID NO: 51.

In one embodiment, the nitrilase catalyst is a microbial host cell transformed to express at least one polypeptide having nitrilase activity. In one embodiment the transformed host cell is selected from the group consisting of *Comamonas* sp., *Corynebacterium* sp., *Brevibacterium* sp., *Rhodococcus* sp., *Azotobacter* sp., *Citrobacter* sp., *Enterobacter* sp., *Clostridium* sp., *Klebsiella* sp., *Salmonella* sp., *Lactobacillus* sp., *Aspergillus* sp., *Saccharomyces* sp., *Yarrowia* sp., *Zygosaccharomyces* sp., *Pichia* sp., *Kluyveromyces* sp., *Candida* sp., *Hansenula* sp., *Dunaliella* sp., *Debaryomyces* sp., *Mucor* sp., *Torulopsis* sp., *Methylobacteria* sp., *Bacillus* sp., *Escherichia* sp., *Pseudomonas* sp., *Rhizobium* sp., and *Streptomyces* sp. In a preferred embodiment, the microbial host cell is selected from the group consisting of *Bacillus* sp., *Pseudomonas* sp., and *Escherichia* sp. In a preferred embodiment, the catalyst is an *Escherichia coli* host cell recombinantly expressing one or more of the polypeptides having nitrilase activity.

In another embodiment, the nitrilase catalyst comprises a polypeptide having nitrilase activity wherein said polypeptide having nitrilase activity has at least 60% identity to SEQ ID NO: 51, preferably at least 70% identity to SEQ ID NO: 51, even more preferably at least 80% identity to SEQ ID NO: 51, yet even more preferably at least 90% identity to SEQ ID NO: 51, and most preferably at least 95% identity to SEQ ID NO: 51.

Working examples of several catalysts having nitrilase activity derived from various sources are described herein, including a catalyst derived from the *A. facilis* 72W nitrilase. Various mutants derived from the *Acidovorax facilis* 72W nitrilase enzyme have been reported in the art (U.S. Pat. No. 7,148,051 and U.S. Pat. No. 7,198,927).

In one embodiment, the polypeptide having nitrilase activity is selected from the group consisting of SEQ ID NOs: 4, 5, 6, 7, 8, 9, 10, 11, 12, 13, 14, 15, 16, 17, 18, 19, 20, 21, 22, 23, 24, 25, 27, 29, 31, 33, 35, 37, 39, 41, 43, 45, 47, 49, 51, 53, 55, and 57. In another embodiment, the polypeptide having nitrlase activity is selected from the group consisting of 4, 24, 25, 27, 29, 31, 33, 35, 37, 39, 41, 43, 45, 47, 49, 51, 53, 55, and 57. In another embodiment, the polypeptide having nitrilase activity is selected from the group consisting of 4, 27, 29, 31, 33, 35, 37, 39, 41, 43, 45, 47, 49, 51, 53, 55, and 57. In another embodiment, the polypeptide having nitrilase activity is selected from the group consisting of 4, 24, 25, and 51. In another embodiment, the nitrilase catalyst comprises the polypeptide of SEQ ID NO: 51.

Amine Protectants

The amine protectant is any compound exogenously added to the aqueous reaction mixture (e.g., not naturally produced by, naturally found with, or naturally isolated from the enzyme catalyst) comprising at least one primary amine group (R—$NH_2$) and/or secondary amine group (R—NH—$R_2$) capable of reacting with formaldehyde wherein R and $R_1$ may be the same or different and wherein neither R or $R_2$ are carbonyl groups (i.e. not an amide group). It is also understood that the present enzyme catalyst hydrolyzes nitrile groups, and thus, the amine protectant preferably does not include a nitrile group capable of being hydrolyzed by a nitrilase catalyst. In a preferred embodiment, the amine protectant is an exogenously added compound or component in the reaction mixture comprising at least one primary amine group.

In one embodiment of the present invention, an effective amount of at least one amine protectant is added to the reaction mixture. As used herein, "an effective amount of an amine protectant" is the amount of amine protectant necessary to result in a detectable improvement in catalyst specific activity, stability, or catalytic productivity when enzymatically converting glycolonitrile to glycolic acid. It is well within the skill of one in the art to adjust the amount of amine protectant in the aqueous reaction mixture in order to achieve the desired effect. In one aspect, the amount of amine protectant added to the reaction mixture comprises a molar excess of free amine groups relative to the amount of formaldehyde present in the reaction mixture. In one aspect, the reaction mixture comprises at least 0.01 ppm formaldehyde. In another aspect, the amount of amine protectant in the reaction mixture comprises a molar ratio of free amine groups (primary, secondary, or a combination thereof) relative to the amount of free formaldehyde (HCHO) present in the reaction mixture ranging from 0.001:1.0 to 1.0:0.001, preferably at least 0.5:1.0.

In one aspect, the amine protectant is selected from the group consisting of:

a) a compound of the formula

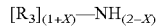

wherein X is 0 or 1 and $R_3$ is independently C1 to C20 hydrocarbyl group or substituted hydrocarbyl group, wherein $R_3$ is optionally comprising one or more ether linkages with the proviso that (i) the substituted group is preferably not a cyano group capable of reacting with the nitrilase catalyst, and (ii) $R_3$ is not a carbonyl group, b) a polyamine polymer comprising an effective number of free amine groups; and c) an amine-functionalized material comprising an effective number of free amine groups;

wherein the amine protectant is not naturally-produced by the enzyme catalyst.

The hydrocarbyl group of $R_3$ can be linear, branched, cyclic, polycyclic, or aromatic. As used herein, the terms "hydrocarbyl", "hydrocarbyl group", and "hydrocarbyl moiety" is meant a straight chain, branched or cyclic arrangement of carbon atoms connected by single, double, or triple carbon to carbon bonds and/or by ether linkages, and substituted accordingly with hydrogen atoms. Such hydrocarbyl groups may be aliphatic and/or aromatic. Examples of hydrocarbyl groups include methyl, ethyl, propyl, isopropyl, butyl, isobutyl, t-butyl, cyclopropyl, cyclobutyl, pentyl, cyclopentyl, methylcyclopentyl, hexyl, cyclohexyl, benzyl, and phenyl. In a preferred embodiment, the hydrocarbyl moiety is a straight chain, branched or cyclic arrangement of carbon atoms connected by single carbon to carbon bonds and/or by ether linkages, and substituted accordingly with hydrogen atoms. As used herein, "substituted hydrocarbyl" means a group that is substituted and contains one or more substituent groups that do not cause the substrate, catalyst, or product to be unstable or unsuitable for the use or reaction intended. Substituent groups which are generally useful include ether, ester, halo, amino (including primary, secondary and tertiary amine groups), hydroxy, vinylidene or substituted vinylidene, silyl or substituted silyl, nitro, nitroso, sulfinyl, sulfonyl, sulfonic acid alkali metal salt, boranyl or substituted boranyl, and thioether.

In one embodiment, the amine protectant is a polyamine polymer comprising an effective number of free amine groups. In another embodiment, polyamine polymers include copolymers comprising an effective number of free amine groups Polyamine polymers may range in size from oligomers (typically less than 1,000 Daltons) to higher molecule weight polymers ranging from 1,000 Daltons to 101000,000 Daltons, preferably from 11000 Daltons to 2,000,000 Daltons, more preferably 1,000 Daltons to 1,000,000 Daltons, and more preferably from 10,000 Daltons to 1,000,000 Daltons.

In one embodiment, the polyamine polymer is selected from the group consisting of 2-amino-2-deoxy-(1→4)-β-D-glucopyranan (i.e. chitosan), polyalkyleneamine polymers having alkylene moieties of 2 to 12 carbon atoms, polyethylenimine, polyallylamine, polyvinyl alcohol/polyvinylamine copolymers, D-polylysine, L-polylysine, mixtures of D/L polylysine, polyethylenimine cross-linked with glutaraldehyde, and mixtures thereof. In a preferred embodiment, the polyamine polymer is polyethyleneimine polymer (linear or branched) and copolymers comprising polyethylenimine. In another preferred embodiment, the polyamine polymer is polyethylenimine cross-linked with glutaraldehyde. In a further preferred embodiment, the enzyme catalyst is immobilized in or on a particle or bead comprising polyethylenimine cross-linked with glutaraldehyde.

The amine protectant may be soluble or insoluble in the aqueous reaction mixture. Soluble amine protectants can be separated from the subsequent product mixture using any number of separation methodologies well known in the art (for example, ion exchange or chromatographic techniques). Depending upon the chemical nature of the soluble amine protectant, one of skill in the art may separate the amine protectant from the glycolic acid (or ammonium glycolate) product by adjusting the post reaction processing conditions to selectively precipitate or adsorb one or more components from the product mixture. For certain applications, it may not be necessary to remove the soluble amine protectant from the product mixture, especially for applications where high purity glycolic acid and/or ammonium glycolate is not required.

In a preferred embodiment, the amine protectant is substantially insoluble in the aqueous reaction mixture. The use of an insoluble amine protectant facilitates simple separation/isolation (i.e. filtration, centrifugation, etc.) from the resulting aqueous product mixture. In another preferred embodiment the amine protectant is a polyamine polymer that is insoluble in the aqueous reaction mixture.

In another embodiment, the amine protectant is an insoluble amine-functionalized material and may include amine-functionalized support materials and amine-functionalized polymers. Methods to chemically modify insoluble materials to include at least one primary amino group are well-known in the art (for example, see Bickerstaff, G. F., *Immobilization of Enzymes and Cells, Methods in Biotechnology*, Volume 1. 1997. Humana Press, Totowa, N.J., and Wong, S. S., *Chemistry of Protein Conjugation and Crosslinking*, 1991. CRC Press, Boca Raton, Fla.).

The amine-functionalized material comprising an effective number of free amine groups (or functionalized to contain an effective number free amine groups) useful in the present process may include, but is not limited to polysaccharides that have been chemically functionalized to contain one or more amino groups (for example, amine-functionalized glycans, agarose, carrageenan, alginate, dextran, and cellulose), methacrylates, polyurethanes, polyesters, nylons, alumina, silica, polystyrene, polyvinyl alcohols, magnetite, and controlled pore glass. Polyalkyleneamine polymers (typically having alkylene moieties of 2 to 12 carbon atoms) and polyalkyleneamine-functionalized support materials may be used, as may soluble or insoluble polyethyleneamine polymers, polyethyleneamine-functionalized supports materials, polyethylenimine, polyethylenimine polymers (linear or branched), polyethylenimine cross-linked with glutaraldehyde, polyethylenimine ion exchange resins, weakly basic anion exchange resins (for example, AMBERLITE® weakly basic anion exchange resins IRA-95, IRA-96, IRA-67, and IRA-92 (available from Rohm and Haas, Philadelphia, Pa.), and DIAION® WA20 or WA21J (available from Mitsubishi Chemical, Tokyo, Japan), polyethylenimine-cellulose, polyethyleneimine-silica, polyallylamine, polyvinyl alcohol/polyvinylamine copolymers, polylysine (D, L, or D/L mixtures), ω-aminohexylagarose, ω-aminododecylagarose, ω-aminoethylagarose, aminopropylsilated glass beads, and combinations thereof. In a preferred embodiment, the amine protectant does not include a cyano group capable of being hydrolyzed by the nitrilase catalyst.

In one embodiment, amino alkyl-, amino(hydroxyalkyl)-, aminoalkyl-ether-, and amino(hydroxyalkyl)-ether derivatives of cellulose, chitin and other naturally-occurring carbohydrates are preferably selected from the group consisting of:

$H_2N—(CH_2)_n$-[carbohydrate] where n=1-10, including alkyl isomers, $H_2N—(CH_2)_m—CHOH—(CH_2)_n$-[carbohydrate], where m=0-10 and n=0-10, $H_2N—(CH_2)_n$—O-[carbohydrate] where n=1-10, and $H_2N—(CH_2)_m—CHOH—(CH_2)_n$—O-[carbohydrate] where m=0-10 and n=0-10.

In another embodiment, aminophenyl or aminobenzyl derivatives of cellulose, chitin or other naturally occurring carbohydrates are preferably selected from the group consisting of:

$H_2N—C_6H_4—(CH_2)_n$-[carbohydrate], $H_2N—CH_2—C_6H_4—(CH_2)_n$-[carbohydrate]

$H_2N—C_6H_4—(CH_2)$, —O—[carbohydrate] where n=0-10, and $H_2N—C_6H_4—(CH_2)_m—CHOH—(CH_2)_n$—[carbohydrate], wherein m=0-10 and n=0-10, including p-, o- and m-benzene ring amino-isomers, aminomethyl-isomers and alkyl group isomers thereof.

Amine-functionalized materials may additionally be prepared as mixed polysaccharide-polymeric derivatives wherein primary amine/aminoalkyl (one to ten carbons per alkyl group), aminohydroxyalkyl (one to ten carbons per alkyl group and one to ten hydroxyl groups per alkyl group), aminobenzene and/or aminoalkylbenzene (one to ten carbons per alkyl group) functional groups are covalently attached to matrices such as epichlorohydrin copolymers of cellulose or chitin and wherein hydrocarbon spacer groups may include alkene as well as alkyl groups.

Non-polysaccharide polymeric derivatives wherein primary amine, aminoalkyl (one to ten carbons per alkyl group), aminohydroxyalkyl (one to ten carbons per alkyl group and one to ten hydroxyl groups per alkyl group), aminobenzene and/or aminoalkylbenzene (one to ten carbons per alkyl group) functional groups are covalently attached to any one of a wide variety of synthetic polymers including polystyrene, styrene-divinylbenzene copolymer, polyvinyl alcohol and cross-linked derivatives thereof, and wherein hydrocarbon spacer groups may include alkene as well as alkyl groups.

In another embodiment, the enzyme catalyst is immobilized in a matrix comprising at least one amine protectant. In another embodiment the enzyme catalyst is immobilized in an insoluble matrix comprising an effective number of free amine groups. In a preferred embodiment, the insoluble matrix provides and effective number of primary amine groups (i.e. carrageenan beads crosslinked with glutaraldehyde and polyethylenimine).

In those applications where an insoluble amine protectant additive need not be removed from the final product, or where said additive is readily removed from the product mixture (for instance by ion exchange or distillation), then soluble amine protectants may be used. Examples of soluble amine protectants may include, but are not limited to soluble forms of the above mentioned insoluble polymers (e.g., soluble low molecular monomers), $C_1$-$C_{12}$ aliphatic, cycloaliphatic, or aromatic compounds comprising one or more primary amino groups, 1-amino-2-ethanol, 1-amino-2-propanol, Tris buffer, ethylenediamine and similar soluble amine protectants comprising at least one primary amino group.

In a preferred embodiment, the amine protectant is polyethylenimine. In a further preferred embodiment, the nitrilase catalyst is immobilized in an insoluble matrix crosslinked with glutaraldehyde and polyethylenimine.

One of skill in the art can adjust the amount of amine protectant in the reaction mixture to achieve the desired effect (i.e. an improved in nitrilase activity; also referred to herein as an "effective amount"). In one embodiment, the concentration of amine protectant is at least 0.01 mg/mL, preferably at least 0.1 mg/L, more preferably at least 1 mg/mL, and most preferably at least 5 mg/mL.

Hydrolysis of Glycolonitrile to Glycolic Acid Using a Nitrilase Catalyst

The enzymatic conversion of glycolonitrile to glycolic acid (in the form of the acid and/or the corresponding ammonium salt) was performed by contacting an enzyme catalyst (comprising a polypeptide having nitrilase activity) with a suitable aqueous reaction mixture comprising glycolonitrile using a suitable set of enzymatic reaction conditions (pH range, temperatures, concentrations, etc.) described below. In one embodiment, whole recombinant microbial cells can be used as an enzyme catalyst without any pretreatment. In another embodiment, the microbial cell catalyst can be added directly to a reaction mixture, or maintained separately from the bulk reaction mixture using hollow-fiber membrane cartridges or ultrafiltration membranes. In a further embodiment the microbial cells can be immobilized in a polymer matrix (e.g., carrageenan or polyacrylamide gel (PAG) particles) or on an insoluble solid support (e.g., celite) to facilitate recovery and reuse of the enzyme catalyst (U.S. Pat. No. 6,870,038; herein incorporated by reference). In yet a further embodiment, purified or partially-purified enzyme(s) can also be isolated from the whole cells and used directly as a catalyst, or the enzyme(s) can be immobilized in a polymer matrix or on an insoluble support. Methods for the immobilization of cells or for the isolated enzymes have been widely reported and are well known to those skilled in the art (Methods in Biotechnology, Vol. 1 *Immobilization of Enzymes and Cells*; Gordon F. Bickerstaff, Editor; Humana Press, Totowa, N.J., USA; 1997). The immobilization of the *A. facilis* 72W nitrilase catalyst has previously been reported (U.S. Pat. No. 6,870, 038).

The concentration of enzyme catalyst in the aqueous reaction mixture depends on the specific activity of the enzyme catalyst and is chosen to obtain the desired rate of reaction. The wet cell weight of the microbial cells used as catalyst in hydrolysis reactions typically ranges from 0.001 grams to 0.250 grams of wet cells per mL of total reaction volume, preferably from 0.002 grams to 0.050 grams of wet cells per mL.

The temperature of the glycolonitrile hydrolysis reaction is chosen to control both the reaction rate and the stability of the enzyme catalyst activity. The temperature of the reaction may range from just above the freezing point of the reaction mixture (approximately 0° C.) to about 65° C., with a preferred range of reaction temperature of from about 5° C. to about 35° C. The microbial cell catalyst suspension may be prepared by suspending the cells in distilled water, or in a aqueous solution of a buffer which will maintain the initial pH of the reaction between about 5.0 and about 10.0, preferably between about 5.5 and about 8.0, more preferably between about 5.5 and about 7.7, and most preferably about 6.0 to about 7.7. As the reaction proceeds, the pH of the reaction mixture may change due to the formation of an ammonium salt of the carboxylic acid from the corresponding nitrile functionality. The reaction can be run to complete conversion of glycolonitrile with no pH control, or a suitable acid or base can be added over the course of the reaction to maintain the desired pH.

Glycolonitrile was found to be completely miscible with water in all proportions at 25° C. In cases where reaction conditions are chosen such that the solubility of the substrate (i.e., an α-hydroxynitrile) is also dependent on the temperature of the solution and/or the salt concentration (buffer or product glycolic acid ammonium salt, also known as ammonium glycolate) in the aqueous phase, the reaction mixture may initially be composed of two phases: an aqueous phase containing the enzyme catalyst and dissolved α-hydroxynitrile, and an organic phase (the undissolved α-hydroxynitrile). As the reaction progresses, the α-hydroxynitrile dissolves into the aqueous phase, and eventually a single phase product mixture is obtained. The reaction may also be run by adding the α-hydroxynitrile to the reaction mixture at a rate approximately equal to the enzymatic hydrolysis reaction rate, thereby maintaining a single-phase aqueous reaction mixture, and avoiding the potential problem of substrate inhibition of the enzyme at high starting material concentrations.

Glycolic acid may exist in the product mixture as a mixture of the protonated carboxylic acid and/or its corresponding ammonium salt (dependent on the pH of the product mixture; pKa of glycolic acid is about 3.83), and may additionally be present as a salt of the carboxylic acid with any buffer that may additionally be present in the product mixture. Typically, the glycolic acid produced is primarily in the form of the ammonium salt (pH of the glycolonitrile hydrolysis reaction is typically between about 5.5 and about 7.7). The glycolic acid product may be isolated from the reaction mixture as the protonated carboxylic acid, or as a salt of the carboxylic acid, as desired.

The final concentration of glycolic acid in the product mixture at complete conversion of glycolonitrile may range from 0.001 M to the solubility limit of the glycolic acid product. In one embodiment, the concentration of glycolic acid will range from about 0.10 M to about 5.0 M. In another embodiment, the concentration of glycolic acid will range from about 0.2 M to about 3.0 M.

Glycolic acid may be recovered in the form of the acid or corresponding salt using a variety of techniques including, but not limited to ion exchange, electrodialysis, reactive solvent extraction, polymerization, thermal decomposition, alcoholysis, and combinations thereof (see co-pending U.S. Patent Application Publication No. 2006-0247467).

Microbial Expression

The nitrilase catalyst may be produced in heterologous host cells, preferably in microbial hosts. Particularly useful in the present invention will be cells that are readily adaptable to large-scale fermentation methods. Such organisms are well known in the art of industrial bioprocessing, examples of which may be found in *Recombinant Microbes for Industrial and Agricultural Applications*, Murooka et al., eds., Marcel Dekker, Inc., New York, N.Y. (1994), and include fermentative bacteria as well as yeast and filamentous fungi. Host cells may include, but are not limited to *Comamonas* sp., *Corynebacterium* sp., *Brevibacterium* sp., *Rhodococcus* sp., *Azotobacter* sp., *Citrobacter* sp., *Enterobacter* sp., *Clostridium* sp., *Klebsiella* sp., *Salmonella* sp., *Lactobacillus* sp., *Aspergillus* sp., *Saccharomyces* sp., *Yarrowia* sp., *Zygosaccharomyces* sp., *Pichia* sp., *Kluyveromyces* sp., *Candida* sp., *Hansenula* sp., *Dunaliella* sp., *Debaryomyces* sp., *Mucor* sp., *Torulopsis* sp., *Methylobacteria* sp., *Bacillus* sp., *Escherichia* sp., *Pseudomonas* sp., *Rhizobium* sp., and *Streptomyces* sp. Particularly preferred is *E. coli*. Examples of suitable *E. coli* host cells in which a mutant nitrilase gene can be expressed include, but are not limited to, host cells specified herein as MG1655 (ATCC 47076), FM5 (ATCC 53911), W3110 (ATCC 27325), MC4100 (ATCC 35695), W1485 (ATCC 12435), and their derivatives. In another aspect the preferred *E. coli* host strains are MG1655 (ATCC 47076) or FM5 (ATCC 53911), Heterologous expression of the *A. facilis* 72W nitrilase has previously been reported (Chauhan et al., supra; U.S. Pat. No. 6,870,038; U.S. Pat. No. 7,148,051; and U.S. Pat. No. 7,198, 927). Chauhan et al. report an *E. coli* strain (*E. coli* SS1001 (ATCC PTA-1177)) that expressed active *A. facilis* 72W nitrilase (SEQ ID NO: 57). The coding sequence of the recombinantly expressed (*E. coli* SS1001) nitrilase contained two minor sequence changes in comparison to the wild-type 72W nitrilase sequence (SEQ ID NOs: 3 and 4). The start codon was changed from GTG to ATG to facilitate recombinant expression and an artifact was introduced during cloning that resulted in a single amino acid change near the C-terminal (Pro367 [CCA]➔Ser [TCA]).

Recombinant expression in an industrially-suitable host has several advantages. First, the genetic toolbox for many of the commonly used production hosts is usually well developed in comparison to the genetic tools available for many of the microorganisms from which the gene of interest was obtained. Recombinant expression in these hosts is normally more cost effective than expression in the native host. For example, it has been shown that *A. facilis* 72W cells grow on glycerol, a relatively expensive carbon substrate, when grown by fermentation, and have not been successfully grown using inexpensive glucose. In contrast, *E. coli* transformants can be grown on glucose to the same cell density as *A. facilis* 72W cells in about half the time, significantly reducing biocatalyst production costs (U.S. Pat. No. 6,870,038).

Microbial expression systems and expression vectors containing regulatory sequences that direct high level expression of foreign proteins are well-known to those skilled in the art. These could be used to construct chimeric genes for production of the gene products. These chimeric genes could then be introduced into appropriate microorganisms via transformation to provide high level expression of the desired nitrilase.

Chimeric genes will be effective in altering the properties of a host cell. For example, introducing at least one copy of chimeric genes encoding the present nitrilases under the control of the appropriate promoters into a host cell gives the host cell an improved ability to convert glycolonitrile to glycolic acid. The chimeric genes will comprise suitable regulatory sequences useful for driving gene expression of the present mutant nitrilase sequences. Suitable regulatory sequences may include, but are not limited to promoters, translation leader sequences, and ribosomal binding sites. It is preferred if these sequences are derived from the host organism; however, the skilled person will recognize that heterologous regulatory sequences may also be used.

Chimeric genes can be introduced into an appropriate host by cloning it into a suitable expression vector. Vectors or cassettes useful for the transformation of suitable host cells are well known in the art. Typically, the vector or cassette contains sequences directing transcription and translation of the relevant gene, a selectable marker, and sequences allowing autonomous replication or chromosomal integration. Suitable vectors comprise a region 5' of the coding sequence that harbors transcriptional initiation controls and a region 3' of the DNA fragment which controls transcriptional termination. It is most preferred when both control regions are derived from genes homologous to the host cell, although such control regions need not be derived from the genes native to the specific species chosen as a production host.

In one embodiment, the regulatory sequences will include a promoter. Promoters may be constitutive or inducible. Inducible promoters are generally responsive to a specific stimulus (e.g., IPTG or lactose inducing the lac promoter). Inducible promoters may be responsive to a variety of stimuli, including, chemicals, growth cycle, changes in temperature, changes in pH and changes in osmolarity, to name only a few.

Initiation control regions or promoters that are useful to drive expression of the nitrilase in the desired host cell are numerous and familiar to those skilled in the art, including but not limited to CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, trp, $IP_L$, $IP_R$, T7, tac, $P_{BAD}$, npr, and trc (particularly useful for expression in *Escherichia coli*). Additional examples of promoters particularly suitable for driving expression in *E. coli* include, but are not limited to the tryptophan operon promoter Ptrp of *E. coli*, a lactose operon promoter Plac of *E. coli*, a Ptac promoter of *E. coli*, a phage lambda right promoter $P_R$, a phage lambda left promoter $P_L$, a T7 promoter, and a promoter of the GAP gene from *Pichia pastors*, or is at least one promoter isolated from the group of microorganisms selected from the group consisting of *Comamonas, Corynebacterium, Brevibacterium, Rhodococcus, Azotobacter, Citrobacter, Enterobacter, Clostridium, Klebsiella, Salmonella, Lactobacillus, Aspergillus, Saccharomyces, Pichia, Zygosaccharomyces, Kluyveromyces, Candida, Hansenula, Dunaliella, Debaryomyces, Mucor, Torulopsis, Methylobacteria, Bacillus, Escherichia, Pseudomonas, Rhizobium*, and *Streptomyces*.

Termination control regions may also be derived from various genes native to the preferred hosts. Optionally, a termination site may be unnecessary; however, it is most preferred if included.

Additionally, the inserted genetic material may include a ribosome binding site (RBS). The ribosome binding site may be from a phage lambda CII gene or is selected from the group consisting of ribosome binding sites from a gene of *Comamonas, Corynebacterium, Brevibacterium, Rhodococcus, Azotobacter, Citrobacter, Enterobacter, Clostridium, Klebsiella, Salmonella, Lactobacillus, Aspergillus, Saccharomyces, Zygosaccharomyces, Pichia, Kluyveromyces, Candida, Hansenula, Dunaliella, Debaryomyces, Mucor, Torulopsis, Methylobacteria, Bacillus, Escherichia, Pseudomonas, Rhizobium*, and *Streptomyces*.

Optionally, the gene products may preferably be a secreted product of the transformed host. Secretion of desired proteins into the growth media simplifies purification procedures and reduces costs. Secretion signal sequences are often useful in facilitating the active transport of expressible proteins across cell membranes. A transformed host capable of secretion may be created by incorporating in the host a DNA sequence that codes for a secretion signal. Methods for choosing appropriate signal sequences are well known in the art (see for example EP 546049; WO 93/24631). The secretion signal DNA may be located between the expression-controlling DNA and the instant coding sequence or coding sequence fragment, and in reading frame with the latter.

Industrial Production of the Microbial Catalyst

Where commercial production of the nitrilase catalyst is desired, a variety of culture methodologies may be used. Fermentation runs may be conducted in batch, fed-batch, or continuous mode, methods well-known in the art (Thomas D. Brock in *Biotechnology: A Textbook of Industrial Microbiology*, Second Edition (1989) Sinauer Associates, Inc., Sunderland, Mass., (1989); Deshpande, Mukund V., *Appl. Biochem. Biotechnol.* 36(3): 227-234 (1992)).

A classical batch culturing method is a closed system where the composition of the media is set at the beginning of the culture and not subject to artificial alterations during the culturing process. Thus, at the beginning of the culturing process the media is inoculated with the desired organism or organisms and growth or metabolic activity is permitted to occur adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of end product or intermediate in some systems. Stationary or post-exponential phase production can be obtained in other systems.

A variation on the standard batch system is the Fed-Batch system. Fed-Batch culture processes are also suitable in the present invention and comprise a typical batch system with the exception that the substrate is added in increments as the culture progresses. Fed-Batch systems are useful when catabolite repression is apt to inhibit the metabolism of the cells and where it is desirable to have limited amounts of substrate in the media, Measurement of the actual substrate concentration in Fed-Batch systems is difficult and is therefore estimated on the basis of the changes of measurable factors such as pH, dissolved oxygen, and the partial pressure of waste gases such as $CO_2$. Batch and Fed-Batch culturing methods are common and well known in the art and examples may be found in Brock (supra) and Deshpande (supra).

Commercial production of the nitrilase catalysts may also be accomplished with a continuous culture. Continuous cultures are an open system where a defined culture media is added continuously to a bioreactor and an equal amount of conditioned media is removed simultaneously for processing. Continuous cultures generally maintain the cells at a constant high-liquid-phase density where cells are primarily in log phase growth. Alternatively, continuous culture may be practiced with immobilized cells where carbon and nutrients are continuously added and valuable products, by-products or waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end cell concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady-state growth conditions and thus the cell loss due to media being drawn off must be balanced against the cell growth rate in the culture. Methods of modulating nutrients and growth factors for continuous culture processes, as well as techniques for maximizing the rate of cell formation, are well known in the art of industrial microbiology and a variety of methods are detailed by Brock (supra).

Fermentation media in the present invention must contain suitable carbon substrates. Suitable substrates may include, but are not limited to monosaccharides such as glucose and fructose, disaccharides such as lactose or sucrose, polysaccharides such as starch or cellulose or mixtures thereof, and unpurified mixtures from renewable feedstocks such as cheese whey permeate, cornsteep liquor, sugar beet molasses, and barley malt. Hence, it is contemplated that the source of carbon utilized in the present invention may encompass a wide variety of carbon-containing substrates and will only be limited by the choice of organism.

Applicants specifically incorporate the entire contents of all cited references in this disclosure. Further, when an amount, concentration, or other value or parameter is given either as a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

General Methods

The following examples are provided to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Materials and methods suitable for the maintenance and growth of bacterial cultures are well known in the art. Techniques suitable for use in the following examples may be found as set out in *Manual of Methods for General Bacteriology* (1994) (Phillipp Gerhardt, R. G. E. Murray, Ralph N. Costilow, Eugene W. Nester, Willis A. Wood, Noel R. Krieg and G. Briggs Phillips, eds.), American Society for Microbiology, Washington, D.C.) or by Thomas D. Brock, in *Biotechnology: A Textbook of Industrial Microbiology*, (1989) Second Edition, (Sinauer Associates, Inc., Sunderland, Mass.). Methods to immobilize enzymatic catalysts can be found in Bickerstaff, G. F., supra).

Procedures required for genomic DNA preparation, PCR amplification, DNA modifications by endo- and exo-nucleases for generating desired ends for cloning of DNA, ligations, and bacterial transformation are well known in the art. Standard recombinant DNA and molecular cloning techniques used here are well known in the art and are described by Maniatis, supra; and by T. J. Silhavy, M. L. Bennan, and L. W, Enquist, *Experiments with Gene Fusions*, (1984) Cold Spring Harbor Laboratory Press, Cold Spring, N.Y.; and by Ausubel, F. M. et al., *Current Protocols in Molecular Biology*, (1994-1998) John Wiley & Sons, Inc., New York.

All reagents and materials were obtained from Aldrich Chemicals (Milwaukee, Wis.), DIFCO Laboratories (Detroit, Mich.), GIBCO/BRL (Gaithersburg, Md.), or Sigma/Aldrich Chemical Company (St. Louis, Mo.) unless otherwise specified.

The abbreviations in the specification correspond to units of measure, techniques, properties, or compounds as follows: "sec" means second(s), "min" means minute(s), "h" or "hr" means hour(s), "d" means density in g/mL, "µL" means microliters, "mL" means milliliters, "L" means liters, "mM" means millimolar, "M" means molar, "mw" means average molecule weight, "mmol" means millimole(s), "wt" means weight, "wt %" means weight percent, "g" means grams, "µg" means micrograms, HPLC" means high performance liquid chromatography, "O.D." means optical density at the designated wavelength, "ddw" means dry cell weight, 'U' means units of nitrilase activity, "EDTA" means ethylenediaminetetraacetic acid, "DTT" means dithiothreitol, "DI" means distilled and deionized", and "NCIMB" means National Collections of Industrial Food and Marine Bacteria, Bucksburn, Aberdeen, Scotland, UK. One U of nitrilase activity corresponds to the hydrolysis of 1 µmol glycolonitrile/min.

Analytical Methodology

HPLC Analysis

Unless otherwise noted, the following HPLC method was used. The reaction product mixtures were analyzed by the following HPLC method. Aliquots (0.01 mL) of the reaction mixture were added to 1.50 mL of water, and analyzed by HPLC (HPX 87H column, 30 cm×7.8 mm; 0.01 $NH_2SO_4$ mobile phase; 1.0 mL/min flow at 50 (C; 10 µL injection volume; RI detector, 20 min analysis time). The method was calibrated for glycolonitrile at a series of concentrations using commercially available glycolonitrile purchased from Aldrich.

Example 1

Dependence of Nitrilase Specific Activity of Unimmobilized *E. coli* MG1655/pSW138-168V on Added Polyethylenimine To a 20-mL glass vial with magnetic stir bar was added 1.0 mL of a 25.0 mg (dry cell wt.)/mL suspension of *E. coli* MG1655/pSW138-168V (SEQ ID NO: 51) in 0.1 M $KH_2PO_4$ buffer (pH 7.5), and either 1.0 ml of 0.3 M $KH_2PO_4$ buffer (pH 7.5) or 1.0 mL of a 10.2 mg/mL solution of polyethylenimine (BASF LUPASOL® PS, 750,000 mw; BASF Aktiengesellschaft, Ludwigshafen, Germany) in 0.3 M $KH_2PO_4$ buffer (pH 7.5) at 25° C. With stirring, 2.0 mL of an aqueous solution containing glycolonitrile (1.0 M) and formaldehyde (8 mM, 1 mM, or 0.04 mM) in distilled, deionized water at 25° C. was added, and the reaction mixture maintained at 25° C. with a temperature bath. At 5, 10, 15, and 30 minutes, a 100 µl aliquot of the reaction mixture was removed and mixed with 100 µl of water, 10 µl of 6.0 N HCl and 200 µl of 0.25 M n-propanol in water (HPLC external standard), the mixture centrifuged, and the resulting supernatant analyzed by HPLC to determine the initial reaction rate and catalyst specific activity (U/g dcw) (Table 2).

TABLE 2

Dependence of biocatalyst specific activity on concentration of formaldehyde with and without added polyethylenimine (PEI).

| glycolonitrile (mM) | formaldehyde (mM) | PEI (mg/mL) | specific activity (U/g dcw) |
|---|---|---|---|
| 500 | 4.0 | 0 | 471 |
| 500 | 4.0 | 5.1 | 1484 |
| 500 | 0.50 | 0 | 1344 |
| 500 | 0.50 | 5.1 | 1726 |
| 500 | 0.02 | 0 | 1742 |
| 500 | 0.02 | 5.1 | 1629 |

Example 2

Preparation of Copoly(Vinylalcohol/Vinylamine)

A solution of 0.2 g sodium dodecylbenzenesulfonate (Sigma-Aldrich Catalog #289957) and 0.2 g sodium dihydrogen phosphate in 80 mL deionized water was placed in a 250-mL, 4-neck RB flask with condenser and nitrogen inlet, thermometer, dropping funnel and magnetic stirrer. The flask was swept with nitrogen and was stirred in a 72° C. water bath until the solution temperature was 65° C.; then 0.1 g VAZO®-64 (2,2'-azobisisobutyronitrile; mw: 164.2; Sigma-Aldrich catalog #441090) initiator was added.

A solution of 40 g vinyl acetate (Sigma-Aldrich catalog #V1503, filtered through basic alumina to remove inhibitor), 4 g N-vinylformamide (Sigman-Aldrich catalog #447331, used without further purification) and 0.3 g VAZO® 64 was placed in the dropping funnel and 5 mL of this monomer solution was added to the flask. The mixture was stirred 20 min and another 5 mL of monomer was added. Five-mL aliquots of monomer were added every 20 min until 20 mL had been added (at 1 hr); then the mixture was stirred at 70° C. for 1 hr. After this the remainder of the monomer was added at a rate of 5 mL every 20 min. Monomer addition was complete at 4 h, and then the mixture was stirred at 70° C. for 3 h and allowed to cool to room temperature (approximately 22° C.). The resulting polymer beads were washed several times with hot water and then allowed to stand in water for 72 hr. The beads were then washed with diethyl ether and allowed to stand in ether for 15 min to extract vinyl monomers, followed by filtration and drying under vacuum with a nitrogen blanket, then dried overnight at 70° C. in a vacuum oven at 350 mm Hg with a nitrogen sweep to yield 39.0 g of poly(vinylacetate-vinylformamide)copolymer.

Poly(vinylacetate-vinylformamide)copolymer (25.1 g) was stirred at reflux with 200 mL methanol containing 6 mL concentrated HCl and 5 mL water for 5 h, yielding a clear solution which was allowed to stand at RT overnight. The solution became a rubbery gel; this was blended with several changes of acetone to precipitate the hydrolyzed polymer HCl salt, which was dried under nitrogen in the vacuum oven at 75° C. (yield: 15 g). Analysis by $^1$H NMR (DMSO-d6) indicated about 20% of the acetates remained unhydrolyzed, so the product was stirred at reflux with a mixture of 150 mL methanol and 5 mL conc. HCl overnight to complete hydrolysis. The methanol was filtered off, and the rubbery, methanol-insoluble product was stirred with 100 mL DI water at 90° C.; this solution was filtered first through a screen to remove a small amount of gel and then through a Millipore cellulose prefilter (Millipore Corp., Bedford, Mass.) under pressure. The filtered solution was basified to pH 9.0 with 10% NaOH and then dialyzed overnight against DI water in a MEMBRA-CEL® 3.5K molecular weight cut-off dialysis membrane tube (Viskase Co., Willowbrooke, Ill.). Lyophilization yielded 8.7 g of copoly(vinylalcohol/vinylamine).

Example 3

Dependence of Nitrilase Specific Activity of Unimmobilized *E. coli* MG1655/pSW138-168V on Added Amine Protectants To a 20-mL glass vial with magnetic stir bar was added 20 mg to 400 mg of amine protectant (see Table 2), followed by 1.825 mL of deionized water and 1.0 mL of 0.3 M $KH_2PO_4$ buffer (pH 7.5). The pH of the resulting mixture was checked and re-adjusted to pH 7.5 with 6 N HCl. When the pH of the resulting mixture was stable at pH 7.5, 10 mL of a ca. 25.0 mg (dry cell wt.)/mL suspension of *E. coli* MG 1655/pSW138-168V (SEQ ID NO: 51) in 0.1 M $KH_2PO_4$ buffer (pH 7.5) was added, then the reaction was initiated by the addition of 0.175 mL (0.187 g) of aqueous glycolonitrile (61 wt % GLN in water, 2.00 mmol of glycolonitrile in solution also containing either 0.80 mol % or 0.10 mol % formaldehyde relative to glycolonitrile), and the reaction mixture maintained at 25° C. with a temperature bath. At 5, 10, 15, and 30 minutes, a 100 Ml aliquot of the reaction mixture was removed and mixed with 100 µl of water, 10 Fl of 6.0 N HCl and 200 µl of 0.25 M n-propanol in water (HPLC external standard), the mixture centrifuged, and the resulting supernatant analyzed by HPLC to determine the initial reaction rate and catalyst specific activity (U/g dcw) (Table 3). Each set of experiments listed in Table 3 were performed with a freshly-prepared cell suspension (cell suspensions A-G), where the differences in the specific activity of the cells in the control reaction for each cell suspension were due to differences in the dry cell weight concentrations of the individual cell suspensions.

TABLE 3

Dependence of biocatalyst specific activity on concentration of formaldehyde with and without added amine protectant.

| cell suspension | glycolonitrile (mM) | formaldehyde (mM) | amine protectant | amine protectant (mg/mL) | specific activity (U/g dcw) |
|---|---|---|---|---|---|
| A | 500 | 4.0 | PEI/silica (Aldrich 24675-1) | 100 | 491 |
| A | 500 | 4.0 | PEI/cellulose (Sigma P6883) | 100 | 1212 |
| A | 500 | 4.0 | none (control) | 0 | 385 |
| B | 500 | 4.0 | 3-aminopropyl silica gel (Sigma A1409) | 100 | 799 |
| B | 500 | 4.0 | none (control) | 0 | 481 |
| C | 500 | 4.0 | Long-chain alkyl amine controlled pore glass (Sigma L8638) | 100 | 1136 |
| C | 500 | 4.0 | none (control) | 0 | 527 |
| D | 500 | 0.5 | Long-chain alkyl amine controlled pore glass (Sigma L8638) | 100 | 1891 |
| D | 500 | 0.5 | none (control) | 0 | 1325 |
| E | 500 | 4.0 | polyallylamine (Aldrich 47914-4) | 5 | 598 |
| E | 500 | 4.0 | polyallylamine (Aldrich 47914-4) | 10 | 648 |
| E | 500 | 4.0 | PVOH/poly-vinylamine (Example 2) | 70 | 1541 |
| E | 500 | 4.0 | Poly-D-lysine (Sigma P0296) | 11 | 502 |
| E | 500 | 4.0 | none (control) | 0 | 464 |
| F | 500 | 0.5 | PVOH/poly-vinylamine (Example 2) | 70 | 1786 |
| F | 500 | 0.5 | Poly-D-lysine (Sigma P0296) | 11 | 1388 |
| F | 500 | 0.5 | none (control) | 0 | 1220 |
| G | 500 | 4.0 | DIAION ® WA20 (Mitsubishi Chemical) | 100 | 1128 |
| G | 500 | 4.0 | DIAION ® WA21J (Mitsubishi Chemical) | 100 | 1073 |
| G | 500 | 4.0 | none (control) | 0 | 508 |
| G | 500 | 0.5 | DIAION ® WA20 (Mitsubishi Chemical) | 100 | 1335 |
| G | 500 | 0.5 | DIAION ® WA21J (Mitsubishi Chemical) | 100 | 1339 |
| G | 500 | 0.5 | none (control) | 0 | 1182 |

Example 4

Preparation of GA/PEI-Crosslinked Carrageenan/*E. coli* MG1655/pNM18-168V Beads

With rapid stirring, 12 g of carrageenan (FMC GP911; FMC Corp., Philadelphia, Pa.) was slowly added to 228 g deionized distilled water at 50° C., the resulting mixture heated to 80° C. until the carrageenan was completely dissolved, and the resulting solution cooled with stirring to 52° C. In a separate beaker equipped with stir bar, 83.2 g of frozen *E. coli* MG1655/pNM18-168V (SEQ ID NO: 51) cells (25.2% dcw) was added to 84.8 g of 0.35 M $Na_2HPO_4$ (pH 7.3) at ca. 25° C. and mixed until the cells were suspended, then a deoxyribonuclease I solution (10 μL of 12,500 U/mL DNase (Sigma-Aldrich)/100 mL of cell suspension) was added. The cell suspension was filtered consecutively through a 230 micron and 140 micron NUPRO® TF strainer (Swagelok Company, Solon, Ohio) element filter, and heated with stirring to 50° C. With stirring, 160.0 g of *E. coli E. coli* MG1655/pNM18-168V cell suspension at 50° C. was added to the carrageenan solution at 52° C., and the resulting cell/carrageenan suspension was pumped through an electrically-heated 20 gauge needle at 47° C. and dripped into 0.25 M $KHCO_3$ (pH=7.3) with stirring at ca. 37-38° C.); the flow rate through the needle was set at 5-8 mL/min. The resulting beads were allowed to harden in this same buffer for 1 h at room temperature with stirring, and were stored in 0.25 M potassium bicarbonate (pH 7.3).

Chemical cross-linking of a portion of the immobilized cell/carrageenan beads was performed by addition of 1.0 g of 25% glutaraldehyde (GA) in water (Sigma M 752-07) to 20 g beads suspended in 48 mL of 0.25 M potassium bicarbonate (pH 7.3), and stirring for 1 h at room temperature. To the suspension of beads was then added 4.0 g of 12.5 wt % polyethylenimine (PEI, BASF LUPASOL® PS) in water, and the bead suspension stirred for an additional 18 h at room temperature. The GA/PEI-crosslinked beads were recovered from the suspension, stirred twice for 15 min in 48 mL of 0.25 M potassium bicarbonate (pH 7.3), then stored in 1.0 M ammonium bicarbonate (pH 7.3) at 5° C. Prior to use, the beads were washed twice for 15 min with 180 mL of 0.1 M ammonium glycolate (pH 7.0) at room temperature.

Example 5

Dependence of Biocatalyst Specific Activity on Glutaraldehyde/Polyethylenimine Cross-Linking of Carrageenan-Immobilized *E. coli* MG1655/pSW138-168V Transformants Expressing *A. facilis* 72W Nitrilase In a typical procedure, a 50-mL jacketed reaction vessel equipped with overhead stirring and temperature control was charged with 4.0 g of GA/PEI cross-linked *E. coli* MG1655/pSW138-168V/carrageenan beads (prepared using the process as described in Example 4) containing 5% (dcw) transformant expressing the *A. facilis* 72W nitrilase mutant F168V (SEQ ID NO: 51). To the vessel was then added 10.85 mL of distilled water and 3.0 mL of aqueous ammonium glycolate (4.0 M, pH 7.0). The mixture was stirred at 25° C. while 1.75 mL of 60.8 wt % glycolonitrile (GLN) in water (1.876 g, 20.0 mmol GLN, 0.160 mmol formaldehyde; stabilized with 0.7 wt % glycolic acid)) and 0.40 mL of aqueous ammonium hydroxide (1.875 wt % $NH_3$) was added simultaneously (final pH 7.5). Four 0.050-mL reaction samples were removed at pre-determined times after the GLN addition and analyzed by HPLC to determine the initial reaction rate and the catalyst specific activity (μmol glycolic acid/min/g dcw biocatalyst).

TABLE 4

Dependence of immobilized biocatalyst specific activity on glutaraldehyde/polyethylenimine cross-linking.

| glycolonitrile (mM) | formaldehyde (mM) | GA/PEI cross-linked | specific activity (U/g beads) | specific activity (U/g dcw) |
|---|---|---|---|---|
| 1000 | 8.0 | no | 36.2 | 723 |
| 1000 | 8.0 | yes | 68.2 | 1364 |
| 1000 | 1.0 | no | 58.4 | 1169 |
| 1000 | 1.0 | yes | 99.7 | 1994 |
| 1000 | 0.04 | no | 68.8 | 1375 |
| 1000 | 0.04 | yes | 90.1 | 1801 |

Example 6

Comparison of Biocatalyst Specific Activity for Uncross-Linked and Glutaraldehyde/Polyethylenimine Cross-Linked Carrageenan-Immobilized *E. coli* MG1655/pSW138-168V Transformants Expressing *A. facilis* 72W Nitrilase in Consecutive Batch Reactions with Catalyst Recycle A 50-mL jacketed reaction vessel equipped with overhead stirring and temperature control was charged with 8 g of GA/PEI-crosslinked *E. coli* MG1655/pSW138-168V/carrageenan beads (prepared using the process as described in Example 4) containing 5% (dcw) transformant expressing the *A. facilis* 72W nitrilase mutant F168V (SEQ ID NO: 51). To the vessel was then added 14.78 mL of distilled water and 6.0 mL of aqueous ammonium glycolate (4.0 M, pH 7.0), and the reaction vessel flushed with nitrogen. The mixture was stirred at 25° C. while programmable syringe pumps were used to simultaneously add 1.07 mL of 60 wt % glycolonitrile (GLN) in water (12.0 mmol GLN, 0.084 mmol formaldehyde; Fluka (redistilled, stabilized with 0.5 wt % glycolic acid, available from Sigma-Aldrich) and 0.150 mL of aqueous ammonium hydroxide (1.875 wt %); one equivalent volume of GLN and ammonium hydroxide solutions was added simultaneously every 2 h to maintain the concentration of GLN at ≦400 mM and the pH within a range of 6.5-7.5. Four 0.050-mL reaction samples were removed at pre-determined times after the first GLN addition and analyzed by HPLC to determine the initial reaction rate and the catalyst specific activity (μmol glycolic acid/min/g dcw biocatalyst). At completion of the reaction, there was 100% conversion of GLN to produce glycolic acid (as the ammonium salt) in >99% yield, and the concentration of ammonium glycolate produced from added GLN was approximately 2.5 M (3.1 M total ammonium glycolate when including initial ammonium glycolate buffer in a final reaction volume of ca. 38.0 mL).

At the end of the first reaction, the aqueous product mixture was decanted from the catalyst (under nitrogen), leaving ca. 10.3 g of a mixture of immobilized cell catalyst (8.0 g) and remaining product mixture (ca. 2.3 g). To the reaction vessel then added 20.78 mL of distilled, deionized water, and a second reaction was performed at 25° C. by the addition of aliquots of aqueous GLN and ammonium hydroxide as described immediately above. The specific activity of recovered biocatalyst in consecutive batch reactions with catalyst recycle are listed in Table 5. To compare the effect of glutaraldehyde/polyethylenimine cross-linking of carrageenan-immobilized cells on specific activity, a second series of recycle reactions was performed as described above, except that the *E. coli* MG1655/pSW138-168V/carrageenan beads were not chemically-crosslinked with glutaraldehyde and polyethylenimine (Table 5).

TABLE 5

Dependence of biocatalyst specific activity on glutaraldehyde/PEI cross-linking of carrageenan-immobilized microbial catalyst in consecutive batch reactions with catalyst recycle

| | biocatalyst specific activity (U/g dcw) | |
|---|---|---|
| Reaction Number | with GA/PEI cross-linking | without GA/PEI cross-linking |
| 1 | 1312 | 215 |
| 2 | 871 | 385 |
| 3 | 897 | 270 |
| 4 | 816 | |
| 5 | 898 | 296 |
| 6 | 697 | |
| 7 | 663 | |
| 8 | 792 | |
| 9 | 732 | |
| 10 | 760 | 393 |
| 11 | 539 | |
| 12 | 495 | 373 |
| 13 | 396 | |
| 14 | 560 | |
| 15 | 324 | 443 |
| 16 | 426 | |
| 17 | 500 | 366 |
| 18 | 722 | 394 |
| 19 | 489 | |
| 20 | | |
| 21 | | 283 |
| 22 | 444 | |
| 23 | | 325 |
| 24 | | |
| 25 | 501 | |
| 26 | 508 | 285 |

TABLE 5-continued

Dependence of biocatalyst specific activity on glutaraldehyde/PEI
cross-linking of carrageenan-immobilized microbial catalyst
in consecutive batch reactions with catalyst recycle

| Reaction Number | biocatalyst specific activity (U/g dcw) | |
|---|---|---|
| | with GA/PEI cross-linking | without GA/PEI cross-linking |
| 27 | 487 | 224 |
| 28 | 349 | |
| 29 | 371 | |
| 30 | 345 | 224 |

Example 7

Dependence of Nitrilase Specific Activity of Unimmobilized *Rhodococcus* sp. (ATCC 39484™) on Added Polyethylenimine A lyophilized culture of *Rhodococcus* sp. ATCC 39484 (SEQ ID NO: 25) was suspended in 5 ml of nutrient broth (Difco; catalog #0003-01-6) in a 50-mL conical test tube and revived following incubation at 30° C. for 3 days at 60 rpm, followed by storage at −80° C. after addition of glycerol (10% v/v). The revived culture (1 mL) was inoculated into a 125-mL unbaffled shake flask containing 50 mL of Miller's Luria-Bertani broth (Mediatech, Inc.; 46-050-CM; Manassas, Va.) and grown for 16 h at 30° C. and 200 rpm to an OD of 9.0 at 600 nm, then glycerol (10% v/v) was added and the inoculum stored at −80° C. The inoculum (2 mL) was transferred to a 1-L unbaffled shake flask containing 200 mL of a medium consisting of 1 g polypeptone (Becton-Dickinson; catalog #11910; Franklin Lakes, N.J.), 0.6 g malt extract (Difco; 0186-02-4), 0.6 g yeast extract (Difco; 0127-17), 2 g glycerol, and 0.2 mL of isovaleronitrile (T. Nagasawa, M. Kobayashi, H. Yamada, *Archives of Microbiology*, (1988) 150:89-94) at pH 7.0, followed by growth at 30° C. with 200 rpm agitation. At 50 hr and 70 hr the culture was fed with 0.1% (v/v) and 0.2% (v/v) of isovaleronitrile, respectively. The cell paste was harvested at 96 h by centrifugation at 13,000×g (5° C.) and stored at −80° C.

To a 20-mL glass vial with magnetic stir bar was added 1.0 mL of a 73.0 mg (dry cell wt.)/mL suspension of *Rhodococcus* sp. (ATCC 39484™) in 0.1 M $KH_2PO_4$ buffer (pH 7.5), and either 1.0 ml of 0.3 M $KH_2PO_4$ buffer (pH 7.5) or 1.0 mL of a 10.2 mg/mL solution of polyethylenimine (BASF LUPASOL® PS, 750,000 mw) in 0.3 M $KH_2PO_4$ buffer (pH 7.5) at 25° C. With stirring, 2.0 mL of an aqueous solution containing glycolonitrile (1.0 M) and formaldehyde (8 mM or 0.04 mM) in distilled, deionized water at 25° C. was added, and the reaction mixture maintained at 25° C. At 5, 10)$_{1-5}$, and 30 minutes, a 100 µl aliquot of the reaction mixture was removed and mixed with 100 µl of water, 10 µl of 6.0 N HCl and 200 µl of 0.25 M n-propanol in water (HPLC external standard), the mixture centrifuged, and the resulting supernatant analyzed by HPLC to determine the initial reaction rate and catalyst specific activity (U/g dcw) (Table 6).

TABLE 6

Dependence of *Rhodococcus* sp. (ATCC 39484 ™) nitrilase
specific activity on concentration of formaldehyde with
and without added polyethylenimine (PEI).

| glycolonitrile (mM) | formaldehyde (mM) | PEI (mg/mL) | specific activity (U/g dcw) |
|---|---|---|---|
| 500 | 4.0 | 0 | 598 |
| 500 | 4.0 | 5.0 | 780 |

Example 8 Dependence of Nitrilase Specific Activity of Unimmobilized *Rhodococcus rhodochrous* (NCIMB 11216) on Added Polyethylenimine

*Rhodococcus rhodochrous* (NCIMB 11216; SEQ ID NO: 24) was revived following suspension of the preserved culture in 100 µL of normal saline, followed by streaking of the normal saline cell suspension onto plates containing nutrient agar (Difco catalog #0001-01-8) supplemented with yeast extract (2 g/L; Difco catalog #0127-17) and sodium chloride (5 g/L). The sequence of the nitrilase from *R. rhodochrous* NCIMB 11216 has been reported (U.S. Patent Application Publication No. 2003/0157672 and GENBANK® Accession No. CAC88237; SEQ ID NO: 24) The plates were incubated at 30° C. for 48 h and colonies were inoculated into aqueous E2 basal medium supplemented with adipic acid (0.8 wt %; carbon source) and propionitrile (0.2 wt %; nitrogen source) and incubated for 48 h at 30° C. with 200 rpm agitation. The E2 basal medium consisted of: $KH_2PO_4$, 1.4 g/L; $NaH_2PO_4$, 0.69 g/L; Sodium citrate, 0.1 g/L; $CaCl_2.2H_2O$, 0.025 g/L; KCl, 0.5 g/L; NaCl, 1.0 g/L; $MgSO_4.7H_2O$, 0.5 g/L; $FeSO_4.7H_2O$, 0.05 g/L; $CoCl_2.6H_2O$, 0.01 g/L; $MnCl_2.4H_2O$, 0.001 g/L; $ZnCl_2$, 0.0005 g/L; $NaMoO_4.2H_2O$, 0.0025 g/L; $NiCl_2.6H_2O$, 0.01 g/L; $CuSO_4.2H_2O$, 0.005 g/L; Biotin, 0.0002 g/L; Folic Acid, 0.0002 g/L; Pyridoxine-HCl, 0.001 g/L; Riboflavine, 0.0005 g/L; Thiamine.HCl, 0.00005 g/L; Nicotinic Acid, 0.0005 g/L; Pantothenic Acid, 0.0005 g/L; Vitamin $B_{12}$, 0.00001 g/L, p-Aminobenzoic Acid, 0.0005 g/L. Following 48 h of growth, 1.59 g of wet cell paste was harvested by centrifugation at 13,000×g, and the resulting cell paste was stored at −80° C.

To a 20-mL glass vial with magnetic stir bar was added 1.0 mL of a 79.0 mg (dry cell wt.)/mL suspension of *Rhodococcus rhodochrous* (NCIMB 11216) in 0.1 M $KH_2PO_4$ buffer (pH 7.5), and either 1.0 ml of 0.3 M $KH_2PO_4$ buffer (pH 7.5) or 1.0 mL of a 10.2 mg/mL solution of polyethylenimine (BASF LUPASOL® PS, 750,000 mw) in 0.3 M $KH_2PO_4$ buffer (pH 7.5) at 25° C. With stirring, 2.0 mL of an aqueous solution containing glycolonitrile (1.0 M) and formaldehyde (8 mM or 0.04 mM) in distilled, deionized water at 25° C. was added, and the reaction mixture maintained at 25° C. At 5, 10, 15, and 30 minutes, a 100 µl aliquot of the reaction mixture was removed and mixed with 100 µl of water, 10 µl of 6.0 N HCl and 200 µl of 0.25 M n-propanol in water (HPLC external standard), the mixture centrifuged, and the resulting supernatant analyzed by HPLC to determine the initial reaction rate and catalyst specific activity (U/g dcw) (Table 7).

TABLE 7

Dependence of *Rhodococcus rhodochrous* (NCIMB 11216) nitrilase
specific activity on concentration of formaldehyde with
and without added polyethylenimine (PEI).

| glycolonitrile (mM) | formaldehyde (mM) | PEI (mg/mL) | specific activity (U/g dcw) |
|---|---|---|---|
| 500 | 4.0 | 0 | 37.9 |
| 500 | 4.0 | 5.0 | 45.4 |

What is claimed is:

1. A process for enzymatically converting glycolonitrile to glycolic acid, said process comprising:
   (a) providing a set of reaction components comprising:
      (i) an aqueous solution of glycolonitrile comprising at least 0.01 ppm formaldehyde;
      (ii) an enzyme catalyst comprising a polypeptide having nitrilase activity wherein said polypeptide has the amino acid sequence set forth in SEQ ID NO:4; wherein said enzyme catalyst comprises a specific activity for hydrolyzing glycolonitrile to glycolic acid; and
      (iii) an effective amount of at least one amine protectant selected from the group consisting of:
         a) a compound of the formula

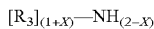

wherein X is 0 or 1 and $R_3$ is independently C1 to C20 hydrocarbyl group or substituted hydrocarbyl group, wherein $R_3$ optionally comprises one or more ether linkages; with the proviso that (i) the substituted group is not a cyano group capable of reacting with the enzyme catalyst and (ii) $R_3$ is not a carbonyl group,
         b) a polyamine polymer comprising an effective number of free amine groups; and
         c) an amine-functionalized material comprising an effective number of free amine groups; wherein the amine protectant is not naturally-produced by said enzyme catalyst;
   (b) combining the set of reaction components under suitable aqueous reaction conditions whereby glycolic acid is produced; wherein said specific activity is increased by the addition of said at least one amine protectant; and
   (c) recovering the glycolic acid or salt thereof produced in (b).

2. The process of claim 1 wherein the amine protectant is soluble under said suitable aqueous reaction conditions.

3. The process of claim 1 wherein the amine protectant is insoluble under said suitable aqueous reaction conditions.

4. The process of claim 3 wherein the enzyme catalyst is not immobilized in a matrix comprising said amine protectant.

5. The process of claim 3 wherein the enzyme catalyst is immobilized in an insoluble matrix comprising said amine protectant.

6. The process of claim 5 wherein the enzyme catalyst is immobilized in or on an insoluble matrix comprising polyethylenimine.

7. The process of claim 6 wherein the enzyme catalyst is immobilized in or on a glutaraldehyde-polyethyleneimine crosslinked carrageenan particle or bead.

8. The process of claim 1 wherein the polyamine polymer is selected from the group consisting of 2-amino-2-deoxy-(1→4)-β-D-glucopyranan, polyalkyleneamine polymers having alkylene moieties of 2 to 12 carbon atoms, polyethylenimine, polyallylamine, polyvinyl alcohol/polyvinylamine copolymers, D-polylysine, L-polylysine, mixtures of D/L polylysine, polyethylenimine cross-linked with glutaraldehyde, and mixtures thereof.

9. The process of claim 8 wherein the polyamine polymer has an average molecule weight ranging from 1,000 Daltons to 2,000,000 Daltons.

10. The process of claim 1 wherein the amine-functionalized material is selected from the group consisting of an amine-functionalized polymer and an amine-functionalized support material.

11. The process of claim 10 wherein the amine-functionalized polymer is selected from the group consisting of amine-functionalized polysaccharides, amine-functionalized glycans, amine-functionalized agarose, amine-functionalized carrageenan, amine-functionalized alginate, amine-functionalized dextran, amine-functionalized cellulose, amine-functionalized methacrylates, amine-functionalized polyurethanes, amine-functionalized polyesters, amine-functionalized nylons, amine-functionalized polystyrene, and amine-functionalized polyvinyl alcohols.

12. The process of claim 10 wherein the amine-functionalized support material is selected from the group consisting of amine-functionalized alumina, amine-functionalized silica, amine-functionalized magnetite, amine-functionalized controlled pore glass, weakly basic anion exchange resins comprising one or more primary or secondary amine groups, aminopropylsilated glass beads, ω-aminohexylagarose, ω-aminododecylagarose, and ω-aminoethylagarose.

13. The process of claim 12 wherein the amine-functionalized support material is functionalized with polyethylenimine.

14. The process of claim 13 wherein the amine-functionalized support material is selected from the group consisting of polyethyleneimine-functionalized silica and polyethyleneimine-functionalized polystyrene.

15. The process of claim 1 wherein the polypeptide having nitrilase activity is derived from a host cell from a genus selected from the group consisting of *Acidovorax*, *Rhodococcus*, *Nocardia*, *Bacillus*, and *Alcaligenes*.

16. The process of claim 1 wherein the enzyme catalyst is in the form of whole microbial cells, permeabilized microbial cells, one or more cell components of a microbial cell extract, partially purified enzyme, or purified enzyme.

17. The process of claim 16 wherein the enzyme catalyst is a transformed microbial host cell selected from the group consisting of *Comamonas* sp., *Corynebacterium* sp., *Brevibacterium* sp., *Rhodococcus* sp., *Azotobacter* sp., *Citrobacter* sp., *Enterobacter* sp., *Clostridium* sp., *Klebsiella* sp., *Salmonella* sp., *Lactobacillus* sp., *Aspergillus* sp., *Saccharomyces* sp., *Yarrowia* sp., *Zygosaccharomyces* sp., *Pichia* sp., *Kluyveromyces* sp., *Candida* sp., *Hansenula* sp., *Dunaliella* sp., *Debaryomyces* sp., *Mucor* sp., *Torulopsis* sp., *Methylobacteria* sp., *Bacillus* sp., *Escherichia* sp., *Pseudomonas* sp., *Rhizobium* sp., and *Streptomyces* sp.

18. The process of claim 17 wherein the transformed microbial host cell is selected from the group consisting of *Bacillus* sp., *Pseudomonas* sp., and *Escherichia* sp.

19. The process of claim 18 wherein the transformed microbial host cell is *Escherichia coli*.

* * * * *

SEQUENCE LISTING

<160> NUMBER OF SEQ ID NOS: 57

<210> SEQ ID NO 1
<211> LENGTH: 12
<212> TYPE: PRT
<213> ORGANISM: artificial sequence
<220> FEATURE:
<223> OTHER INFORMATION: Catalytic signature motif
<220> FEATURE:
<221> NAME/KEY: MISC_FEATURE
<222> LOCATION: (2)..(2)
<223> OTHER INFORMATION: Xaa = Ala or Gly
<220> FEATURE:
<221> NAME/KEY: MISC_FEATURE
<222> LOCATION: (3)..(3)
<223> OTHER INFORMATION: Xaa = Leu, Val, or Ala
<220> FEATURE:
<221> NAME/KEY: MISC_FEATURE
<222> LOCATION: (4)..(3)
<223> OTHER INFORMATION: Xaa = Ala, Asn, Ile, Cys, Val, or Gln;
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa = His or Asn;
<220> FEATURE:
<221> NAME/KEY: MISC_FEATURE
<222> LOCATION: (9)..(9)
<223> OTHER INFORMATION: Xaa = Leu, Tyr, Phe, Ala, Met, Lys, Val, Thr,
    or Arg
<220> FEATURE:
<221> NAME/KEY: MISC_FEATURE
<222> LOCATION: (10)..(10)
<223> OTHER INFORMATION: Xaa = Asn, Gln, Met, Leu, or Ser;
<220> FEATURE:
<221> NAME/KEY: MISC_FEATURE
<222> LOCATION: (11)..(11)
<223> OTHER INFORMATION: Xaa = Pro or Thr
<220> FEATURE:
<221> NAME/KEY: MISC_FEATURE
<222> LOCATION: (12)..(12)
<223> OTHER INFORMATION: Xaa = Leu or Val

<400> SEQUENCE: 1

Gly Xaa Xaa Xaa Cys Trp Glu Xaa Xaa Xaa Xaa Xaa
1               5                   10

<210> SEQ ID NO 2
<211> LENGTH: 12
<212> TYPE: PRT
<213> ORGANISM: artificial sequence
<220> FEATURE:
<223> OTHER INFORMATION: Catalytic sequence motif #2
<220> FEATURE:
<221> NAME/KEY: MISC_FEATURE
<222> LOCATION: (2)..(2)
<223> OTHER INFORMATION: Xaa = Ala or Gly
<220> FEATURE:
<221> NAME/KEY: MISC_FEATURE
<222> LOCATION: (4)..(4)
<223> OTHER INFORMATION: Xaa = Ala or Gly
<220> FEATURE:
<221> NAME/KEY: MISC_FEATURE
<222> LOCATION: (9)..(9)
<223> OTHER INFORMATION: Xaa = Leu, Tyr, Phe, Ala, Met, Lys, Val, Thr,
    or Arg
<220> FEATURE:
<221> NAME/KEY: MISC_FEATURE
<222> LOCATION: (10)..(10)
<223> OTHER INFORMATION: Xaa = Asn, Gln, Met, or Ser -continued

```
<400> SEQUENCE: 2

Gly Xaa Leu Xaa Cys Trp Glu His Xaa Xaa Pro Leu
1               5                   10

<210> SEQ ID NO 3
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)
<220> FEATURE:
<221> NAME/KEY: misc_feature
<222> LOCATION: (1)..(3)
<223> OTHER INFORMATION: Start codon TTG changed to ATG to facilitate
      recombinant expression

<400> SEQUENCE: 3 atg gtt tcg tat aac agc aag ttc ctc gcg gca acc gtt cag gca gag        48
Met Val Ser Tyr Asn Ser Lys Phe Leu Ala Ala Thr Val Gln Ala Glu
1               5                   10                  15 ccg gta tgg ctc gac gca gac gca acg atc gac aag tcg atc ggc atc        96
Pro Val Trp Leu Asp Ala Asp Ala Thr Ile Asp Lys Ser Ile Gly Ile
            20                  25                  30 atc gaa gaa gct gcc caa aag ggc gcg agt ctg atc gct ttc ccg gaa       144
Ile Glu Glu Ala Ala Gln Lys Gly Ala Ser Leu Ile Ala Phe Pro Glu
        35                  40                  45 gta ttc att ccg ggc tac ccc tat tgg gcg tgg ctc ggc gac gtg aag       192
Val Phe Ile Pro Gly Tyr Pro Tyr Trp Ala Trp Leu Gly Asp Val Lys
    50                  55                  60 tac agc cta agc ttt act tca cgc tat cac gag aat tcg ttg gag cta       240
Tyr Ser Leu Ser Phe Thr Ser Arg Tyr His Glu Asn Ser Leu Glu Leu
65                  70                  75                  80 ggt gac gac cgt atg cgt cgc ctc cag ctg gcc gcg cgc cgc aac aaa       288
Gly Asp Asp Arg Met Arg Arg Leu Gln Leu Ala Ala Arg Arg Asn Lys
                85                  90                  95 atc gca ctc gtc atg ggc tat tcg gag cgg gaa gcc gga tcg cgc tat       336
Ile Ala Leu Val Met Gly Tyr Ser Glu Arg Glu Ala Gly Ser Arg Tyr
            100                 105                 110 ctg agc cag gtg ttc atc gac gag cgt ggc gag atc gtt gcc aat cgg       384
Leu Ser Gln Val Phe Ile Asp Glu Arg Gly Glu Ile Val Ala Asn Arg
        115                 120                 125 cgc aag ctg aag ccc aca cac gtt gag cgt acg atc tac ggc gaa ggc       432
Arg Lys Leu Lys Pro Thr His Val Glu Arg Thr Ile Tyr Gly Glu Gly
    130                 135                 140 aac gga acc gat ttc ctc acg cac gac ttc gcg ttc gga cgc gtc ggt       480
Asn Gly Thr Asp Phe Leu Thr His Asp Phe Ala Phe Gly Arg Val Gly
145                 150                 155                 160 gga ttg aac tgc tgg gaa cat ttc caa ccg ctc agc aag ttc atg atg       528
Gly Leu Asn Cys Trp Glu His Phe Gln Pro Leu Ser Lys Phe Met Met
                165                 170                 175 tac agc ctc ggt gag cag gtc cac gtt gca tcg tgg ccg gcg atg tcc       576
Tyr Ser Leu Gly Glu Gln Val His Val Ala Ser Trp Pro Ala Met Ser
            180                 185                 190 cct ctt cag ccg gat gtt ttc caa ctg agc atc gaa gcc aac gcg acg       624
Pro Leu Gln Pro Asp Val Phe Gln Leu Ser Ile Glu Ala Asn Ala Thr
        195                 200                 205 gtc acc cgc tcg tac gca atc gaa ggc caa acc ttt gtg ctt tgc tcg       672
Val Thr Arg Ser Tyr Ala Ile Glu Gly Gln Thr Phe Val Leu Cys Ser
    210                 215                 220 acg cag gtg atc gga cct agc gcg atc gaa acg ttc tgc ctc aac gac       720
Thr Gln Val Ile Gly Pro Ser Ala Ile Glu Thr Phe Cys Leu Asn Asp
```

```
                   225                 230                 235                 240
gaa cag cgc gca ctg ttg ccg caa gga tgt ggc tgg gcg cgc att tac      768
Glu Gln Arg Ala Leu Leu Pro Gln Gly Cys Gly Trp Ala Arg Ile Tyr
                245                 250                 255 ggc ccg gat gga agc gag ctt gcg aag cct ctg gcg gaa gat gct gag      816
Gly Pro Asp Gly Ser Glu Leu Ala Lys Pro Leu Ala Glu Asp Ala Glu
            260                 265                 270 ggg atc ttg tac gca gag atc gat ctg gag cag att ctg ctg gcg aag      864
Gly Ile Leu Tyr Ala Glu Ile Asp Leu Glu Gln Ile Leu Leu Ala Lys
        275                 280                 285 gct gga gcc gat ccg gtc ggg cac tat tcg cgg cct gac gtg ctg tcg      912
Ala Gly Ala Asp Pro Val Gly His Tyr Ser Arg Pro Asp Val Leu Ser
    290                 295                 300 gtc cag ttc gac ccg cgc aat cat acg cca gtt cat cgc atc ggc att      960
Val Gln Phe Asp Pro Arg Asn His Thr Pro Val His Arg Ile Gly Ile
305                 310                 315                 320 gac ggt cgc ttg gat gtg aat acc cgc agt cgc gtg gag aat ttc cga     1008
Asp Gly Arg Leu Asp Val Asn Thr Arg Ser Arg Val Glu Asn Phe Arg
                325                 330                 335 ctg cga caa gcg gct gag cag gag cgt cag gca tcc aag cgg ctc gga     1056
Leu Arg Gln Ala Ala Glu Gln Glu Arg Gln Ala Ser Lys Arg Leu Gly
            340                 345                 350 acg aaa ctc ttt gaa caa tcc ctt ctg gct gaa gaa ccg gtc cca gca     1104
Thr Lys Leu Phe Glu Gln Ser Leu Leu Ala Glu Glu Pro Val Pro Ala
        355                 360                 365 aag tag                                                              1110
Lys
```

<210> SEQ ID NO 4
<211> LENGTH: 369
<212> TYPE: PRT
<213> ORGANISM: Acidovorax facilis 72W

<400> SEQUENCE: 4

```
Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                165                 170                 175

Tyr Ser Leu Gly Glu Gln Val His Val Ala Ser Trp Pro Ala Met Ser
```

-continued

```
                180                 185                 190
Pro Leu Gln Pro Asp Val Phe Gln Leu Ser Ile Glu Ala Asn Ala Thr
            195                 200                 205
Val Thr Arg Ser Tyr Ala Ile Glu Gly Gln Thr Phe Val Leu Cys Ser
        210                 215                 220
Thr Gln Val Ile Gly Pro Ser Ala Ile Glu Thr Phe Cys Leu Asn Asp
225                 230                 235                 240
Glu Gln Arg Ala Leu Leu Pro Gln Gly Cys Gly Trp Ala Arg Ile Tyr
                245                 250                 255
Gly Pro Asp Gly Ser Glu Leu Ala Lys Pro Leu Ala Glu Asp Ala Glu
            260                 265                 270
Gly Ile Leu Tyr Ala Glu Ile Asp Leu Glu Gln Ile Leu Leu Ala Lys
        275                 280                 285
Ala Gly Ala Asp Pro Val Gly His Tyr Ser Arg Pro Asp Val Leu Ser
    290                 295                 300
Val Gln Phe Asp Pro Arg Asn His Thr Pro Val His Arg Ile Gly Ile
305                 310                 315                 320
Asp Gly Arg Leu Asp Val Asn Thr Arg Ser Arg Val Glu Asn Phe Arg
                325                 330                 335
Leu Arg Gln Ala Ala Glu Gln Glu Arg Gln Ala Ser Lys Arg Leu Gly
            340                 345                 350
Thr Lys Leu Phe Glu Gln Ser Leu Leu Ala Glu Glu Pro Val Pro Ala
        355                 360                 365
Lys
```

<210> SEQ ID NO 5
<211> LENGTH: 356
<212> TYPE: PRT
<213> ORGANISM: Alcaligenes faecalis LM3

<400> SEQUENCE: 5

```
Met Gln Thr Arg Lys Ile Val Arg Ala Ala Val Gln Ala Ala Ser
1               5                   10                  15
Pro Asn Tyr Asp Leu Ala Thr Gly Val Asp Lys Thr Ile Glu Leu Ala
                20                  25                  30
Arg Gln Ala Arg Asp Glu Gly Cys Asp Leu Ile Val Phe Gly Glu Thr
            35                  40                  45
Trp Leu Pro Gly Tyr Pro Phe His Val Trp Leu Gly Ala Pro Ala Trp
        50                  55                  60
Ser Leu Lys Tyr Ser Ala Arg Tyr Tyr Ala Asn Ser Leu Ser Leu Asp
65                  70                  75                  80
Ser Ala Glu Phe Gln Arg Ile Ala Gln Ala Ala Arg Thr Leu Gly Ile
                85                  90                  95
Phe Ile Ala Leu Gly Tyr Ser Glu Arg Ser Gly Gly Ser Leu Tyr Leu
            100                 105                 110
Gly Gln Cys Leu Ile Asp Asp Lys Gly Gln Met Leu Trp Ser Arg Arg
        115                 120                 125
Lys Leu Lys Pro Thr His Val Glu Arg Thr Val Phe Gly Glu Gly Tyr
    130                 135                 140
Ala Arg Asp Leu Ile Val Ser Asp Thr Glu Leu Gly Arg Val Gly Ala
145                 150                 155                 160
Leu Cys Cys Trp Glu His Leu Ser Pro Leu Ser Lys Tyr Ala Leu Tyr
                165                 170                 175
Ser Gln His Glu Ala Ile His Ile Ala Ala Trp Pro Ser Phe Ser Leu
```

```
            180                 185                 190
Tyr Ser Glu Gln Ala His Ala Leu Ser Ala Lys Val Asn Met Ala Ala
        195                 200                 205

Ser Gln Ile Tyr Ser Val Glu Gly Gln Cys Phe Thr Ile Ala Ala Ser
    210                 215                 220

Ser Val Thr Gln Glu Thr Leu Asp Met Leu Glu Val Gly Glu His
225                 230                 235                 240

Asn Ala Ser Leu Leu Lys Val Gly Gly Ser Ser Met Ile Phe Ala
            245                 250                 255

Pro Asp Gly Arg Thr Leu Ala Pro Tyr Leu Pro His Asp Ala Glu Gly
        260                 265                 270

Leu Ile Ile Ala Asp Leu Asn Met Glu Glu Ile Ala Phe Ala Lys Ala
        275                 280                 285

Ile Asn Asp Pro Val Gly His Tyr Ser Lys Pro Glu Ala Thr Arg Leu
        290                 295                 300

Val Leu Asp Leu Gly His Arg Glu Pro Met Thr Arg Val His Ser Lys
305                 310                 315                 320

Ser Val Ile Gln Glu Glu Ala Pro Glu Pro His Val Gln Ser Thr Ala
            325                 330                 335

Ala Pro Val Ala Val Ser Gln Thr Gln Asp Ser Asp Thr Leu Leu Val
            340                 345                 350

Gln Glu Pro Ser
        355

<210> SEQ ID NO 6
<211> LENGTH: 366
<212> TYPE: PRT
<213> ORGANISM: Rhodococcus rhodochrous J1

<400> SEQUENCE: 6

Met Val Glu Tyr Thr Asn Thr Phe Lys Val Ala Ala Val Gln Ala Gln
1               5                   10                  15

Pro Val Trp Phe Asp Ala Ala Lys Thr Val Asp Lys Thr Val Ser Ile
            20                  25                  30

Ile Ala Glu Ala Ala Arg Asn Gly Cys Glu Leu Val Ala Phe Pro Glu
        35                  40                  45

Val Phe Ile Pro Gly Tyr Pro Tyr His Ile Trp Val Asp Ser Pro Leu
    50                  55                  60

Ala Gly Met Ala Lys Phe Ala Val Arg Tyr His Glu Asn Ser Leu Thr
65                  70                  75                  80

Met Asp Ser Pro His Val Gln Arg Leu Leu Asp Ala Ala Arg Asp His
                85                  90                  95

Asn Ile Ala Val Val Gly Ile Ser Glu Arg Asp Gly Gly Ser Leu
            100                 105                 110

Tyr Met Thr Gln Leu Val Ile Asp Ala Asp Gly Gln Leu Val Ala Arg
        115                 120                 125

Arg Arg Lys Leu Lys Pro Thr His Val Glu Arg Ser Val Tyr Gly Glu
    130                 135                 140

Gly Asn Gly Ser Asp Ile Ser Val Tyr Asp Met Pro Phe Ala Arg Leu
145                 150                 155                 160

Gly Ala Leu Asn Cys Trp Glu His Phe Gln Thr Leu Thr Lys Tyr Ala
                165                 170                 175

Met Tyr Ser Met His Glu Gln Val His Val Ala Ser Trp Pro Gly Met
            180                 185                 190
```

```
Ser Leu Tyr Gln Pro Glu Val Pro Ala Phe Gly Val Asp Ala Gln Leu
        195                 200                 205

Thr Ala Thr Arg Met Tyr Ala Leu Glu Gly Gln Thr Phe Val Val Cys
    210                 215                 220

Thr Thr Gln Val Val Thr Pro Glu Ala His Glu Phe Phe Cys Asp Asn
225                 230                 235                 240

Asp Glu Gln Arg Lys Leu Ile Gly Arg Gly Gly Phe Ala Arg Ile
            245                 250                 255

Ile Gly Pro Asp Gly Arg Asp Leu Ala Thr Pro Leu Ala Glu Asp Glu
        260                 265                 270

Glu Gly Ile Leu Tyr Ala Asp Ile Asp Leu Ser Ala Ile Thr Leu Ala
            275                 280                 285

Lys Gln Ala Ala Asp Pro Val Gly His Tyr Ser Arg Pro Asp Val Leu
        290                 295                 300

Ser Leu Asn Phe Asn Gln Arg His Thr Thr Pro Val Asn Thr Ala Ile
305                 310                 315                 320

Ser Thr Ile His Ala Thr His Thr Leu Val Pro Gln Ser Gly Ala Leu
            325                 330                 335

Asp Gly Val Arg Glu Leu Asn Gly Ala Asp Glu Gln Arg Ala Leu Pro
        340                 345                 350

Ser Thr His Ser Asp Glu Thr Asp Arg Ala Thr Ala Ser Ile
            355                 360                 365

<210> SEQ ID NO 7
<211> LENGTH: 383
<212> TYPE: PRT
<213> ORGANISM: Rhodococcus rhodochrous K22

<400> SEQUENCE: 7

Met Ser Ser Asn Pro Glu Leu Lys Tyr Thr Gly Lys Val Lys Val Ala
1               5                   10                  15

Thr Val Gln Ala Glu Pro Val Ile Leu Asp Ala Asp Ala Thr Ile Asp
            20                  25                  30

Lys Ala Ile Gly Phe Ile Glu Glu Ala Ala Lys Asn Gly Ala Glu Phe
        35                  40                  45

Leu Ala Phe Pro Glu Val Trp Ile Pro Gly Tyr Pro Tyr Trp Ala Trp
    50                  55                  60

Ile Gly Asp Val Lys Trp Ala Val Ser Asp Phe Ile Pro Lys Tyr His
65                  70                  75                  80

Glu Asn Ser Leu Thr Leu Gly Asp Asp Arg Met Arg Arg Leu Gln Leu
                85                  90                  95

Ala Ala Arg Gln Asn Asn Ile Ala Leu Val Met Gly Tyr Ser Glu Lys
            100                 105                 110

Asp Gly Ala Ser Arg Tyr Leu Ser Gln Val Phe Ile Asp Gln Asn Gly
        115                 120                 125

Asp Ile Val Ala Asn Arg Arg Lys Leu Lys Pro Thr His Val Glu Arg
    130                 135                 140

Thr Ile Tyr Gly Glu Gly Asn Gly Thr Asp Phe Leu Thr His Asp Phe
145                 150                 155                 160

Gly Phe Gly Arg Val Gly Gly Leu Asn Cys Trp Glu His Phe Gln Pro
                165                 170                 175

Leu Ser Lys Tyr Met Met Tyr Ser Leu Asn Glu Gln Ile His Val Ala
            180                 185                 190

Ser Trp Pro Ala Met Phe Ala Leu Thr Pro Asp Val His Gln Leu Ser
        195                 200                 205
```

```
Val Glu Ala Asn Asp Thr Val Thr Arg Ser Tyr Ala Ile Glu Gly Gln
    210                 215                 220

Thr Phe Val Leu Ala Ser Thr His Val Ile Gly Lys Ala Thr Gln Asp
225                 230                 235                 240

Leu Phe Ala Gly Asp Asp Ala Lys Arg Ala Leu Leu Pro Leu Gly
                245                 250                 255

Gln Gly Trp Ala Arg Ile Tyr Gly Pro Asp Gly Lys Ser Leu Ala Glu
                260                 265                 270

Pro Leu Pro Glu Asp Ala Glu Gly Leu Leu Tyr Ala Glu Leu Asp Leu
        275                 280                 285

Glu Gln Ile Ile Leu Ala Lys Ala Ala Asp Pro Ala Gly His Tyr
    290                 295                 300

Ser Arg Pro Asp Val Leu Ser Leu Lys Ile Asp Thr Arg Asn His Thr
305                 310                 315                 320

Pro Val Gln Tyr Ile Thr Ala Asp Gly Arg Thr Ser Leu Asn Ser Asn
                325                 330                 335

Ser Arg Val Glu Asn Tyr Arg Leu His Gln Leu Ala Asp Ile Glu Lys
        340                 345                 350

Tyr Glu Asn Ala Glu Ala Ala Thr Leu Pro Leu Asp Ala Pro Ala Pro
    355                 360                 365

Ala Pro Ala Pro Glu Gln Lys Ser Gly Arg Ala Lys Ala Glu Ala
    370                 375                 380

<210> SEQ ID NO 8
<211> LENGTH: 381
<212> TYPE: PRT
<213> ORGANISM: Norcardia sp. C-14-1

<400> SEQUENCE: 8

Met Lys Val Ala Thr Val Gln Ala Glu Pro Val Ile Leu Asp Ala Asp
1               5                   10                  15

Ala Thr Ile Asp Lys Ala Ile Gly Tyr Ile Glu Glu Ala Ser Lys Asn
                20                  25                  30

Gly Ala Glu Phe Ile Ala Phe Pro Glu Val Trp Ile Pro Gly Tyr Pro
            35                  40                  45

Tyr Trp Ala Trp Ile Gly Asp Val Lys Trp Ala Val Ser Glu Phe Ile
    50                  55                  60

Pro Lys Tyr His Glu Asn Ser Leu Thr Leu Gly Asp Asp Arg Met Arg
65                  70                  75                  80

Arg Leu Gln Leu Ala Ala Arg Gln His Asn Ile Ala Met Val Val Gly
                85                  90                  95

Tyr Ser Glu Lys Asp Gly Ala Ser Arg Tyr Leu Ser Gln Val Phe Ile
                100                 105                 110

Asp Gln Asn Gly Asp Ile Val Ala Asn Arg Arg Lys Leu Lys Pro Thr
            115                 120                 125

His Val Glu Arg Thr Ile Tyr Gly Glu Gly Asn Gly Thr Asp Phe Leu
    130                 135                 140

Thr His Asp Phe Gly Phe Gly Arg Val Gly Gly Leu Asn Cys Trp Glu
145                 150                 155                 160

His Phe Gln Pro Leu Ser Lys Tyr Met Met Tyr Ser Leu Asn Glu Gln
                165                 170                 175

Ile His Val Ala Ser Trp Pro Ala Met Phe Ala Leu Thr Pro Asp Val
            180                 185                 190

His Gln Leu Ser Val Glu Ala Asn Asp Thr Val Thr Arg Ser Tyr Ala
```

-continued

```
        195                 200                 205

Ile Glu Gly Gln Thr Phe Val Leu Ala Ala Thr His Val Ile Gly Lys
    210                 215                 220

Ala Thr Gln Asp Leu Phe Ala Gly Asp Asp Glu Ala Lys Arg Ala Leu
225                 230                 235                 240
Leu Pro Leu Gly Gln Gly Trp Ala Arg Ile Tyr Gly Pro Asp Gly Lys
                245                 250                 255

Ser Leu Ala Glu Pro Leu Ala Glu Asn Ala Glu Gly Leu Leu Tyr Ala
            260                 265                 270

Glu Leu Asp Leu Glu Gln Ile Ile Val Ala Lys Ala Ala Ala Asp Pro
        275                 280                 285

Ala Gly His Tyr Ser Arg Pro Asp Val Leu Ser Leu Lys Val Asp Thr
    290                 295                 300

Arg Asn His Thr Pro Val Gln Tyr Val Thr Glu Asp Gly Gly Ser Ser
305                 310                 315                 320
Leu Asn Ser Asn Ser Arg Val Glu Asn Tyr Arg Leu Arg Gln Leu Ala
                325                 330                 335

Asp Ile Glu Lys Tyr Glu Asn Ala Asp Ser Ala Thr Val Pro Leu Asp
            340                 345                 350
Val Thr Thr Pro Glu Lys Gln Ser Gly Asp Val Asn Ala Asn Gly Asn
        355                 360                 365

Ala Lys Val Asn Thr Asn Pro Ser Ala Lys Ala Lys Ala
    370                 375                 380

<210> SEQ ID NO 9
<211> LENGTH: 310
<212> TYPE: PRT
<213> ORGANISM: Bordetella bronchiseptica RB50

<400> SEQUENCE: 9

Met Thr Thr His Arg Ile Ala Val Ile Gln Asp Gly Pro Val Pro Gly
1               5                   10                  15

Asp Ala Met Ala Thr Ala Glu Lys Met Ser Arg Leu Ala Ala Ser Ala
            20                  25                  30

Lys Ala Gln Gly Ala Arg Leu Ala Leu Phe Pro Glu Ala Phe Val Gly
        35                  40                  45

Gly Tyr Pro Lys Gly Ala Asp Phe His Ile Phe Leu Gly Gly Arg Thr
    50                  55                  60

Pro Gln Gly Arg Ala Gln Tyr Gln Arg Tyr Ala Glu Thr Ala Ile Ala
65                  70                  75                  80

Val Pro Gly Pro Val Thr Glu Arg Ile Gly Gln Ile Ala Ala Glu Gln
                85                  90                  95

Asp Met Phe Ile Val Val Gly Val Ile Glu Arg Asp Gly Gly Thr Leu
            100                 105                 110

Tyr Cys Thr Ile Leu Phe Phe Ser Pro Glu Gly Glu Leu Leu Gly Lys
        115                 120                 125

His Arg Lys Leu Met Pro Thr Ala Leu Glu Arg Leu Leu Trp Gly Tyr
    130                 135                 140

Gly Asp Gly Ser Thr Phe Pro Val Tyr Asp Thr Pro Leu Gly Lys Leu
145                 150                 155                 160

Gly Ala Val Val Cys Trp Glu Asn Tyr Met Pro Leu Leu Arg Met Ala
                165                 170                 175

Met Tyr Gly Lys Gln Ile Gln Ile Tyr Cys Ala Pro Thr Ala Asp Asp
            180                 185                 190
```

```
Lys Pro Thr Trp Val Ser Thr Met Gln His Val Ala Leu Glu Gly Arg
            195                 200                 205

Cys Phe Val Leu Ser Ala Cys Gln His Leu Arg Gly Lys Asp Phe Pro
    210                 215                 220

Pro Glu Phe His Asn Ala Leu Asp Val Gln Pro Asp Thr Val Leu Met
225                 230                 235                 240

Arg Gly Gly Ser Cys Ile Val Asp Pro Met Gly Gln Leu Leu Ala Gly
                245                 250                 255

Pro Val Tyr Asp Glu Asp Ala Ile Leu Val Ala Asp Ile Asp Leu Asp
            260                 265                 270

Ala Val Thr Arg Gly Lys Met Asp Phe Asp Val Val Gly His Tyr Ala
            275                 280                 285

Arg Pro Asp Ile Phe Ser Leu Thr Val Asp Glu Arg Pro Lys Pro Pro
            290                 295                 300

Val Thr Thr Leu Lys Pro
305                 310

<210> SEQ ID NO 10
<211> LENGTH: 339
<212> TYPE: PRT
<213> ORGANISM: Arabidopsis thaliana

<400> SEQUENCE: 10

Met Ser Thr Ser Glu Asn Thr Pro Phe Asn Gly Val Ala Ser Ser Thr
1               5                   10                  15

Ile Val Arg Ala Thr Ile Val Gln Ala Ser Thr Val Tyr Asn Asp Thr
            20                  25                  30

Pro Ala Thr Leu Glu Lys Ala Asn Lys Phe Ile Val Glu Ala Ala Ser
        35                  40                  45

Lys Gly Ser Glu Leu Val Val Phe Pro Glu Ala Phe Ile Gly Gly Tyr
    50                  55                  60

Pro Arg Gly Phe Arg Phe Gly Leu Gly Val Gly Val His Asn Glu Glu
65                  70                  75                  80

Gly Arg Asp Glu Phe Arg Lys Tyr His Ala Ser Ala Ile Lys Val Pro
                85                  90                  95

Gly Pro Glu Val Glu Lys Leu Ala Glu Leu Ala Gly Lys Asn Asn Val
            100                 105                 110

Tyr Leu Val Met Gly Ala Ile Glu Lys Asp Gly Tyr Thr Leu Tyr Cys
        115                 120                 125

Thr Ala Leu Phe Phe Ser Pro Gln Gly Gln Phe Leu Gly Lys His Arg
    130                 135                 140

Lys Leu Met Pro Thr Ser Leu Glu Arg Cys Ile Trp Gly Gln Gly Asp
145                 150                 155                 160

Gly Ser Thr Ile Pro Val Tyr Asp Thr Pro Ile Gly Lys Leu Gly Ala
                165                 170                 175

Ala Ile Cys Trp Glu Asn Arg Met Pro Leu Tyr Arg Thr Ala Leu Tyr
            180                 185                 190

Ala Lys Gly Ile Glu Leu Tyr Cys Ala Pro Thr Ala Asp Gly Ser Lys
        195                 200                 205

Glu Trp Gln Ser Ser Met Leu His Ile Ala Ile Glu Gly Gly Cys Phe
    210                 215                 220

Val Leu Ser Ala Cys Gln Phe Cys Leu Arg Lys Asp Phe Pro Asp His
225                 230                 235                 240

Pro Asp Tyr Leu Phe Thr Asp Trp Tyr Asp Asp Lys Glu Pro Asp Ser
                245                 250                 255
```

```
Ile Val Ser Gln Gly Gly Ser Val Ile Ser Pro Leu Gly Gln Val
            260                 265                 270

Leu Ala Gly Pro Asn Phe Glu Ser Glu Gly Leu Ile Thr Ala Asp Leu
            275                 280                 285

Asp Leu Gly Asp Val Ala Arg Ala Lys Leu Tyr Phe Asp Ser Val Gly
            290                 295                 300

His Tyr Ser Arg Pro Asp Val Leu His Leu Thr Val Asn Glu His Pro
305                 310                 315                 320

Lys Lys Pro Val Thr Phe Ile Ser Lys Val Glu Lys Ala Glu Asp Asp
                325                 330                 335

Ser Asn Lys

<210> SEQ ID NO 11
<211> LENGTH: 334
<212> TYPE: PRT
<213> ORGANISM: Synechococcus elongatus PCC 7942

<400> SEQUENCE: 11

Met Ala Asp Lys Ile Ile Val Ala Ala Gln Ile Arg Pro Val Leu
1               5                   10                  15

Phe Ser Leu Glu Gly Ser Val Ala Arg Val Leu Ala Ala Met Ala Glu
            20                  25                  30

Ala Ala Ala Ala Gly Val Gln Leu Ile Val Phe Pro Glu Thr Phe Leu
        35                  40                  45

Pro Tyr Tyr Pro Tyr Phe Ser Phe Val Glu Pro Val Leu Met Gly
    50                  55                  60

Arg Ser His Leu Lys Leu Tyr Glu Gln Ala Phe Thr Met Thr Gly Pro
65                  70                  75                  80

Glu Leu Gln Gln Ile Ala Arg Ala Ala Arg Gln His Arg Leu Phe Val
                85                  90                  95

Leu Leu Gly Val Asn Glu Arg Asp Gly Gly Ser Leu Tyr Asn Thr Gln
            100                 105                 110

Leu Leu Ile Ser Asp Gln Gly Asp Leu Leu Leu Lys Arg Arg Lys Ile
        115                 120                 125

Thr Pro Thr Tyr His Glu Arg Met Val Trp Gly Gln Gly Gly Gly Ala
    130                 135                 140

Gly Leu Thr Val Val Glu Thr Val Leu Gly Lys Val Gly Ala Leu Ala
145                 150                 155                 160

Cys Trp Glu His Tyr Asn Pro Leu Ala Arg Phe Ser Leu Met Thr Gln
                165                 170                 175

Gly Glu Glu Ile His Cys Ala Gln Phe Pro Gly Ser Leu Val Gly Pro
            180                 185                 190

Ile Phe Ser Glu Gln Thr Ala Val Thr Leu Arg His Ala Leu Glu
        195                 200                 205

Ala Gly Cys Phe Val Leu Ser Ser Thr Ala Trp Leu Asp Pro Ala Asp
    210                 215                 220

Tyr Asp Thr Ile Thr Pro Asp Arg Ser Leu His Lys Ala Phe Gln Gly
225                 230                 235                 240

Gly Cys His Thr Ala Ile Ile Ser Pro Glu Gly Arg Tyr Leu Ala Gly
                245                 250                 255

Pro Leu Pro Glu Gly Glu Gly Leu Ala Ile Ala Glu Leu Asp Lys Ser
            260                 265                 270

Leu Ile Thr Lys Arg Lys Arg Met Met Asp Ser Val Gly His Tyr Ser
        275                 280                 285
```

```
Arg Pro Asp Leu Leu Ser Leu Arg Ile Asn Arg Ser Pro Ala Thr Gln
    290                 295                 300

Val Gln Ala Ile Gly Ser Ala Ala Ala Leu Pro Glu Leu Pro Asn Leu
305                 310                 315                 320

Glu Ala Ala Pro Ala Glu Thr Ala Glu Asp Tyr Leu His Ala
                325                 330

<210> SEQ ID NO 12
<211> LENGTH: 334
<212> TYPE: PRT
<213> ORGANISM: Synechococcus elongatus PCC 6301

<400> SEQUENCE: 12

Met Ala Asp Lys Ile Ile Val Ala Ala Gln Ile Arg Pro Val Leu
1               5                   10                  15

Phe Ser Leu Glu Gly Ser Val Ala Arg Val Leu Ala Ala Met Ala Glu
            20                  25                  30

Ala Ala Ala Ala Gly Val Gln Leu Ile Val Phe Pro Glu Thr Phe Leu
                35                  40                  45

Pro Tyr Tyr Pro Tyr Phe Ser Phe Val Glu Pro Val Leu Met Gly
50                  55                  60

Arg Ser His Leu Lys Leu Tyr Glu Gln Ala Phe Thr Met Thr Gly Pro
65                  70                  75                  80

Glu Leu Gln Gln Ile Ala Arg Ala Ala Arg Gln His Arg Leu Phe Val
                85                  90                  95

Leu Leu Gly Val Asn Glu Arg Asp Gly Gly Ser Leu Tyr Asn Thr Gln
            100                 105                 110

Leu Leu Ile Ser Asp Gln Gly Asp Leu Leu Leu Lys Arg Arg Lys Ile
            115                 120                 125

Thr Pro Thr Tyr His Glu Arg Met Val Trp Gly Gln Gly Gly Gly Ala
    130                 135                 140

Gly Leu Thr Val Val Glu Thr Val Leu Gly Lys Val Gly Ala Leu Ala
145                 150                 155                 160

Cys Trp Glu His Tyr Asn Pro Leu Ala Arg Phe Ser Leu Met Thr Gln
                165                 170                 175

Gly Glu Glu Ile His Cys Ala Gln Phe Pro Gly Ser Leu Val Gly Pro
            180                 185                 190

Ile Phe Ser Glu Gln Thr Ala Val Thr Leu Arg His His Ala Leu Glu
            195                 200                 205

Ala Gly Cys Phe Val Leu Ser Ser Thr Ala Trp Leu Asp Pro Ala Asp
    210                 215                 220

Tyr Asp Thr Ile Thr Pro Asp Arg Ser Leu His Lys Ala Phe Gln Gly
225                 230                 235                 240

Gly Cys His Thr Ala Ile Ile Ser Pro Glu Gly Arg Tyr Leu Ala Gly
                245                 250                 255

Pro Leu Pro Glu Gly Glu Gly Leu Ala Ile Ala Glu Leu Asp Lys Ser
            260                 265                 270

Leu Ile Thr Lys Arg Lys Arg Met Met Asp Ser Val Gly His Tyr Ser
            275                 280                 285

Arg Pro Asp Leu Leu Ser Leu Arg Ile Asn Arg Ser Pro Ala Thr Gln
    290                 295                 300

Val Gln Ala Ile Gly Ser Ala Ala Ala Leu Pro Glu Leu Pro Asn Leu
305                 310                 315                 320

Glu Ala Ala Pro Ala Glu Thr Ala Glu Asp Tyr Leu His Ala
```

```
                    325                 330

<210> SEQ ID NO 13
<211> LENGTH: 346
<212> TYPE: PRT
<213> ORGANISM: Synechocystis sp. PCC 6803

<400> SEQUENCE: 13

Met Leu Gly Lys Ile Met Leu Asn Tyr Thr Lys Asn Ile Arg Ala Ala
1               5                   10                  15

Ala Ala Gln Ile Ser Pro Val Leu Phe Ser Gln Gln Gly Thr Met Glu
            20                  25                  30

Lys Val Leu Asp Ala Ile Ala Asn Ala Ala Lys Lys Gly Val Glu Leu
        35                  40                  45

Ile Val Phe Pro Glu Thr Phe Val Pro Tyr Tyr Pro Tyr Phe Ser Phe
    50                  55                  60

Val Glu Pro Pro Val Leu Met Gly Lys Ser His Leu Lys Leu Tyr Gln
65                  70                  75                  80

Glu Ala Val Thr Val Pro Gly Lys Val Thr Gln Ala Ile Ala Gln Ala
                85                  90                  95

Ala Lys Thr His Gly Met Val Val Leu Gly Val Asn Glu Arg Glu
            100                 105                 110

Glu Gly Ser Leu Tyr Asn Thr Gln Leu Ile Phe Asp Ala Asp Gly Ala
        115                 120                 125

Leu Val Leu Lys Arg Arg Lys Ile Thr Pro Thr Tyr His Glu Arg Met
    130                 135                 140

Val Trp Gly Gln Gly Asp Gly Ala Gly Leu Arg Thr Val Asp Thr Thr
145                 150                 155                 160

Val Gly Arg Leu Gly Ala Leu Ala Cys Trp Glu His Tyr Asn Pro Leu
                165                 170                 175

Ala Arg Tyr Ala Leu Met Ala Gln His Glu Gln Ile His Cys Gly Gln
            180                 185                 190

Phe Pro Gly Ser Met Val Gly Gln Ile Phe Ala Asp Gln Met Glu Val
        195                 200                 205

Thr Met Arg His His Ala Leu Glu Ser Gly Cys Phe Val Ile Asn Ala
    210                 215                 220

Thr Gly Trp Leu Thr Ala Glu Gln Lys Leu Gln Ile Thr Thr Asp Glu
225                 230                 235                 240

Lys Met His Gln Ala Leu Ser Gly Gly Cys Tyr Thr Ala Ile Ile Ser
                245                 250                 255

Pro Glu Gly Lys His Leu Cys Glu Pro Ile Ala Glu Gly Glu Gly Leu
            260                 265                 270

Ala Ile Ala Asp Leu Asp Phe Ser Leu Ile Ala Lys Arg Lys Arg Met
        275                 280                 285

Met Asp Ser Val Gly His Tyr Ala Arg Pro Asp Leu Leu Gln Leu Thr
    290                 295                 300

Leu Asn Asn Gln Pro Trp Ser Ala Leu Glu Ala Asn Pro Val Thr Pro
305                 310                 315                 320

Asn Ala Ile Pro Ala Val Ser Asp Pro Glu Leu Thr Glu Thr Ile Glu
                325                 330                 335

Ala Leu Pro Asn Asn Pro Ile Phe Ser His
            340                 345

<210> SEQ ID NO 14
<211> LENGTH: 307
```

```
<212> TYPE: PRT
<213> ORGANISM: Pseudomonas entomophila L48

<400> SEQUENCE: 14

Met Pro Lys Ser Ile Val Ala Ala Leu Gln Val Gly Ser Leu Pro Glu
1               5                   10                  15

Gly Lys Ala Ala Thr Leu Glu Gln Ile Leu Gly Tyr Glu Gln Ala Ile
            20                  25                  30

Arg Glu Ala Gly Ala Arg Leu Val Met Pro Glu Ala Leu Leu Gly
        35                  40                  45

Gly Tyr Pro Lys Gly Glu Gly Phe Gly Thr Gln Leu Gly Tyr Arg Leu
    50                  55                  60

Pro Glu Gly Arg Glu Ala Phe Ala Arg Tyr Phe Ala Asn Ala Ile Asp
65                  70                  75                  80

Val Pro Gly Ser Glu Thr Ala Ala Leu Ala Gly Leu Ser Ala Arg Thr
                85                  90                  95

Gly Ala Ser Leu Val Leu Gly Val Ile Glu Arg Ser Gly Asn Thr Leu
                100                 105                 110

Tyr Cys Thr Val Leu Phe Phe Glu Pro Glu Gly Gly Leu Val Ala Lys
            115                 120                 125

His Arg Lys Leu Met Pro Thr Gly Thr Glu Arg Leu Ile Trp Gly Lys
        130                 135                 140

Gly Asp Gly Ser Thr Leu Pro Val Val Asp Gly Arg Ala Gly Arg Ile
145                 150                 155                 160

Gly Ala Ala Val Cys Trp Glu Asn Tyr Met Pro Leu Leu Arg Thr Ala
                165                 170                 175

Met Tyr Ala Lys Gly Val Gln Leu Trp Cys Ala Pro Thr Val Asp Glu
            180                 185                 190

Arg Glu Leu Trp Gln Val Ser Met Arg His Val Ala Ala Glu Gly Arg
        195                 200                 205

Cys Phe Val Ile Ser Ala Cys Gln Val Gln Asp Ser Pro Ala Ala Leu
    210                 215                 220

Gly Met Glu Val Ala Asn Trp Pro Ala Glu Arg Pro Leu Ile Asn Gly
225                 230                 235                 240

Gly Ser Leu Ile Val Gly Pro Leu Gly Asp Val Leu Ala Gly Pro Leu
                245                 250                 255

Leu Gly Ala Arg Gly Leu Val Cys Ala Glu Val Asp Thr Asp Glu Leu
            260                 265                 270

Val Arg Ala Arg Tyr Asp Phe Asp Val Val Gly His Tyr Ala Arg Pro
        275                 280                 285

Asp Val Phe Glu Leu Ser Val Asp Glu Arg Pro Arg Pro Gly Val Arg
    290                 295                 300

Phe Ile Gly
305

<210> SEQ ID NO 15
<211> LENGTH: 329
<212> TYPE: PRT
<213> ORGANISM: Zymomonas mobilis subsp. mobilis ZM4

<400> SEQUENCE: 15

Met Ser Cys His Arg Val Ala Val Ile Gln Ala Gly Thr Ser Leu Phe
1               5                   10                  15

Asp Thr Glu Lys Thr Leu Asp Arg Met Glu Ala Leu Cys Arg Gln Ala
            20                  25                  30
```

```
Ala Glu Gln Asn Val Glu Leu Ala Val Phe Pro Glu Ala Tyr Ile Gly
        35                  40                  45

Gly Tyr Pro Lys Gly Leu Asp Phe Gly Ala Arg Met Gly Thr Arg Thr
    50                  55                  60

Glu Ala Gly Arg Glu Asp Phe Leu Arg Tyr Trp Lys Ala Ala Ile Asp
65                  70                  75                  80

Val Pro Gly Lys Glu Thr Ala Arg Ile Gly Ser Phe Ala Ala Lys Met
                85                  90                  95

Lys Ala Tyr Leu Val Val Gly Val Ile Glu Arg Ser Glu Ala Thr Leu
            100                 105                 110

Tyr Cys Thr Ala Leu Phe Phe Ala Pro Asp Gly Thr Leu Ile Gly Lys
        115                 120                 125

His Arg Lys Leu Met Pro Thr Ala Thr Glu Arg Leu Val Trp Gly Gln
    130                 135                 140

Gly Asp Gly Ser Thr Ile Glu Ile Leu Asp Thr Ala Val Gly Lys Leu
145                 150                 155                 160

Gly Ala Ala Ile Cys Trp Glu Asn Tyr Met Pro Val Leu Arg Gln Val
                165                 170                 175

Met Tyr Ala Gly Gly Val Asn Ile Trp Cys Ala Pro Thr Val Asp Gln
            180                 185                 190

Arg Glu Ile Trp Gln Val Ser Met Arg His Ile Ala Tyr Glu Gly Arg
        195                 200                 205

Leu Phe Val Leu Ser Ala Cys Gln Tyr Met Thr Arg Ala Asp Ala Pro
    210                 215                 220

Ala Asp Tyr Asp Cys Ile Gln Gly Asn Asp Pro Glu Thr Glu Leu Ile
225                 230                 235                 240

Ala Gly Gly Ser Val Ile Ile Asp Pro Met Gly Asn Ile Leu Ala Gly
                245                 250                 255

Pro Leu Tyr Gly Gln Glu Gly Val Leu Val Ala Asp Ile Asp Leu Ser
            260                 265                 270

Asp Thr Ile Lys Ala Arg Tyr Asp Leu Asp Val Ser Gly His Tyr Gly
        275                 280                 285

Arg Pro Asp Ile Phe Glu Ile Lys Val Asp Arg Gln Ser His Gln Val
    290                 295                 300

Ile Thr Asp Gln Phe Ser Arg Asp Gln Ala Thr Glu Lys Lys Pro Val
305                 310                 315                 320

Ser Asp Ser Glu Ile Ser Gln Leu Asp
                325

<210> SEQ ID NO 16
<211> LENGTH: 339
<212> TYPE: PRT
<213> ORGANISM: Bacillus sp. OxB-1

<400> SEQUENCE: 16

Met Ser Asn Tyr Pro Lys Tyr Arg Val Ala Ala Val Gln Ala Ser Pro
1               5                   10                  15

Val Leu Leu Asp Leu Asp Ala Thr Ile Asp Lys Thr Cys Arg Leu Val
            20                  25                  30

Asp Glu Ala Ala Ala Asn Gly Ala Lys Val Ile Ala Phe Pro Glu Ala
        35                  40                  45

Phe Ile Pro Gly Tyr Pro Trp Trp Ile Trp Leu Gly Asn Ala Asp Tyr
    50                  55                  60

Gly Met Lys Tyr Tyr Ile Gln Leu Tyr Lys Asn Ser Val Glu Ile Pro
65                  70                  75                  80
```

```
Ser Leu Ala Val Gln Lys Leu Ser Ser Ala Gly Thr Asn Lys Val Tyr
                85                  90                  95

Phe Cys Val Ser Val Thr Glu Lys Asp Gly Gly Ser Leu Tyr Leu Thr
            100                 105                 110

Gln Leu Trp Phe Asp Pro Asn Gly Asp Leu Ile Gly Lys His Arg Lys
        115                 120                 125

Leu Lys Ala Thr Asn Ala Glu Lys Thr Ile Trp Gly Asp Gly Asp Gly
    130                 135                 140

Ser Met Met Pro Val Phe Glu Thr Glu Phe Gly Asn Leu Gly Gly Leu
145                 150                 155                 160

Gln Cys Trp Glu His Phe Leu Pro Leu Asn Val Ala Ala Met Ala Ser
                165                 170                 175

Met Asn Glu Gln Val His Val Ala Ser Trp Pro Ile Gly Met Pro Gln
            180                 185                 190

Glu Gly His Leu Phe Gly Pro Glu Gln Cys Val Thr Ala Thr Lys Tyr
        195                 200                 205

Tyr Ala Ile Ser Asn Gln Val Phe Cys Leu Leu Ser Ser Gln Ile Trp
    210                 215                 220

Thr Glu Glu Gln Arg Asp Lys Ile Cys Glu Thr Glu Glu Gln Arg Asn
225                 230                 235                 240

Phe Met Lys Val Gly His Gly Phe Ser Lys Ile Ile Ala Pro Asn Gly
                245                 250                 255

Met Glu Ile Gly Asn Lys Leu Ala His Asp Glu Glu Gly Ile Thr Tyr
            260                 265                 270

Ala Asp Ile Asp Leu Glu Gln Ile Ile Pro Gly Lys Phe Leu Ile Asp
        275                 280                 285

Ser Ala Gly His Tyr Ser Thr Pro Gly Phe Leu Ser Leu Ser Phe Asp
    290                 295                 300

Arg Thr Glu Lys Lys Pro Ile Lys His Ile Gly Glu Ser Ala Gln Glu
305                 310                 315                 320

Thr Val Thr Tyr Glu Glu Ile Gln Tyr Gly Asn Lys Ala Asn Val Lys
                325                 330                 335

Val His Ser

<210> SEQ ID NO 17
<211> LENGTH: 354
<212> TYPE: PRT
<213> ORGANISM: Comamonas testosterone

<400> SEQUENCE: 17

Met Lys Asn Tyr Pro Thr Val Lys Val Ala Ala Val Gln Ala Ala Pro
1               5                   10                  15

Val Phe Met Asn Leu Glu Ala Thr Val Asp Lys Thr Cys Lys Leu Ile
            20                  25                  30

Ala Glu Ala Ala Ser Met Gly Ala Lys Val Ile Gly Phe Pro Glu Ala
        35                  40                  45

Phe Ile Pro Gly Tyr Pro Tyr Trp Ile Trp Thr Ser Asn Met Asp Phe
    50                  55                  60

Thr Gly Met Met Trp Ala Val Leu Phe Lys Asn Ala Ile Glu Ile Pro
65                  70                  75                  80

Ser Lys Glu Val Gln Gln Ile Ser Asp Ala Ala Lys Lys Asn Gly Val
                85                  90                  95

Tyr Val Cys Val Ser Val Ser Glu Lys Asp Asn Ala Ser Leu Tyr Leu
            100                 105                 110
```

```
Thr Gln Leu Trp Phe Asp Pro Asn Gly Asn Leu Ile Gly Lys His Arg
            115                 120                 125

Lys Phe Lys Pro Thr Ser Ser Glu Arg Ala Val Trp Gly Asp Gly Asp
130                 135                 140

Gly Ser Met Ala Pro Val Phe Lys Thr Glu Tyr Gly Asn Leu Gly Gly
145                 150                 155                 160

Leu Gln Cys Trp Glu His Ala Leu Pro Leu Asn Ile Ala Ala Met Gly
            165                 170                 175

Ser Leu Asn Glu Gln Val His Val Ala Ser Trp Pro Ala Phe Val Pro
            180                 185                 190

Lys Gly Ala Val Ser Ser Arg Val Ser Ser Val Cys Ala Ser Thr
195                 200                 205

Asn Ala Met His Gln Ile Ile Ser Gln Phe Tyr Ala Ile Ser Asn Gln
            210                 215                 220

Val Tyr Val Ile Met Ser Thr Asn Leu Val Gly Gln Asp Met Ile Asp
225                 230                 235                 240

Met Ile Gly Lys Asp Glu Phe Ser Lys Asn Phe Leu Pro Leu Gly Ser
            245                 250                 255

Gly Asn Thr Ala Ile Ile Ser Asn Thr Gly Glu Ile Leu Ala Ser Ile
            260                 265                 270

Pro Gln Asp Ala Glu Gly Ile Ala Val Ala Glu Ile Asp Leu Asn Gln
            275                 280                 285

Ile Ile Tyr Gly Lys Trp Leu Leu Asp Pro Ala Gly His Tyr Ser Thr
            290                 295                 300

Pro Gly Phe Leu Ser Leu Thr Phe Asp Gln Ser Glu His Val Pro Val
305                 310                 315                 320

Lys Lys Ile Gly Glu Gln Thr Asn His Phe Ile Ser Tyr Glu Asp Leu
            325                 330                 335

His Glu Asp Lys Met Asp Met Leu Thr Ile Pro Pro Arg Arg Val Ala
            340                 345                 350

Thr Ala

<210> SEQ ID NO 18
<211> LENGTH: 332
<212> TYPE: PRT
<213> ORGANISM: Synechococcus sp. CC9605

<400> SEQUENCE: 18

Met Thr Thr Val Lys Val Ala Ala Ala Gln Ile Arg Pro Val Leu Phe
1               5                   10                  15

Ser Leu Asp Gly Ser Leu Gln Lys Val Leu Asp Ala Met Ala Glu Ala
            20                  25                  30

Ala Ala Gln Gly Val Glu Leu Ile Val Phe Pro Glu Thr Phe Leu Pro
            35                  40                  45

Tyr Tyr Pro Tyr Phe Ser Phe Val Glu Pro Pro Val Leu Met Gly Arg
        50                  55                  60

Ser His Leu Ala Leu Tyr Glu Gln Ala Val Val Pro Gly Pro Val
65                  70                  75                  80

Thr Asp Ala Val Ala Ala Ala Ser Gln Tyr Gly Met Gln Val Leu
            85                  90                  95

Leu Gly Val Asn Glu Arg Asp Gly Gly Thr Leu Tyr Asn Thr Gln Leu
            100                 105                 110

Leu Phe Asn Ser Cys Gly Glu Leu Val Leu Lys Arg Arg Lys Ile Thr
            115                 120                 125
```

```
Pro Thr Tyr His Glu Arg Met Val Trp Gly Gln Gly Asp Gly Ser Gly
            130                 135                 140

Leu Lys Val Val Gln Thr Pro Leu Ala Arg Val Gly Ala Leu Ala Cys
145                 150                 155                 160

Trp Glu His Tyr Asn Pro Leu Ala Arg Tyr Ala Leu Met Ala Gln Gly
                165                 170                 175

Glu Glu Ile His Cys Ala Gln Phe Pro Gly Ser Leu Val Gly Pro Ile
            180                 185                 190

Phe Thr Glu Gln Thr Ala Val Thr Met Arg His His Ala Leu Glu Ala
                195                 200                 205

Gly Cys Phe Val Ile Cys Ser Thr Gly Trp Leu His Pro Asp Asp Tyr
            210                 215                 220

Ala Ser Ile Thr Ser Glu Ser Gly Leu His Lys Ala Phe Gln Gly Gly
225                 230                 235                 240

Cys His Thr Ala Val Ile Ser Pro Glu Gly Arg Tyr Leu Ala Gly Pro
                245                 250                 255

Leu Pro Asp Gly Glu Gly Leu Ala Ile Ala Asp Leu Asp Leu Ala Leu
            260                 265                 270

Ile Thr Lys Arg Lys Met Met Asp Ser Val Gly His Tyr Ser Arg
            275                 280                 285

Pro Glu Leu Leu Ser Leu Gln Ile Asn Ser Ser Pro Ala Val Pro Val
            290                 295                 300

Gln Asn Met Ser Thr Ala Ser Val Pro Leu Glu Pro Ala Thr Ala Thr
305                 310                 315                 320

Asp Ala Leu Ser Ser Met Glu Ala Leu Asn His Val
                325                 330

<210> SEQ ID NO 19
<211> LENGTH: 306
<212> TYPE: PRT
<213> ORGANISM: Pseudomonas fluorescens Pf-5

<400> SEQUENCE: 19

Met Pro Lys Ser Val Val Ala Ala Leu Gln Ile Gly Ala Leu Pro Glu
1               5                   10                  15

Gly Lys Ala Ala Thr Leu Glu Gln Ile Leu Ser Tyr Glu Ala Ala Ile
                20                  25                  30

Ile Glu Ala Gly Ala Gln Leu Val Val Met Pro Glu Ala Leu Leu Gly
            35                  40                  45

Gly Tyr Pro Lys Gly Glu Gly Phe Gly Thr Gln Leu Gly Tyr Arg Leu
        50                  55                  60

Pro Glu Gly Arg Glu Ala Phe Ala Arg Tyr Phe Ala Asn Ala Ile Glu
65                  70                  75                  80

Val Pro Gly Val Glu Thr Asp Ala Leu Ala Ala Leu Ser Ala Arg Thr
                85                  90                  95

Gly Ala Asn Leu Val Leu Gly Val Ile Glu Arg Ser Gly Ser Thr Leu
            100                 105                 110

Tyr Cys Thr Ala Leu Tyr Phe Asp Pro Gln Gln Gly Leu Ser Gly Lys
        115                 120                 125

His Arg Lys Leu Met Pro Thr Gly Thr Glu Arg Leu Ile Trp Gly Lys
130                 135                 140

Gly Asp Gly Ser Thr Leu Pro Val Leu Asp Thr Gln Val Gly Arg Val
145                 150                 155                 160

Gly Ala Val Ile Cys Trp Glu Asn Met Met Pro Leu Leu Arg Thr Ala
```

-continued

```
                165                 170                 175
Met Tyr Ala Gln Gly Ile Glu Val Trp Cys Ala Pro Thr Val Asp Glu
            180                 185                 190

Arg Glu Met Trp Gln Val Ser Met Arg His Ile Ala His Glu Gly Arg
        195                 200                 205

Cys Phe Val Val Ser Ala Cys Gln Val Gln Ala Ser Pro Glu Glu Leu
    210                 215                 220

Gly Leu Glu Ile Ala Asn Trp Pro Ala Gln Arg Pro Leu Ile Ala Gly
225                 230                 235                 240

Gly Ser Val Ile Val Gly Pro Met Gly Asp Val Leu Ala Gly Pro Leu
                245                 250                 255

Val Gly Arg Ala Gly Leu Ile Ser Ala Gln Ile Asp Thr Ala Asp Leu
            260                 265                 270

Val Arg Ala Arg Tyr Asp Tyr Asp Val Val Gly His Tyr Ala Arg Pro
        275                 280                 285

Asp Val Phe Glu Leu Thr Val Asp Gln Arg Pro Arg Pro Gly Val Arg
    290                 295                 300

Phe Thr
305
```

<210> SEQ ID NO 20
<211> LENGTH: 336
<212> TYPE: PRT
<213> ORGANISM: Nocardia farcinica IFM 10152]

<400> SEQUENCE: 20

```
Met Ser Gln Arg Asp Ser Phe Arg Ala Ala Val Gln Ala Pro
1               5                   10                  15

Val Trp Leu Asp Gly Ala Ala Thr Val Asp Lys Cys Val Ala Leu Ile
            20                  25                  30

Glu Glu Ala Ala Asp Asn Gly Ala Ala Leu Ile Ala Phe Pro Glu Thr
        35                  40                  45

Phe Val Pro Gly Tyr Pro Trp Trp Leu Trp Leu Asp Ser Pro Ala Trp
    50                  55                  60

Gly Met Gln Phe Val Ala Arg Tyr Phe Asp Asn Ser Leu Ala Leu Asp
65                  70                  75                  80

Gly Pro Leu Phe Ala Arg Leu Arg Glu Ala Ala Arg Arg Ser Ala Ile
                85                  90                  95

Thr Val Val Thr Gly His Ser Glu Arg Asp Gly Gly Ser Leu Tyr Met
            100                 105                 110

Gly Gln Ala Ile Ile Gly Ala Asp Gly Glu Val Leu Ala Ala Arg Arg
        115                 120                 125

Lys Leu Lys Pro Thr His Val Glu Arg Thr Val Phe Gly Glu Ser Asp
    130                 135                 140

Gly Ser Asn Leu Thr Val Val Asp Thr Glu Leu Gly Arg Leu Gly Ala
145                 150                 155                 160

Leu Cys Cys Trp Glu His Leu Gln Pro Leu Thr Lys Tyr Ala Met Tyr
                165                 170                 175

Ser Gln His Glu Gln Ile His Val Ala Ala Trp Pro Ser Phe Ser Val
            180                 185                 190

Tyr Arg Gly Ala Ala Tyr Ala Leu Gly Pro Glu Val Asn Thr Gly Ala
        195                 200                 205

Ala Arg Gln Tyr Ala Val Glu Gly Gln Cys Phe Val Leu Ser Pro Cys
    210                 215                 220
```

```
Ala Val Ile Asp Glu Ala Gly Val Glu Leu Phe Cys Asp Thr Pro Ala
225                 230                 235                 240

Lys Arg Glu Leu Leu Leu Pro Gly Gly Gly Phe Ala Gln Ile Tyr Gly
            245                 250                 255

Pro Asp Gly Arg Glu Leu Gly Thr Ala Leu Pro Glu Thr Glu Glu Gly
        260                 265                 270

Leu Val Tyr Ala Asp Leu Glu Ala Ser Ala Val Ala Val Ala Lys Ser
    275                 280                 285

Ala Ala Asp Pro Val Gly His Tyr Ser Arg Pro Asp Val Leu Gln Leu
290                 295                 300

Leu Trp Asp Pro Arg Pro Arg Ser Val Val Arg Gln Val Ala Leu Ser
305                 310                 315                 320

Val Ala Ser Pro Ala Glu Ser Asp Asp Ala Glu Pro Ala Val Arg
            325                 330                 335

<210> SEQ ID NO 21
<211> LENGTH: 356
<212> TYPE: PRT
<213> ORGANISM: Alcaligenes faecalis 1650

<400> SEQUENCE: 21

Met Gln Thr Arg Lys Ile Val Arg Ala Ala Val Gln Ala Ala Ser
1               5                   10                  15

Pro Asn Tyr Asp Leu Ala Thr Gly Val Asp Lys Thr Ile Glu Leu Ala
            20                  25                  30

Arg Gln Ala Arg Asp Glu Gly Cys Asp Leu Ile Val Phe Gly Glu Thr
        35                  40                  45

Trp Leu Pro Gly Tyr Pro Phe His Val Trp Leu Gly Ala Pro Ala Trp
50                  55                  60

Ser Leu Lys Tyr Ser Ala Arg Tyr Tyr Ala Asn Ser Leu Ser Leu Asp
65                  70                  75                  80

Ser Ala Glu Phe Gln Arg Ile Ala Gln Ala Ala Arg Thr Leu Gly Ile
                85                  90                  95

Phe Ile Ala Leu Gly Tyr Ser Glu Arg Ser Gly Gly Ser Leu Tyr Leu
            100                 105                 110

Gly Gln Cys Leu Ile Asp Asp Lys Gly Glu Met Leu Trp Ser Arg Arg
        115                 120                 125

Lys Leu Lys Pro Thr His Val Glu Arg Thr Val Phe Gly Glu Gly Tyr
130                 135                 140

Ala Arg Asp Leu Ile Val Ser Asp Thr Glu Leu Gly Arg Val Gly Ala
145                 150                 155                 160

Leu Cys Cys Trp Glu His Leu Ser Pro Leu Ser Lys Tyr Ala Leu Tyr
                165                 170                 175

Ser Gln His Glu Ala Ile His Ile Ala Ala Trp Pro Ser Phe Ser Leu
            180                 185                 190

Tyr Ser Glu Gln Ala His Ala Leu Ser Ala Lys Val Asn Met Ala Ala
        195                 200                 205

Ser Gln Ile Tyr Ser Val Glu Gly Gln Cys Phe Thr Ile Ala Ala Ser
210                 215                 220

Ser Val Val Thr Gln Glu Thr Leu Asp Met Leu Glu Val Gly Glu His
225                 230                 235                 240

Asn Ala Pro Leu Leu Lys Val Gly Gly Gly Ser Ser Met Ile Phe Ala
                245                 250                 255

Pro Asp Gly Arg Thr Leu Ala Pro Tyr Leu Pro His Asp Ala Glu Gly
            260                 265                 270
```

```
Leu Ile Ile Ala Asp Leu Asn Met Glu Glu Ile Ala Phe Ala Lys Ala
            275                 280                 285

Ile Asn Asp Pro Val Gly His Tyr Ser Lys Pro Glu Ala Thr Arg Leu
        290                 295                 300

Val Leu Asp Leu Gly His Arg Asp Pro Met Thr Arg Val His Ser Lys
305                 310                 315                 320

Ser Val Thr Arg Glu Glu Ala Pro Glu Gln Gly Val Gln Ser Lys Ile
                325                 330                 335

Ala Ser Val Ala Ile Ser His Pro Gln Asp Ser Asp Thr Leu Leu Val
            340                 345                 350

Gln Glu Pro Ser
        355

<210> SEQ ID NO 22
<211> LENGTH: 336
<212> TYPE: PRT
<213> ORGANISM: Pseudomonas syringae pv. syringae B728a

<400> SEQUENCE: 22

Met Lys Glu Pro Leu Lys Val Ala Cys Val Gln Ala Ala Pro Val Phe
1               5                   10                  15

Leu Asp Leu Asp Ala Thr Val Asp Lys Thr Ile Thr Leu Met Glu Gln
            20                  25                  30

Ala Ala Ala Ala Gly Ala Gly Leu Ile Ala Phe Pro Glu Thr Trp Ile
        35                  40                  45

Pro Gly Tyr Pro Trp Phe Leu Trp Leu Asp Ala Pro Ala Trp Asn Met
    50                  55                  60

Pro Leu Val Gln Arg Tyr His Gln Gln Ser Leu Val Leu Asp Ser Val
65                  70                  75                  80

Gln Ala Arg Arg Ile Ser Asp Ala Ala Arg His Leu Gly Leu Tyr Val
                85                  90                  95

Val Leu Gly Tyr Ser Glu Arg Asn Lys Ala Ser Leu Tyr Ile Gly Gln
            100                 105                 110

Trp Ile Ile Asp Asp His Gly Glu Thr Val Gly Val Arg Arg Lys Leu
        115                 120                 125

Lys Ala Thr His Val Glu Arg Thr Met Phe Gly Glu Gly Asp Gly Ala
130                 135                 140

Ser Leu Arg Thr Phe Glu Thr Pro Val Gly Val Leu Gly Ala Leu Cys
145                 150                 155                 160

Cys Trp Glu His Leu Gln Pro Leu Ser Lys Tyr Ala Met Tyr Ala Gln
                165                 170                 175

Asn Glu Gln Ile His Val Ala Ala Trp Pro Ser Phe Ser Leu Tyr Arg
            180                 185                 190

Asn Ala Thr Ser Ala Leu Gly Pro Glu Val Asn Thr Ala Ala Ser Arg
        195                 200                 205

Val Tyr Ala Ala Glu Gly Gln Cys Phe Val Leu Ala Pro Cys Ala Ile
    210                 215                 220

Val Ser Pro Glu Met Ile Glu Met Leu Cys Asp Ser Asp Ala Lys Arg
225                 230                 235                 240

Ser Leu Leu Gln Ala Gly Gly His Ala Arg Ile Phe Gly Pro Asp
                245                 250                 255

Gly Ser Asp Leu Ala Thr Pro Leu Gly Glu His Glu Glu Gly Leu Leu
            260                 265                 270

Tyr Ala Thr Leu Asp Pro Ala Ala Leu Thr Leu Ala Lys Val Ala Ala
```

-continued

Asp Pro Ala Gly His Tyr Ser Arg Pro Asp Val Thr Arg Leu Met Phe
       290                 295                 300

Asn Pro Asn Pro Thr Pro Cys Val Val Asp Leu Pro Asp Leu Pro Ile
305                 310                 315                 320

Ser Ser Glu Ser Ile Glu Leu Leu Arg Pro Asp Ile Ala Leu Glu Val
              325                 330                 335

<210> SEQ ID NO 23
<211> LENGTH: 345
<212> TYPE: PRT
<213> ORGANISM: Bradyrhizobium sp. BTAi1

<400> SEQUENCE: 23

Met Gly Leu Ala His Pro Lys Tyr Lys Val Ala Val Gln Ala Ala
1               5                   10                  15

Pro Ala Trp Leu Asp Leu Asp Ala Ser Ile Lys Lys Thr Ile Ala Leu
              20                  25                  30

Ile Glu Glu Ala Ala Asp Lys Gly Ala Lys Leu Ile Ala Phe Pro Glu
              35                  40                  45

Val Phe Ile Pro Gly Tyr Pro Trp His Ile Trp Met Asp Ser Pro Ala
50                  55                  60

Trp Cys Ile Gly Arg Gly Phe Val Gln Arg Tyr Phe Asp Asn Ser Leu
65                  70                  75                  80

Ala Tyr Asp Ser Pro Gln Ala Glu Ala Leu Arg Ala Ala Val Arg Lys
                85                  90                  95

Ala Gln Leu Thr Ala Val Leu Gly Leu Ser Glu Arg Asp Gly Gly Ser
              100                 105                 110

Leu Tyr Ile Ala Gln Trp Leu Ile Gly Ala Asp Gly Glu Thr Ile Ala
          115                 120                 125

Lys Arg Arg Lys Leu Arg Pro Thr His Ala Glu Arg Thr Val Tyr Gly
130                 135                 140

Glu Gly Asp Gly Ser Asp Leu Ala Val His Glu Arg Pro Asp Ile Gly
145                 150                 155                 160

Arg Ile Gly Ala Leu Cys Cys Trp Glu His Leu Gln Pro Leu Ser Lys
                165                 170                 175

Tyr Ala Met Tyr Ala Gln Asn Glu Gln Val His Val Ala Ala Trp Pro
              180                 185                 190

Ser Phe Ser Leu Tyr Asp Pro Phe Ala Pro Ala Leu Gly Ala Glu Val
          195                 200                 205

Asn Asn Ala Ala Ser Arg Val Tyr Ala Val Glu Gly Ser Cys Phe Val
210                 215                 220

Leu Ala Pro Cys Ala Thr Val Ser Gln Ala Met Ile Asp Glu Leu Cys
225                 230                 235                 240

Asp Arg Pro Asp Lys His Ala Leu Leu His Ala Gly Gly Gly His Ala
                245                 250                 255

Ala Ile Phe Gly Pro Asp Gly Ser Ala Leu Ala Gln Leu Pro Pro
              260                 265                 270

Asp Gln Glu Gly Leu Leu Ile Ala Glu Ile Asp Leu Gly Met Ile Gly
          275                 280                 285

Ile Ala Lys Asn Ala Ala Asp Pro Ala Gly His Tyr Ser Arg Pro Asp
      290                 295                 300

Val Thr Arg Leu Leu Leu Asn Lys Lys Pro Leu Asn Arg Val Glu His
305                 310                 315                 320

-continued

Phe Ser Leu Pro Val Asp Ser Ala Ala Ala Leu Pro Gly Glu Ala
              325                 330                 335

Ala Val Ala Arg Pro Asp Gln Ser Ile
        340                 345

<210> SEQ ID NO 24
<211> LENGTH: 366
<212> TYPE: PRT
<213> ORGANISM: Rhodococcus rhodochrous NCIMB 11216

<400> SEQUENCE: 24

Met Val Glu Tyr Thr Asn Thr Phe Lys Val Ala Val Gln Ala Gln
1               5                   10                  15

Pro Val Trp Phe Asp Ala Ala Lys Thr Val Asp Lys Thr Val Ser Ile
            20                  25                  30

Ile Ala Glu Ala Ala Arg Asn Gly Cys Glu Leu Val Ala Phe Pro Glu
        35                  40                  45

Val Phe Ile Pro Gly Tyr Pro Tyr His Ile Trp Val Asp Ser Pro Leu
    50                  55                  60

Ala Gly Met Ala Lys Phe Ala Val Arg Tyr His Glu Asn Ser Leu Thr
65                  70                  75                  80

Met Asp Ser Pro His Val Gln Arg Leu Leu Asp Ala Ala Arg Asp His
                85                  90                  95

Asn Ile Ala Val Val Gly Ile Ser Glu Arg Asp Gly Gly Ser Leu
            100                 105                 110

Tyr Met Thr Gln Leu Ile Ile Asp Ala Asp Gly Gln Leu Val Ala Arg
        115                 120                 125

Arg Arg Lys Leu Lys Pro Thr His Val Glu Arg Ser Val Tyr Gly Glu
130                 135                 140

Gly Asn Gly Ser Asp Ile Ser Val Tyr Asp Met Pro Phe Ala Arg Leu
145                 150                 155                 160

Gly Ala Leu Asn Cys Trp Glu His Phe Gln Thr Leu Thr Lys Tyr Ala
                165                 170                 175

Met Tyr Ser Met His Glu Gln Val His Val Ala Ser Trp Pro Gly Met
            180                 185                 190

Ser Leu Tyr Gln Pro Glu Val Pro Ala Phe Gly Val Asp Ala Gln Leu
        195                 200                 205

Thr Ala Thr Arg Met Tyr Ala Leu Glu Gly Gln Thr Phe Val Val Cys
    210                 215                 220

Thr Thr Gln Val Val Thr Pro Glu Ala His Glu Phe Phe Cys Glu Asn
225                 230                 235                 240

Glu Glu Gln Arg Lys Leu Ile Gly Arg Gly Gly Gly Phe Ala Arg Ile
                245                 250                 255

Ile Gly Pro Asp Gly Arg Asp Leu Ala Thr Pro Leu Ala Glu Asp Glu
            260                 265                 270

Glu Gly Ile Leu Tyr Ala Asp Ile Asp Leu Ser Ala Ile Thr Leu Ala
        275                 280                 285

Lys Gln Ala Ala Asp Pro Val Gly His Tyr Ser Arg Pro Asp Val Leu
    290                 295                 300

Ser Leu Asn Phe Asn Gln Arg Arg Thr Thr Pro Val Asn Thr Pro Leu
305                 310                 315                 320

Ser Thr Ile His Ala Thr His Thr Phe Val Pro Gln Phe Gly Ala Leu
                325                 330                 335

Asp Gly Val Arg Glu Leu Asn Gly Ala Asp Glu Gln Arg Ala Leu Pro
            340                 345                 350

Ser Thr His Ser Asp Glu Thr Asp Arg Ala Thr Ala Thr Leu
          355                 360                 365

<210> SEQ ID NO 25
<211> LENGTH: 366
<212> TYPE: PRT
<213> ORGANISM: Rhodococcus rhodochrous ATCC 39484

<400> SEQUENCE: 25

Met Val Glu Tyr Thr Asn Thr Phe Lys Val Ala Ala Val Gln Ala Gln
1               5                   10                  15

Pro Val Trp Phe Asp Ala Ala Lys Thr Val Asp Lys Thr Val Ser Ile
            20                  25                  30

Ile Ala Glu Ala Ala Arg Asn Gly Cys Glu Leu Val Ala Phe Pro Glu
        35                  40                  45

Val Phe Ile Pro Gly Tyr Pro Tyr His Ile Trp Val Asp Ser Pro Leu
    50                  55                  60

Ala Gly Met Ala Lys Phe Ala Val Arg Tyr His Glu Asn Ser Leu Thr
65                  70                  75                  80

Met Asp Ser Pro His Val Gln Arg Leu Leu Asp Ala Ala Arg Asp His
                85                  90                  95

Asn Ile Ala Val Val Gly Ile Ser Glu Arg Asp Gly Gly Ser Leu
            100                 105                 110

Tyr Met Thr Gln Leu Ile Ile Asp Ala Asp Gly Gln Leu Val Ala Arg
        115                 120                 125

Arg Arg Lys Leu Lys Pro Thr His Val Glu Arg Ser Val Tyr Gly Glu
    130                 135                 140

Gly Asn Gly Ser Asp Ile Ser Val Tyr Asp Met Pro Phe Ala Arg Leu
145                 150                 155                 160

Gly Ala Leu Asn Cys Trp Glu His Phe Gln Thr Leu Thr Lys Tyr Ala
                165                 170                 175

Met Tyr Ser Met His Glu Gln Val His Val Ala Ser Trp Pro Gly Met
            180                 185                 190

Ser Leu Tyr Gln Pro Glu Val Pro Ala Phe Gly Val Asp Ala Gln Leu
        195                 200                 205

Thr Ala Thr Arg Met Tyr Ala Leu Glu Gly Gln Thr Phe Val Val Cys
    210                 215                 220

Thr Thr Gln Val Val Thr Pro Glu Ala His Glu Phe Phe Cys Glu Asn
225                 230                 235                 240

Glu Glu Gln Arg Met Leu Ile Gly Arg Gly Gly Phe Ala Arg Ile
                245                 250                 255

Ile Gly Pro Asp Gly Arg Asp Leu Ala Thr Pro Leu Ala Glu Asp Glu
            260                 265                 270

Glu Gly Ile Leu Tyr Ala Asp Ile Asp Leu Ser Ala Ile Thr Leu Ala
        275                 280                 285

Lys Gln Ala Ala Asp Pro Val Gly His Tyr Ser Arg Pro Asp Val Leu
    290                 295                 300

Ser Leu Asn Phe Asn Gln Arg Arg Thr Thr Pro Val Asn Thr Pro Leu
305                 310                 315                 320

Ser Thr Ile His Ala Thr His Thr Phe Val Pro Gln Phe Gly Ala Leu
                325                 330                 335

Asp Gly Val Arg Glu Leu Asn Gly Ala Asp Glu Gln Arg Ala Leu Pro
            340                 345                 350

Ser Thr His Ser Asp Glu Thr Asp Arg Ala Thr Ala Thr Leu

<210> SEQ ID NO 26
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 26

| | | | | | | | | | | | | | | | | |
|---|---|---|---|---|---|---|---|---|---|---|---|---|---|---|---|---|
| atg | gtt | tcg | tat | aac | agc | aag | ttc | ctc | gcg | gca | acc | gtt | cag | gca | gag | 48 |
| Met | Val | Ser | Tyr | Asn | Ser | Lys | Phe | Leu | Ala | Ala | Thr | Val | Gln | Ala | Glu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ccg | gta | tgg | ctc | gac | gca | gac | gca | acg | atc | gac | aag | tcg | atc | ggc | atc | 96 |
| Pro | Val | Trp | Leu | Asp | Ala | Asp | Ala | Thr | Ile | Asp | Lys | Ser | Ile | Gly | Ile | |
| | | 20 | | | | | 25 | | | | | 30 | | | | |

| | | | | | | | | | | | | | | | | |
|---|---|---|---|---|---|---|---|---|---|---|---|---|---|---|---|---|
| atc | gaa | gaa | gct | gcc | caa | aag | ggc | gcg | agt | ctg | atc | gct | ttc | ccg | gaa | 144 |
| Ile | Glu | Glu | Ala | Ala | Gln | Lys | Gly | Ala | Ser | Leu | Ile | Ala | Phe | Pro | Glu | |
| | | | 35 | | | | | 40 | | | | | 45 | | | |

| | | | | | | | | | | | | | | | | |
|---|---|---|---|---|---|---|---|---|---|---|---|---|---|---|---|---|
| gta | ttc | att | ccg | ggc | tac | ccc | tat | tgg | gcg | tgg | ctc | ggc | gac | gtg | aag | 192 |
| Val | Phe | Ile | Pro | Gly | Tyr | Pro | Tyr | Trp | Ala | Trp | Leu | Gly | Asp | Val | Lys | |
| 50 | | | | | 55 | | | | | 60 | | | | | | |

| | | | | | | | | | | | | | | | | |
|---|---|---|---|---|---|---|---|---|---|---|---|---|---|---|---|---|
| tac | agc | cta | agc | ttt | act | tca | cgc | tat | cac | gag | aat | tcg | ttg | gag | cta | 240 |
| Tyr | Ser | Leu | Ser | Phe | Thr | Ser | Arg | Tyr | His | Glu | Asn | Ser | Leu | Glu | Leu | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| ggt | gac | gac | cgt | atg | cgt | cgc | ctc | cag | ctg | gcc | gcg | cgc | cgc | aac | aaa | 288 |
| Gly | Asp | Asp | Arg | Met | Arg | Arg | Leu | Gln | Leu | Ala | Ala | Arg | Arg | Asn | Lys | |
| | | | | 85 | | | | | 90 | | | | | 95 | | |

| | | | | | | | | | | | | | | | | |
|---|---|---|---|---|---|---|---|---|---|---|---|---|---|---|---|---|
| atc | gca | ctc | gtc | atg | ggc | tat | tcg | gag | cgg | gaa | gcc | gga | tcg | cgc | tat | 336 |
| Ile | Ala | Leu | Val | Met | Gly | Tyr | Ser | Glu | Arg | Glu | Ala | Gly | Ser | Arg | Tyr | |
| | | | | 100 | | | | | 105 | | | | | 110 | | |

| | | | | | | | | | | | | | | | | |
|---|---|---|---|---|---|---|---|---|---|---|---|---|---|---|---|---|
| ctg | agc | cag | gtg | ttc | atc | gac | gag | cgt | ggc | gag | atc | gtt | gcc | aat | cgg | 384 |
| Leu | Ser | Gln | Val | Phe | Ile | Asp | Glu | Arg | Gly | Glu | Ile | Val | Ala | Asn | Arg | |
| | | | 115 | | | | | 120 | | | | | 125 | | | |

| | | | | | | | | | | | | | | | | |
|---|---|---|---|---|---|---|---|---|---|---|---|---|---|---|---|---|
| cgc | aag | ctg | aag | ccc | aca | cac | gtt | gag | cgt | acg | atc | tac | ggc | gaa | ggc | 432 |
| Arg | Lys | Leu | Lys | Pro | Thr | His | Val | Glu | Arg | Thr | Ile | Tyr | Gly | Glu | Gly | |
| | | 130 | | | | | 135 | | | | | 140 | | | | |

| | | | | | | | | | | | | | | | | |
|---|---|---|---|---|---|---|---|---|---|---|---|---|---|---|---|---|
| aac | gga | acc | gat | ttc | ctc | acg | cac | gac | ttc | gcg | ttc | gga | cgc | gtc | ggt | 480 |
| Asn | Gly | Thr | Asp | Phe | Leu | Thr | His | Asp | Phe | Ala | Phe | Gly | Arg | Val | Gly | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| gga | ttg | aac | tgc | tgg | gaa | cat | ttc | caa | ccg | ctc | agc | aag | ttc | atg | atg | 528 |
| Gly | Leu | Asn | Cys | Trp | Glu | His | Phe | Gln | Pro | Leu | Ser | Lys | Phe | Met | Met | |
| | | | | 165 | | | | | 170 | | | | | 175 | | |

| | | | | | | | | | | | | | | | | |
|---|---|---|---|---|---|---|---|---|---|---|---|---|---|---|---|---|
| tac | agc | ctc | ggt | gag | cag | gtc | cac | gtt | gca | tcg | tgg | ccg | gcg | atg | tcc | 576 |
| Tyr | Ser | Leu | Gly | Glu | Gln | Val | His | Val | Ala | Ser | Trp | Pro | Ala | Met | Ser | |
| | | | 180 | | | | | 185 | | | | | 190 | | | |

| | | | | | | | | | | | | | | | | |
|---|---|---|---|---|---|---|---|---|---|---|---|---|---|---|---|---|
| cct | ctt | cag | ccg | gat | gtt | ttc | caa | cag | agc | atc | gaa | gcc | aac | gcg | acg | 624 |
| Pro | Leu | Gln | Pro | Asp | Val | Phe | Gln | Gln | Ser | Ile | Glu | Ala | Asn | Ala | Thr | |
| | | 195 | | | | | 200 | | | | | 205 | | | | |

| | | | | | | | | | | | | | | | | |
|---|---|---|---|---|---|---|---|---|---|---|---|---|---|---|---|---|
| gtc | acc | cgc | tcg | tac | gca | atc | gaa | ggc | caa | acc | ttt | gtg | ctt | tgc | tcg | 672 |
| Val | Thr | Arg | Ser | Tyr | Ala | Ile | Glu | Gly | Gln | Thr | Phe | Val | Leu | Cys | Ser | |
| | 210 | | | | | 215 | | | | | 220 | | | | | |

| | | | | | | | | | | | | | | | | |
|---|---|---|---|---|---|---|---|---|---|---|---|---|---|---|---|---|
| acg | cag | gtg | atc | gga | cct | agc | gcg | atc | gaa | acg | ttc | tgc | ctc | aac | gac | 720 |
| Thr | Gln | Val | Ile | Gly | Pro | Ser | Ala | Ile | Glu | Thr | Phe | Cys | Leu | Asn | Asp | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| gaa | cag | cgc | gca | ctg | ttg | ccg | caa | gga | tgt | ggc | tgg | gcg | cgc | att | tac | 768 |
| Glu | Gln | Arg | Ala | Leu | Leu | Pro | Gln | Gly | Cys | Gly | Trp | Ala | Arg | Ile | Tyr | |
| | | | | 245 | | | | | 250 | | | | | 255 | | |

| | | | | | | | | | | | | | | | | |
|---|---|---|---|---|---|---|---|---|---|---|---|---|---|---|---|---|
| ggc | ccg | gat | gga | agc | gag | ctt | gcg | aag | cct | ctg | gcg | gaa | gat | gct | gag | 816 |
| Gly | Pro | Asp | Gly | Ser | Glu | Leu | Ala | Lys | Pro | Leu | Ala | Glu | Asp | Ala | Glu | |

```
                    260                 265                 270
ggg atc ttg tac gca gag atc gat ctg gag cag att ctg ctg gcg aag    864
Gly Ile Leu Tyr Ala Glu Ile Asp Leu Glu Gln Ile Leu Leu Ala Lys
        275                 280                 285 gct gga gcc gat ccg gtc ggg cac tat tcg cgg cct gac gtg ctg tcg    912
Ala Gly Ala Asp Pro Val Gly His Tyr Ser Arg Pro Asp Val Leu Ser
    290                 295                 300 gtc cag ttc gac ccg cgc aat cat acg cca gtt cat cgc atc ggc att    960
Val Gln Phe Asp Pro Arg Asn His Thr Pro Val His Arg Ile Gly Ile
305                 310                 315                 320 gac ggt cgc ttg gat gtg aat acc cgc agt cgc gtg gag aat ttc cga   1008
Asp Gly Arg Leu Asp Val Asn Thr Arg Ser Arg Val Glu Asn Phe Arg
                325                 330                 335 ctg cga caa gcg gct gag cag gag cgt cag gca tcc aag cgg ctc gga   1056
Leu Arg Gln Ala Ala Glu Gln Glu Arg Gln Ala Ser Lys Arg Leu Gly
            340                 345                 350 acg aaa ctc ttt gaa caa tcc ctt ctg gct gaa gaa ccg gtc cca gca   1104
Thr Lys Leu Phe Glu Gln Ser Leu Leu Ala Glu Glu Pro Val Pro Ala
        355                 360                 365 aag tag                                                            1110
Lys

<210> SEQ ID NO 27
<211> LENGTH: 369
<212> TYPE: PRT
<213> ORGANISM: Acidovorax facilis 72W

<400> SEQUENCE: 27

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Gln Ser Ile Glu Ala Asn Ala Thr
        195                 200                 205

Val Thr Arg Ser Tyr Ala Ile Glu Gly Gln Thr Phe Val Leu Cys Ser
    210                 215                 220
```

```
Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
            245                 250                 255

Gly Pro Asp Gly Ser Glu Leu Ala Lys Pro Leu Ala Glu Asp Ala Glu
        260                 265                 270

Gly Ile Leu Tyr Ala Glu Ile Asp Leu Glu Gln Ile Leu Leu Ala Lys
    275                 280                 285

Ala Gly Ala Asp Pro Val Gly His Tyr Ser Arg Pro Asp Val Leu Ser
290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Glu Pro Val Pro Ala
        355                 360                 365

Lys

<210> SEQ ID NO 28
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 28 atg gtt tcg tat aac agc aag ttc ctc gcg gca acc gtt cag gca gag      48
Met Val Ser Tyr Asn Ser Lys Phe Leu Ala Ala Thr Val Gln Ala Glu
1               5                   10                  15 ccg gta tgg ctc gac gca gac gca acg atc gac aag tcg atc ggc atc      96
Pro Val Trp Leu Asp Ala Asp Ala Thr Ile Asp Lys Ser Ile Gly Ile
            20                  25                  30 atc gaa gaa gct gcc caa aag ggc gcg agt ctg atc gct ttc ccg gaa     144
Ile Glu Glu Ala Ala Gln Lys Gly Ala Ser Leu Ile Ala Phe Pro Glu
        35                  40                  45 gta ttc att ccg ggc tac ccc tat tgg gcg tgg ctc ggc gac gtg aag     192
Val Phe Ile Pro Gly Tyr Pro Tyr Trp Ala Trp Leu Gly Asp Val Lys
    50                  55                  60 tac agc cta agc ttt act tca cgc tat cac gag aat tcg ttg gag cta     240
Tyr Ser Leu Ser Phe Thr Ser Arg Tyr His Glu Asn Ser Leu Glu Leu
65                  70                  75                  80 ggt gac gac cgt atg cgt cgc ctc cag ctg gcc gcg cgc cgc aac aaa     288
Gly Asp Asp Arg Met Arg Arg Leu Gln Leu Ala Ala Arg Arg Asn Lys
                85                  90                  95 atc gca ctc gtc atg ggc tat tcg gag cgg gaa gcc gga tcg cgc tat     336
Ile Ala Leu Val Met Gly Tyr Ser Glu Arg Glu Ala Gly Ser Arg Tyr
            100                 105                 110 ctg agc cag gtg ttc atc gac gag cgt ggc gag atc gtt gcc aat cgg     384
Leu Ser Gln Val Phe Ile Asp Glu Arg Gly Glu Ile Val Ala Asn Arg
        115                 120                 125 cgc aag ctg aag ccc aca cac gtt gag cgt acg atc tac ggc gaa ggc     432
Arg Lys Leu Lys Pro Thr His Val Glu Arg Thr Ile Tyr Gly Glu Gly
    130                 135                 140 aac gga acc gat ttc ctc acg cac gac ttc gcg ttc gga cgc gtc ggt     480
Asn Gly Thr Asp Phe Leu Thr His Asp Phe Ala Phe Gly Arg Val Gly
145                 150                 155                 160
```

```
gga ttg aac tgc tgg gaa cat ttc caa ccg ctc agc aag ttc atg atg        528
Gly Leu Asn Cys Trp Glu His Phe Gln Pro Leu Ser Lys Phe Met Met
            165                 170                 175 tac agc ctc ggt gag cag gtc cac gtt gca tcg tgg ccg gcg atg tcc        576
Tyr Ser Leu Gly Glu Gln Val His Val Ala Ser Trp Pro Ala Met Ser
        180                 185                 190 cct ctt cag ccg gat gtt ttc caa gct agc atc gaa gcc aac gcg acg        624
Pro Leu Gln Pro Asp Val Phe Gln Ala Ser Ile Glu Ala Asn Ala Thr
    195                 200                 205 gtc acc cgc tcg tac gca atc gaa ggc caa acc ttt gtg ctt tgc tcg        672
Val Thr Arg Ser Tyr Ala Ile Glu Gly Gln Thr Phe Val Leu Cys Ser
210                 215                 220 acg cag gtg atc gga cct agc gcg atc gaa acg ttc tgc ctc aac gac        720
Thr Gln Val Ile Gly Pro Ser Ala Ile Glu Thr Phe Cys Leu Asn Asp
225                 230                 235                 240 gaa cag cgc gca ctg ttg ccg caa gga tgt ggc tgg gcg cgc att tac        768
Glu Gln Arg Ala Leu Leu Pro Gln Gly Cys Gly Trp Ala Arg Ile Tyr
                245                 250                 255 ggc ccg gat gga agc gag ctt gcg aag cct ctg gcg gaa gat gct gag        816
Gly Pro Asp Gly Ser Glu Leu Ala Lys Pro Leu Ala Glu Asp Ala Glu
            260                 265                 270 ggg atc ttg tac gca gag atc gat ctg gag cag att ctg ctg gcg aag        864
Gly Ile Leu Tyr Ala Glu Ile Asp Leu Glu Gln Ile Leu Leu Ala Lys
        275                 280                 285 gct gga gcc gat ccg gtc ggg cac tat tcg cgg cct gac gtg ctg tcg        912
Ala Gly Ala Asp Pro Val Gly His Tyr Ser Arg Pro Asp Val Leu Ser
    290                 295                 300 gtc cag ttc gac ccg cgc aat cat acg cca gtt cat cgc atc ggc att        960
Val Gln Phe Asp Pro Arg Asn His Thr Pro Val His Arg Ile Gly Ile
305                 310                 315                 320 gac ggt cgc ttg gat gtg aat acc cgc agt cgc gtg gag aat ttc cga       1008
Asp Gly Arg Leu Asp Val Asn Thr Arg Ser Arg Val Glu Asn Phe Arg
                325                 330                 335 ctg cga caa gcg gct gag cag gag cgt cag gca tcc aag cgg ctc gga       1056
Leu Arg Gln Ala Ala Glu Gln Glu Arg Gln Ala Ser Lys Arg Leu Gly
            340                 345                 350 acg aaa ctc ttt gaa caa tcc ctt ctg gct gaa gaa ccg gtc cca gca       1104
Thr Lys Leu Phe Glu Gln Ser Leu Leu Ala Glu Glu Pro Val Pro Ala
        355                 360                 365 aag tag                                                               1110
Lys

<210> SEQ ID NO 29
<211> LENGTH: 369
<212> TYPE: PRT
<213> ORGANISM: Acidovorax facilis 72W

<400> SEQUENCE: 29

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80
```

```
Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Ala Ser Ile Glu Ala Asn Ala Thr
        195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
    290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Glu Pro Val Pro Ala
        355                 360                 365

Lys

<210> SEQ ID NO 30
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 30 atg gtt tcg tat aac agc aag ttc ctc gcg gca acc gtt cag gca gag     48
Met Val Ser Tyr Asn Ser Lys Phe Leu Ala Ala Thr Val Gln Ala Glu
1               5                   10                  15 ccg gta tgg ctc gac gca gac gca acg atc gac aag tcg atc ggc atc     96
Pro Val Trp Leu Asp Ala Asp Ala Thr Ile Asp Lys Ser Ile Gly Ile
            20                  25                  30 atc gaa gaa gct gcc caa aag ggc gcg agt ctg atc gct ttc ccg gaa    144
Ile Glu Glu Ala Ala Gln Lys Gly Ala Ser Leu Ile Ala Phe Pro Glu
        35                  40                  45
```

```
gta ttc att ccg ggc tac ccc tat tgg gcg tgg ctc ggc gac gtg aag        192
Val Phe Ile Pro Gly Tyr Pro Tyr Trp Ala Trp Leu Gly Asp Val Lys
 50                  55                  60 tac agc cta agc ttt act tca cgc tat cac gag aat tcg ttg gag cta        240
Tyr Ser Leu Ser Phe Thr Ser Arg Tyr His Glu Asn Ser Leu Glu Leu
 65                  70                  75                  80 ggt gac gac cgt atg cgt cgc ctc cag ctg gcc gcg cgc cgc aac aaa        288
Gly Asp Asp Arg Met Arg Arg Leu Gln Leu Ala Ala Arg Arg Asn Lys
                     85                  90                  95 atc gca ctc gtc atg ggc tat tcg gag cgg gaa gcc gga tcg cgc tat        336
Ile Ala Leu Val Met Gly Tyr Ser Glu Arg Glu Ala Gly Ser Arg Tyr
                100                 105                 110 ctg agc cag gtg ttc atc gac gag cgt ggc gag atc gtt gcc aat cgg        384
Leu Ser Gln Val Phe Ile Asp Glu Arg Gly Glu Ile Val Ala Asn Arg
            115                 120                 125 cgc aag ctg aag ccc aca cac gtt gag cgt acg atc tac ggc gaa ggc        432
Arg Lys Leu Lys Pro Thr His Val Glu Arg Thr Ile Tyr Gly Glu Gly
130                 135                 140 aac gga acc gat ttc ctc acg cac gac ttc gcg ttc gga cgc gtc ggt        480
Asn Gly Thr Asp Phe Leu Thr His Asp Phe Ala Phe Gly Arg Val Gly
145                 150                 155                 160 gga ttg aac tgc tgg gaa cat ttc caa ccg ctc agc aag ttc atg atg        528
Gly Leu Asn Cys Trp Glu His Phe Gln Pro Leu Ser Lys Phe Met Met
                165                 170                 175 tac agc ctc ggt gag cag gtc cac gtt gca tcg tgg ccg gcg atg tcc        576
Tyr Ser Leu Gly Glu Gln Val His Val Ala Ser Trp Pro Ala Met Ser
                180                 185                 190 cct ctt cag ccg gat gtt ttc caa tgt agc atc gaa gcc aac gcg acg        624
Pro Leu Gln Pro Asp Val Phe Gln Cys Ser Ile Glu Ala Asn Ala Thr
            195                 200                 205 gtc acc cgc tcg tac gca atc gaa ggc caa acc ttt gtg ctt tgc tcg        672
Val Thr Arg Ser Tyr Ala Ile Glu Gly Gln Thr Phe Val Leu Cys Ser
210                 215                 220 acg cag gtg atc gga cct agc gcg atc gaa acg ttc tgc ctc aac gac        720
Thr Gln Val Ile Gly Pro Ser Ala Ile Glu Thr Phe Cys Leu Asn Asp
225                 230                 235                 240 gaa cag cgc gca ctg ttg ccg caa gga tgt ggc tgg gcg cgc att tac        768
Glu Gln Arg Ala Leu Leu Pro Gln Gly Cys Gly Trp Ala Arg Ile Tyr
                245                 250                 255 ggc ccg gat gga agc gag ctt gcg aag cct ctg gcg gaa gat gct gag        816
Gly Pro Asp Gly Ser Glu Leu Ala Lys Pro Leu Ala Glu Asp Ala Glu
                260                 265                 270 ggg atc ttg tac gca gag atc gat ctg gag cag att ctg ctg gcg aag        864
Gly Ile Leu Tyr Ala Glu Ile Asp Leu Glu Gln Ile Leu Leu Ala Lys
            275                 280                 285 gct gga gcc gat ccg gtc ggg cac tat tcg cgg cct gac gtg ctg tcg        912
Ala Gly Ala Asp Pro Val Gly His Tyr Ser Arg Pro Asp Val Leu Ser
290                 295                 300 gtc cag ttc gac ccg cgc aat cat acg cca gtt cat cgc atc ggc att        960
Val Gln Phe Asp Pro Arg Asn His Thr Pro Val His Arg Ile Gly Ile
305                 310                 315                 320 gac ggt cgc ttg gat gtg aat acc cgc agt cgc gtg gag aat ttc cga       1008
Asp Gly Arg Leu Asp Val Asn Thr Arg Ser Arg Val Glu Asn Phe Arg
                325                 330                 335 ctg cga caa gcg gct gag cag gag cgt cag gca tcc aag cgg ctc gga       1056
Leu Arg Gln Ala Ala Glu Gln Glu Arg Gln Ala Ser Lys Arg Leu Gly
                340                 345                 350 acg aaa ctc ttt gaa caa tcc ctt ctg gct gaa gaa ccg gtc cca gca       1104
Thr Lys Leu Phe Glu Gln Ser Leu Leu Ala Glu Glu Pro Val Pro Ala
            355                 360                 365
```

```
aag tag                                                              1110
Lys <210> SEQ ID NO 31
<211> LENGTH: 369
<212> TYPE: PRT
<213> ORGANISM: Acidovorax facilis 72W

<400> SEQUENCE: 31

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Cys Ser Ile Glu Ala Asn Ala Thr
        195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
    290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Glu Pro Val Pro Ala
        355                 360                 365
```

Lys

<210> SEQ ID NO 32
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 32

| | | | | | | | | | | | | | | | | |
|---|---|---|---|---|---|---|---|---|---|---|---|---|---|---|---|---|
| atg | gtt | tcg | tat | aac | agc | aag | ttc | ctc | gcg | gca | acc | gtt | cag | gca | gag | 48 |
| Met | Val | Ser | Tyr | Asn | Ser | Lys | Phe | Leu | Ala | Ala | Thr | Val | Gln | Ala | Glu | |
| 1 | | | | 5 | | | | | 10 | | | | | 15 | | |
| ccg | gta | tgg | ctc | gac | gca | gac | gca | acg | atc | gac | aag | tcg | atc | ggc | atc | 96 |
| Pro | Val | Trp | Leu | Asp | Ala | Asp | Ala | Thr | Ile | Asp | Lys | Ser | Ile | Gly | Ile | |
| | | 20 | | | | | 25 | | | | | 30 | | | | |
| atc | gaa | gaa | gct | gcc | caa | aag | ggc | gcg | agt | ctg | atc | gct | ttc | ccg | gaa | 144 |
| Ile | Glu | Glu | Ala | Ala | Gln | Lys | Gly | Ala | Ser | Leu | Ile | Ala | Phe | Pro | Glu | |
| | 35 | | | | | 40 | | | | | 45 | | | | | |
| gta | ttc | att | ccg | ggc | tac | ccc | tat | tgg | gcg | tgg | ctc | ggc | gac | gtg | aag | 192 |
| Val | Phe | Ile | Pro | Gly | Tyr | Pro | Tyr | Trp | Ala | Trp | Leu | Gly | Asp | Val | Lys | |
| | 50 | | | | | 55 | | | | | 60 | | | | | |
| tac | agc | cta | agc | ttt | act | tca | cgc | tat | cac | gag | aat | tcg | ttg | gag | cta | 240 |
| Tyr | Ser | Leu | Ser | Phe | Thr | Ser | Arg | Tyr | His | Glu | Asn | Ser | Leu | Glu | Leu | |
| 65 | | | | | 70 | | | | | 75 | | | | | 80 | |
| ggt | gac | gac | cgt | atg | cgt | cgc | ctc | cag | ctg | gcc | gcg | cgc | cgc | aac | aaa | 288 |
| Gly | Asp | Asp | Arg | Met | Arg | Arg | Leu | Gln | Leu | Ala | Ala | Arg | Arg | Asn | Lys | |
| | | | | 85 | | | | | 90 | | | | | 95 | | |
| atc | gca | ctc | gtc | atg | ggc | tat | tcg | gag | cgg | gaa | gcc | gga | tcg | cgc | tat | 336 |
| Ile | Ala | Leu | Val | Met | Gly | Tyr | Ser | Glu | Arg | Glu | Ala | Gly | Ser | Arg | Tyr | |
| | | | 100 | | | | | 105 | | | | | 110 | | | |
| ctg | agc | cag | gtg | ttc | atc | gac | gag | cgt | ggc | gag | atc | gtt | gcc | aat | cgg | 384 |
| Leu | Ser | Gln | Val | Phe | Ile | Asp | Glu | Arg | Gly | Glu | Ile | Val | Ala | Asn | Arg | |
| | | 115 | | | | | 120 | | | | | 125 | | | | |
| cgc | aag | ctg | aag | ccc | aca | cac | gtt | gag | cgt | acg | atc | tac | ggc | gaa | ggc | 432 |
| Arg | Lys | Leu | Lys | Pro | Thr | His | Val | Glu | Arg | Thr | Ile | Tyr | Gly | Glu | Gly | |
| | 130 | | | | | 135 | | | | | 140 | | | | | |
| aac | gga | acc | gat | ttc | ctc | acg | cac | gac | ttc | gcg | ttc | gga | cgc | gtc | ggt | 480 |
| Asn | Gly | Thr | Asp | Phe | Leu | Thr | His | Asp | Phe | Ala | Phe | Gly | Arg | Val | Gly | |
| 145 | | | | | 150 | | | | | 155 | | | | | 160 | |
| gga | ttg | aac | tgc | tgg | gaa | cat | ttc | caa | ccg | ctc | agc | aag | ttc | atg | atg | 528 |
| Gly | Leu | Asn | Cys | Trp | Glu | His | Phe | Gln | Pro | Leu | Ser | Lys | Phe | Met | Met | |
| | | | | 165 | | | | | 170 | | | | | 175 | | |
| tac | agc | ctc | ggt | gag | cag | gtc | cac | gtt | gca | tcg | tgg | ccg | gcg | atg | tcc | 576 |
| Tyr | Ser | Leu | Gly | Glu | Gln | Val | His | Val | Ala | Ser | Trp | Pro | Ala | Met | Ser | |
| | | | 180 | | | | | 185 | | | | | 190 | | | |
| cct | ctt | cag | ccg | gat | gtt | ttc | caa | acc | agc | atc | gaa | gcc | aac | gcg | acg | 624 |
| Pro | Leu | Gln | Pro | Asp | Val | Phe | Gln | Thr | Ser | Ile | Glu | Ala | Asn | Ala | Thr | |
| | | 195 | | | | | 200 | | | | | 205 | | | | |
| gtc | acc | cgc | tcg | tac | gca | atc | gaa | ggc | caa | acc | ttt | gtg | ctt | tgc | tcg | 672 |
| Val | Thr | Arg | Ser | Tyr | Ala | Ile | Glu | Gly | Gln | Thr | Phe | Val | Leu | Cys | Ser | |
| | 210 | | | | | 215 | | | | | 220 | | | | | |
| acg | cag | gtg | atc | gga | cct | agc | gcg | atc | gaa | acg | ttc | tgc | ctc | aac | gac | 720 |
| Thr | Gln | Val | Ile | Gly | Pro | Ser | Ala | Ile | Glu | Thr | Phe | Cys | Leu | Asn | Asp | |
| 225 | | | | | 230 | | | | | 235 | | | | | 240 | |
| gaa | cag | cgc | gca | ctg | ttg | ccg | caa | gga | tgt | ggc | tgg | gcg | cgc | att | tac | 768 |
| Glu | Gln | Arg | Ala | Leu | Leu | Pro | Gln | Gly | Cys | Gly | Trp | Ala | Arg | Ile | Tyr | |
| | | | | 245 | | | | | 250 | | | | | 255 | | |

```
ggc ccg gat gga agc gag ctt gcg aag cct ctg gcg gaa gat gct gag      816
Gly Pro Asp Gly Ser Glu Leu Ala Lys Pro Leu Ala Glu Asp Ala Glu
        260                 265                 270 ggg atc ttg tac gca gag atc gat ctg gag cag att ctg ctg gcg aag      864
Gly Ile Leu Tyr Ala Glu Ile Asp Leu Glu Gln Ile Leu Leu Ala Lys
        275                 280                 285 gct gga gcc gat ccg gtc ggg cac tat tcg cgg cct gac gtg ctg tcg      912
Ala Gly Ala Asp Pro Val Gly His Tyr Ser Arg Pro Asp Val Leu Ser
290                 295                 300 gtc cag ttc gac ccg cgc aat cat acg cca gtt cat cgc atc ggc att      960
Val Gln Phe Asp Pro Arg Asn His Thr Pro Val His Arg Ile Gly Ile
305                 310                 315                 320 gac ggt cgc ttg gat gtg aat acc cgc agt cgc gtg gag aat ttc cga     1008
Asp Gly Arg Leu Asp Val Asn Thr Arg Ser Arg Val Glu Asn Phe Arg
                325                 330                 335 ctg cga caa gcg gct gag cag gag cgt cag gca tcc aag cgg ctc gga     1056
Leu Arg Gln Ala Ala Glu Gln Glu Arg Gln Ala Ser Lys Arg Leu Gly
            340                 345                 350 acg aaa ctc ttt gaa caa tcc ctt ctg gct gaa gaa ccg gtc cca gca     1104
Thr Lys Leu Phe Glu Gln Ser Leu Leu Ala Glu Glu Pro Val Pro Ala
        355                 360                 365 aag tag                                                             1110
Lys

<210> SEQ ID NO 33
<211> LENGTH: 369
<212> TYPE: PRT
<213> ORGANISM: Acidovorax facilis 72W

<400> SEQUENCE: 33

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Thr Ser Ile Glu Ala Asn Ala Thr
        195                 200                 205

Val Thr Arg Ser Tyr Ala Ile Glu Gly Gln Thr Phe Val Leu Cys Ser
```

```
              210                 215                 220
Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
            275                 280                 285

Ala Gly Ala Asp Pro Val Gly His Tyr Ser Arg Pro Asp Val Leu Ser
        290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
                340                 345                 350

Thr Lys Leu Phe Glu Gln Ser Leu Leu Ala Glu Glu Pro Val Pro Ala
            355                 360                 365

Lys

<210> SEQ ID NO 34
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 34 atg gtt tcg tat aac agc aag ttc ctc gcg gca acc gtt cag gca gag      48
Met Val Ser Tyr Asn Ser Lys Phe Leu Ala Ala Thr Val Gln Ala Glu
1               5                   10                  15 ccg gta tgg ctc gac gca gac gca acg atc gac aag tcg atc ggc atc      96
Pro Val Trp Leu Asp Ala Asp Ala Thr Ile Asp Lys Ser Ile Gly Ile
            20                  25                  30 atc gaa gaa gct gcc caa aag ggc gcg agt ctg atc gct ttc ccg gaa     144
Ile Glu Glu Ala Ala Gln Lys Gly Ala Ser Leu Ile Ala Phe Pro Glu
        35                  40                  45 gta ttc att ccg ggc tac ccc tat tgg gcg tgg ctc ggc gac gtg aag     192
Val Phe Ile Pro Gly Tyr Pro Tyr Trp Ala Trp Leu Gly Asp Val Lys
    50                  55                  60 tac agc cta agc ttt act tca cgc tat cac gag aat tcg ttg gag cta     240
Tyr Ser Leu Ser Phe Thr Ser Arg Tyr His Glu Asn Ser Leu Glu Leu
65                  70                  75                  80 ggt gac gac cgt atg cgt cgc ctc cag ctg gcc gcg cgc cgc aac aaa     288
Gly Asp Asp Arg Met Arg Arg Leu Gln Leu Ala Ala Arg Arg Asn Lys
                85                  90                  95 atc gca ctc gtc atg ggc tat tcg gag cgg gaa gcc gga tcg cgc tat     336
Ile Ala Leu Val Met Gly Tyr Ser Glu Arg Glu Ala Gly Ser Arg Tyr
            100                 105                 110 ctg agc cag gtg ttc atc gac gag cgt ggc gag atc gtt gcc aat cgg     384
Leu Ser Gln Val Phe Ile Asp Glu Arg Gly Glu Ile Val Ala Asn Arg
        115                 120                 125 cgc aag ctg aag ccc aca cac gtt gag cgt acg atc tac ggc gaa ggc     432
Arg Lys Leu Lys Pro Thr His Val Glu Arg Thr Ile Tyr Gly Glu Gly
    130                 135                 140 aac gga acc gat ttc ctc acg cac gac ttc gcg ttc gga cgc gtc ggt     480
```

```
Asn Gly Thr Asp Phe Leu Thr His Asp Phe Ala Phe Gly Arg Val Gly
145                 150                 155                 160 gga ttg aac tgc tgg gaa cat ttc caa ccg ctc agc aag ttc atg atg    528
Gly Leu Asn Cys Trp Glu His Phe Gln Pro Leu Ser Lys Phe Met Met
            165                 170                 175 tac agc ctc ggt gag cag gtc cac gtt gca tcg tgg ccg gcg atg tcc    576
Tyr Ser Leu Gly Glu Gln Val His Val Ala Ser Trp Pro Ala Met Ser
        180                 185                 190 cct ctt cag ccg gat gtt ttc caa gga agc atc gaa gcc aac gcg acg    624
Pro Leu Gln Pro Asp Val Phe Gln Gly Ser Ile Glu Ala Asn Ala Thr
    195                 200                 205 gtc acc cgc tcg tac gca atc gaa ggc caa acc ttt gtg ctt tgc tcg    672
Val Thr Arg Ser Tyr Ala Ile Glu Gly Gln Thr Phe Val Leu Cys Ser
210                 215                 220 acg cag gtg atc gga cct agc gcg atc gaa acg ttc tgc ctc aac gac    720
Thr Gln Val Ile Gly Pro Ser Ala Ile Glu Thr Phe Cys Leu Asn Asp
225                 230                 235                 240 gaa cag cgc gca ctg ttg ccg caa gga tgt ggc tgg gcg cgc att tac    768
Glu Gln Arg Ala Leu Leu Pro Gln Gly Cys Gly Trp Ala Arg Ile Tyr
            245                 250                 255 ggc ccg gat gga agc gag ctt gcg aag cct ctg gcg gaa gat gct gag    816
Gly Pro Asp Gly Ser Glu Leu Ala Lys Pro Leu Ala Glu Asp Ala Glu
        260                 265                 270 ggg atc ttg tac gca gag atc gat ctg gag cag att ctg ctg gcg aag    864
Gly Ile Leu Tyr Ala Glu Ile Asp Leu Glu Gln Ile Leu Leu Ala Lys
    275                 280                 285 gct gga gcc gat ccg gtc ggg cac tat tcg cgg cct gac gtg ctg tcg    912
Ala Gly Ala Asp Pro Val Gly His Tyr Ser Arg Pro Asp Val Leu Ser
290                 295                 300 gtc cag ttc gac ccg cgc aat cat acg cca gtt cat cgc atc ggc att    960
Val Gln Phe Asp Pro Arg Asn His Thr Pro Val His Arg Ile Gly Ile
305                 310                 315                 320 gac ggt cgc ttg gat gtg aat acc cgc agt cgc gtg gag aat ttc cga   1008
Asp Gly Arg Leu Asp Val Asn Thr Arg Ser Arg Val Glu Asn Phe Arg
            325                 330                 335 ctg cga caa gcg gct gag cag gag cgt cag gca tcc aag cgg ctc gga   1056
Leu Arg Gln Ala Ala Glu Gln Glu Arg Gln Ala Ser Lys Arg Leu Gly
        340                 345                 350 acg aaa ctc ttt gaa caa tcc ctt ctg gct gaa gaa ccg gtc cca gca   1104
Thr Lys Leu Phe Glu Gln Ser Leu Leu Ala Glu Glu Pro Val Pro Ala
    355                 360                 365 aag tag                                                            1110
Lys

<210> SEQ ID NO 35
<211> LENGTH: 369
<212> TYPE: PRT
<213> ORGANISM: Acidovorax facilis 72W

<400> SEQUENCE: 35

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
```

```
                65                  70                  75                  80
Gly Asp Asp Arg Met Arg Arg Leu Gln Leu Ala Ala Arg Arg Asn Lys
                    85                  90                  95

Ile Ala Leu Val Met Gly Tyr Ser Glu Arg Glu Ala Gly Ser Arg Tyr
                100                 105                 110

Leu Ser Gln Val Phe Ile Asp Glu Arg Gly Glu Ile Val Ala Asn Arg
            115                 120                 125

Arg Lys Leu Lys Pro Thr His Val Glu Arg Thr Ile Tyr Gly Glu Gly
        130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                165                 170                 175

Tyr Ser Leu Gly Glu Gln Val His Val Ala Ser Trp Pro Ala Met Ser
                180                 185                 190

Pro Leu Gln Pro Asp Val Phe Gln Gly Ser Ile Glu Ala Asn Ala Thr
            195                 200                 205

Val Thr Arg Ser Tyr Ala Ile Glu Gly Gln Thr Phe Val Leu Cys Ser
        210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
                260                 265                 270

Gly Ile Leu Tyr Ala Glu Ile Asp Leu Glu Gln Ile Leu Leu Ala Lys
            275                 280                 285

Ala Gly Ala Asp Pro Val Gly His Tyr Ser Arg Pro Asp Val Leu Ser
        290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
                340                 345                 350

Thr Lys Leu Phe Glu Gln Ser Leu Leu Ala Glu Glu Pro Val Pro Ala
            355                 360                 365
Lys

<210> SEQ ID NO 36
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 36 atg gtt tcg tat aac agc aag ttc ctc gcg gca acc gtt cag gca gag      48
Met Val Ser Tyr Asn Ser Lys Phe Leu Ala Ala Thr Val Gln Ala Glu
1               5                   10                  15 ccg gta tgg ctc gac gca gac gca acg atc gac aag tcg atc ggc atc      96
Pro Val Trp Leu Asp Ala Asp Ala Thr Ile Asp Lys Ser Ile Gly Ile
            20                  25                  30 atc gaa gaa gct gcc caa aag ggc gcg agt ctg atc gct ttc ccg gaa     144
Ile Glu Glu Ala Ala Gln Lys Gly Ala Ser Leu Ile Ala Phe Pro Glu
```

-continued

```
            35                  40                  45
gta ttc att ccg ggc tac ccc tat tgg gcg tgg ctc ggc gac gtg aag      192
Val Phe Ile Pro Gly Tyr Pro Tyr Trp Ala Trp Leu Gly Asp Val Lys
 50                  55                  60 tac agc cta agc ttt act tca cgc tat cac gag aat tcg ttg gag cta      240
Tyr Ser Leu Ser Phe Thr Ser Arg Tyr His Glu Asn Ser Leu Glu Leu
 65                  70                  75                  80 ggt gac gac cgt atg cgt cgc ctc cag ctg gcc gcg cgc cgc aac aaa      288
Gly Asp Asp Arg Met Arg Arg Leu Gln Leu Ala Ala Arg Arg Asn Lys
                 85                  90                  95 atc gca ctc gtc atg ggc tat tcg gag cgg gaa gcc gga tcg cgc tat      336
Ile Ala Leu Val Met Gly Tyr Ser Glu Arg Glu Ala Gly Ser Arg Tyr
            100                 105                 110 ctg agc cag gtg ttc atc gac gag cgt ggc gag atc gtt gcc aat cgg      384
Leu Ser Gln Val Phe Ile Asp Glu Arg Gly Glu Ile Val Ala Asn Arg
        115                 120                 125 cgc aag ctg aag ccc aca cac gtt gag cgt acg atc tac ggc gaa ggc      432
Arg Lys Leu Lys Pro Thr His Val Glu Arg Thr Ile Tyr Gly Glu Gly
    130                 135                 140 aac gga acc gat ttc ctc acg cac gac ttc gcg ttc gga cgc gtc ggt      480
Asn Gly Thr Asp Phe Leu Thr His Asp Phe Ala Phe Gly Arg Val Gly
145                 150                 155                 160 gga ttg aac tgc tgg gaa cat ttc caa ccg ctc agc aag ttc atg atg      528
Gly Leu Asn Cys Trp Glu His Phe Gln Pro Leu Ser Lys Phe Met Met
                165                 170                 175 tac agc ctc ggt gag cag gtc cac gtt gca tcg tgg ccg gcg atg tcc      576
Tyr Ser Leu Gly Glu Gln Val His Val Ala Ser Trp Pro Ala Met Ser
            180                 185                 190 cct ctt cag ccg gat gtt ttc caa cac agc atc gaa gcc aac gcg acg      624
Pro Leu Gln Pro Asp Val Phe Gln His Ser Ile Glu Ala Asn Ala Thr
        195                 200                 205 gtc acc cgc tcg tac gca atc gaa ggc caa acc ttt gtg ctt tgc tcg      672
Val Thr Arg Ser Tyr Ala Ile Glu Gly Gln Thr Phe Val Leu Cys Ser
    210                 215                 220 acg cag gtg atc gga cct agc gcg atc gaa acg ttc tgc ctc aac gac      720
Thr Gln Val Ile Gly Pro Ser Ala Ile Glu Thr Phe Cys Leu Asn Asp
225                 230                 235                 240 gaa cag cgc gca ctg ttg ccg caa gga tgt ggc tgg gcg cgc att tac      768
Glu Gln Arg Ala Leu Leu Pro Gln Gly Cys Gly Trp Ala Arg Ile Tyr
                245                 250                 255 ggc ccg gat gga agc gag ctt gcg aag cct ctg gcg gaa gat gct gag      816
Gly Pro Asp Gly Ser Glu Leu Ala Lys Pro Leu Ala Glu Asp Ala Glu
            260                 265                 270 ggg atc ttg tac gca gag atc gat ctg gag cag att ctg ctg gcg aag      864
Gly Ile Leu Tyr Ala Glu Ile Asp Leu Glu Gln Ile Leu Leu Ala Lys
        275                 280                 285 gct gga gcc gat ccg gtc ggg cac tat tcg cgg cct gac gtg ctg tcg      912
Ala Gly Ala Asp Pro Val Gly His Tyr Ser Arg Pro Asp Val Leu Ser
    290                 295                 300 gtc cag ttc gac ccg cgc aat cat acg cca gtt cat cgc atc ggc att      960
Val Gln Phe Asp Pro Arg Asn His Thr Pro Val His Arg Ile Gly Ile
305                 310                 315                 320 gac ggt cgc ttg gat gtg aat acc cgc agt cgc gtg gag aat ttc cga     1008
Asp Gly Arg Leu Asp Val Asn Thr Arg Ser Arg Val Glu Asn Phe Arg
                325                 330                 335 ctg cga caa gcg gct gag cag gag cgt cag gca tcc aag cgg ctc gga     1056
Leu Arg Gln Ala Ala Glu Gln Glu Arg Gln Ala Ser Lys Arg Leu Gly
            340                 345                 350 acg aaa ctc ttt gaa caa tcc ctt ctg gct gaa gaa ccg gtc cca gca     1104
```

```
Thr Lys Leu Phe Glu Gln Ser Leu Leu Ala Glu Glu Pro Val Pro Ala
            355                 360                 365 aag tag                                                                 1110
Lys
```

<210> SEQ ID NO 37
<211> LENGTH: 369
<212> TYPE: PRT
<213> ORGANISM: Acidovorax facilis 72W

<400> SEQUENCE: 37

```
Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln His Ser Ile Glu Ala Asn Ala Thr
        195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
    290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350
```

```
Thr Lys Leu Phe Glu Gln Ser Leu Leu Ala Glu Glu Pro Val Pro Ala
        355                 360                 365

Lys

<210> SEQ ID NO 38
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 38 atg gtt tcg tat aac agc aag ttc ctc gcg gca acc gtt cag gca gag      48
Met Val Ser Tyr Asn Ser Lys Phe Leu Ala Ala Thr Val Gln Ala Glu
1               5                   10                  15 ccg gta tgg ctc gac gca gac gca acg atc gac aag tcg atc ggc atc      96
Pro Val Trp Leu Asp Ala Asp Ala Thr Ile Asp Lys Ser Ile Gly Ile
            20                  25                  30 atc gaa gaa gct gcc caa aag ggc gcg agt ctg atc gct ttc ccg gaa     144
Ile Glu Glu Ala Ala Gln Lys Gly Ala Ser Leu Ile Ala Phe Pro Glu
        35                  40                  45 gta ttc att ccg ggc tac ccc tat tgg gcg tgg ctc ggc gac gtg aag     192
Val Phe Ile Pro Gly Tyr Pro Tyr Trp Ala Trp Leu Gly Asp Val Lys
    50                  55                  60 tac agc cta agc ttt act tca cgc tat cac gag aat tcg ttg gag cta     240
Tyr Ser Leu Ser Phe Thr Ser Arg Tyr His Glu Asn Ser Leu Glu Leu
65                  70                  75                  80 ggt gac gac cgt atg cgt cgc ctc cag ctg gcc gcg cgc cgc aac aaa     288
Gly Asp Asp Arg Met Arg Arg Leu Gln Leu Ala Ala Arg Arg Asn Lys
                85                  90                  95 atc gca ctc gtc atg ggc tat tcg gag cgg gaa gcc gga tcg cgc tat     336
Ile Ala Leu Val Met Gly Tyr Ser Glu Arg Glu Ala Gly Ser Arg Tyr
            100                 105                 110 ctg agc cag gtg ttc atc gac gag cgt ggc gag atc gtt gcc aat cgg     384
Leu Ser Gln Val Phe Ile Asp Glu Arg Gly Glu Ile Val Ala Asn Arg
        115                 120                 125 cgc aag ctg aag ccc aca cac gtt gag cgt acg atc tac ggc gaa ggc     432
Arg Lys Leu Lys Pro Thr His Val Glu Arg Thr Ile Tyr Gly Glu Gly
    130                 135                 140 aac gga acc gat ttc ctc acg cac gac ttc gcg ttc gga cgc gtc ggt     480
Asn Gly Thr Asp Phe Leu Thr His Asp Phe Ala Phe Gly Arg Val Gly
145                 150                 155                 160 gga ttg aac tgc tgg gaa cat ttc caa ccg ctc agc aag ttc atg atg     528
Gly Leu Asn Cys Trp Glu His Phe Gln Pro Leu Ser Lys Phe Met Met
                165                 170                 175 tac agc ctc ggt gag cag gtc cac gtt gca tcg tgg ccg gcg atg tcc     576
Tyr Ser Leu Gly Glu Gln Val His Val Ala Ser Trp Pro Ala Met Ser
            180                 185                 190 cct ctt cag ccg gat gtt ttc caa aag agc atc gaa gcc aac gcg acg     624
Pro Leu Gln Pro Asp Val Phe Gln Lys Ser Ile Glu Ala Asn Ala Thr
        195                 200                 205 gtc acc cgc tcg tac gca atc gaa ggc caa acc ttt gtg ctt tgc tcg     672
Val Thr Arg Ser Tyr Ala Ile Glu Gly Gln Thr Phe Val Leu Cys Ser
    210                 215                 220 acg cag gtg atc gga cct agc gcg atc gaa acg ttc tgc ctc aac gac     720
Thr Gln Val Ile Gly Pro Ser Ala Ile Glu Thr Phe Cys Leu Asn Asp
225                 230                 235                 240 gaa cag cgc gca ctg ttg ccg caa gga tgt ggc tgg gcg cgc att tac     768
Glu Gln Arg Ala Leu Leu Pro Gln Gly Cys Gly Trp Ala Arg Ile Tyr
```

-continued

```
                              245                 250                 255
ggc ccg gat gga agc gag ctt gcg aag cct ctg gcg gaa gat gct gag        816
Gly Pro Asp Gly Ser Glu Leu Ala Lys Pro Leu Ala Glu Asp Ala Glu
            260                 265                 270 ggg atc ttg tac gca gag atc gat ctg gag cag att ctg ctg gcg aag        864
Gly Ile Leu Tyr Ala Glu Ile Asp Leu Glu Gln Ile Leu Leu Ala Lys
                275                 280                 285 gct gga gcc gat ccg gtc ggg cac tat tcg cgg cct gac gtg ctg tcg        912
Ala Gly Ala Asp Pro Val Gly His Tyr Ser Arg Pro Asp Val Leu Ser
        290                 295                 300 gtc cag ttc gac ccg cgc aat cat acg cca gtt cat cgc atc ggc att        960
Val Gln Phe Asp Pro Arg Asn His Thr Pro Val His Arg Ile Gly Ile
305                 310                 315                 320 gac ggt cgc ttg gat gtg aat acc cgc agt cgc gtg gag aat ttc cga       1008
Asp Gly Arg Leu Asp Val Asn Thr Arg Ser Arg Val Glu Asn Phe Arg
                325                 330                 335 ctg cga caa gcg gct gag cag gag cgt cag gca tcc aag cgg ctc gga       1056
Leu Arg Gln Ala Ala Glu Gln Glu Arg Gln Ala Ser Lys Arg Leu Gly
            340                 345                 350 acg aaa ctc ttt gaa caa tcc ctt ctg gct gaa gaa ccg gtc cca gca       1104
Thr Lys Leu Phe Glu Gln Ser Leu Leu Ala Glu Glu Pro Val Pro Ala
        355                 360                 365 aag tag                                                                1110
Lys
```

<210> SEQ ID NO 39
<211> LENGTH: 369
<212> TYPE: PRT
<213> ORGANISM: Acidovorax facilis 72W

<400> SEQUENCE: 39

```
Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Lys Ser Ile Glu Ala Asn Ala Thr
        195                 200                 205
```

-continued

```
Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
    290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Glu Pro Val Pro Ala
        355                 360                 365

Lys
```

<210> SEQ ID NO 40
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 40

```
atg gtt tcg tat aac agc aag ttc ctc gcg gca acc gtt cag gca gag        48
Met Val Ser Tyr Asn Ser Lys Phe Leu Ala Ala Thr Val Gln Ala Glu
1               5                   10                  15 ccg gta tgg ctc gac gca gac gca acg atc gac aag tcg atc ggc atc        96
Pro Val Trp Leu Asp Ala Asp Ala Thr Ile Asp Lys Ser Ile Gly Ile
            20                  25                  30 atc gaa gaa gct gcc caa aag ggc gcg agt ctg atc gct ttc ccg gaa       144
Ile Glu Glu Ala Ala Gln Lys Gly Ala Ser Leu Ile Ala Phe Pro Glu
        35                  40                  45 gta ttc att ccg ggc tac ccc tat tgg gcg tgg ctc ggc gac gtg aag       192
Val Phe Ile Pro Gly Tyr Pro Tyr Trp Ala Trp Leu Gly Asp Val Lys
    50                  55                  60 tac agc cta agc ttt act tca cgc tat cac gag aat tcg ttg gag cta       240
Tyr Ser Leu Ser Phe Thr Ser Arg Tyr His Glu Asn Ser Leu Glu Leu
65                  70                  75                  80 ggt gac gac cgt atg cgt cgc ctc cag ctg gcc gcg cgc cgc aac aaa       288
Gly Asp Asp Arg Met Arg Arg Leu Gln Leu Ala Ala Arg Arg Asn Lys
                85                  90                  95 atc gca ctc gtc atg ggc tat tcg gag cgg gaa gcc gga tcg cgc tat       336
Ile Ala Leu Val Met Gly Tyr Ser Glu Arg Glu Ala Gly Ser Arg Tyr
            100                 105                 110 ctg agc cag gtg ttc atc gac gag cgt ggc gag atc gtt gcc aat cgg       384
Leu Ser Gln Val Phe Ile Asp Glu Arg Gly Glu Ile Val Ala Asn Arg
        115                 120                 125 cgc aag ctg aag ccc aca cac gtt gag cgt acg atc tac ggc gaa ggc       432
Arg Lys Leu Lys Pro Thr His Val Glu Arg Thr Ile Tyr Gly Glu Gly
    130                 135                 140
```

```
aac gga acc gat ttc ctc acg cac gac ttc gcg ttc gga cgc gtc ggt      480
Asn Gly Thr Asp Phe Leu Thr His Asp Phe Ala Phe Gly Arg Val Gly
145                 150                 155                 160 gga ttg aac tgc tgg gaa cat ttc caa ccg ctc agc aag ttc atg atg      528
Gly Leu Asn Cys Trp Glu His Phe Gln Pro Leu Ser Lys Phe Met Met
            165                 170                 175 tac agc ctc ggt gag cag gtc cac gtt gca tcg tgg ccg gcg atg tcc      576
Tyr Ser Leu Gly Glu Gln Val His Val Ala Ser Trp Pro Ala Met Ser
        180                 185                 190 cct ctt cag ccg gat gtt ttc caa aat agc atc gaa gcc aac gcg acg      624
Pro Leu Gln Pro Asp Val Phe Gln Asn Ser Ile Glu Ala Asn Ala Thr
    195                 200                 205 gtc acc cgc tcg tac gca atc gaa ggc caa acc ttt gtg ctt tgc tcg      672
Val Thr Arg Ser Tyr Ala Ile Glu Gly Gln Thr Phe Val Leu Cys Ser
210                 215                 220 acg cag gtg atc gga cct agc gcg atc gaa acg ttc tgc ctc aac gac      720
Thr Gln Val Ile Gly Pro Ser Ala Ile Glu Thr Phe Cys Leu Asn Asp
225                 230                 235                 240 gaa cag cgc gca ctg ttg ccg caa gga tgt ggc tgg gcg cgc att tac      768
Glu Gln Arg Ala Leu Leu Pro Gln Gly Cys Gly Trp Ala Arg Ile Tyr
            245                 250                 255 ggc ccg gat gga agc gag ctt gcg aag cct ctg gcg gaa gat gct gag      816
Gly Pro Asp Gly Ser Glu Leu Ala Lys Pro Leu Ala Glu Asp Ala Glu
        260                 265                 270 ggg atc ttg tac gca gag atc gat ctg gag cag att ctg ctg gcg aag      864
Gly Ile Leu Tyr Ala Glu Ile Asp Leu Glu Gln Ile Leu Leu Ala Lys
    275                 280                 285 gct gga gcc gat ccg gtc ggg cac tat tcg cgg cct gac gtg ctg tcg      912
Ala Gly Ala Asp Pro Val Gly His Tyr Ser Arg Pro Asp Val Leu Ser
290                 295                 300 gtc cag ttc gac ccg cgc aat cat acg cca gtt cat cgc atc ggc att      960
Val Gln Phe Asp Pro Arg Asn His Thr Pro Val His Arg Ile Gly Ile
305                 310                 315                 320 gac ggt cgc ttg gat gtg aat acc cgc agt cgc gtg gag aat ttc cga     1008
Asp Gly Arg Leu Asp Val Asn Thr Arg Ser Arg Val Glu Asn Phe Arg
            325                 330                 335 ctg cga caa gcg gct gag cag gag cgt cag gca tcc aag cgg ctc gga     1056
Leu Arg Gln Ala Ala Glu Gln Glu Arg Gln Ala Ser Lys Arg Leu Gly
        340                 345                 350 acg aaa ctc ttt gaa caa tcc ctt ctg gct gaa gaa ccg gtc cca gca     1104
Thr Lys Leu Phe Glu Gln Ser Leu Leu Ala Glu Glu Pro Val Pro Ala
    355                 360                 365 aag tag                                                             1110
Lys
```

<210> SEQ ID NO 41
<211> LENGTH: 369
<212> TYPE: PRT
<213> ORGANISM: Acidovorax facilis 72W

<400> SEQUENCE: 41

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
            115                 120                 125

Arg Lys Leu Lys Pro Thr His Val Glu Arg Thr Ile Tyr Gly Glu Gly
        130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Asn Ser Ile Glu Ala Asn Ala Thr
            195                 200                 205

Val Thr Arg Ser Tyr Ala Ile Glu Gly Gln Thr Phe Val Leu Cys Ser
210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Glu Pro Val Pro Ala
        355                 360                 365

Lys

<210> SEQ ID NO 42
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 42 atg gtt tcg tat aac agc aag ttc ctc gcg gca acc gtt cag gca gag     48
Met Val Ser Tyr Asn Ser Lys Phe Leu Ala Ala Thr Val Gln Ala Glu
1               5                   10                  15 ccg gta tgg ctc gac gca gac gca acg atc gac aag tcg atc ggc atc     96
Pro Val Trp Leu Asp Ala Asp Ala Thr Ile Asp Lys Ser Ile Gly Ile
            20                  25                  30

```
atc gaa gaa gct gcc caa aag ggc gcg agt ctg atc gct ttc ccg gaa    144
Ile Glu Glu Ala Ala Gln Lys Gly Ala Ser Leu Ile Ala Phe Pro Glu
         35                  40                  45 gta ttc att ccg ggc tac ccc tat tgg gcg tgg ctc ggc gac gtg aag    192
Val Phe Ile Pro Gly Tyr Pro Tyr Trp Ala Trp Leu Gly Asp Val Lys
 50                  55                  60 tac agc cta agc ttt act tca cgc tat cac gag aat tcg ttg gag cta    240
Tyr Ser Leu Ser Phe Thr Ser Arg Tyr His Glu Asn Ser Leu Glu Leu
 65                  70                  75                  80 ggt gac gac cgt atg cgt cgc ctc cag ctg gcc gcg cgc cgc aac aaa    288
Gly Asp Asp Arg Met Arg Arg Leu Gln Leu Ala Ala Arg Arg Asn Lys
                 85                  90                  95 atc gca ctc gtc atg ggc tat tcg gag cgg gaa gcc gga tcg cgc tat    336
Ile Ala Leu Val Met Gly Tyr Ser Glu Arg Glu Ala Gly Ser Arg Tyr
        100                 105                 110 ctg agc cag gtg ttc atc gac gag cgt ggc gag atc gtt gcc aat cgg    384
Leu Ser Gln Val Phe Ile Asp Glu Arg Gly Glu Ile Val Ala Asn Arg
        115                 120                 125 cgc aag ctg aag ccc aca cac gtt gag cgt acg atc tac ggc gaa ggc    432
Arg Lys Leu Lys Pro Thr His Val Glu Arg Thr Ile Tyr Gly Glu Gly
130                 135                 140 aac gga acc gat ttc ctc acg cac gac ttc gcg ttc gga cgc gtc ggt    480
Asn Gly Thr Asp Phe Leu Thr His Asp Phe Ala Phe Gly Arg Val Gly
145                 150                 155                 160 gga ttg aac tgc tgg gaa cat ttc caa ccg ctc agc aag ttc atg atg    528
Gly Leu Asn Cys Trp Glu His Phe Gln Pro Leu Ser Lys Phe Met Met
                165                 170                 175 tac agc ctc ggt gag cag gtc cac gtt gca tcg tgg ccg gcg atg tcc    576
Tyr Ser Leu Gly Glu Gln Val His Val Ala Ser Trp Pro Ala Met Ser
                180                 185                 190 cct ctt cag ccg gat gtt ttc caa tct agc atc gaa gcc aac gcg acg    624
Pro Leu Gln Pro Asp Val Phe Gln Ser Ser Ile Glu Ala Asn Ala Thr
        195                 200                 205 gtc acc cgc tcg tac gca atc gaa ggc caa acc ttt gtg ctt tgc tcg    672
Val Thr Arg Ser Tyr Ala Ile Glu Gly Gln Thr Phe Val Leu Cys Ser
        210                 215                 220 acg cag gtg atc gga cct agc gcg atc gaa acg ttc tgc ctc aac gac    720
Thr Gln Val Ile Gly Pro Ser Ala Ile Glu Thr Phe Cys Leu Asn Asp
225                 230                 235                 240 gaa cag cgc gca ctg ttg ccg caa gga tgt ggc tgg gcg cgc att tac    768
Glu Gln Arg Ala Leu Leu Pro Gln Gly Cys Gly Trp Ala Arg Ile Tyr
                245                 250                 255 ggc ccg gat gga agc gag ctt gcg aag cct ctg gcg gaa gat gct gag    816
Gly Pro Asp Gly Ser Glu Leu Ala Lys Pro Leu Ala Glu Asp Ala Glu
                260                 265                 270 ggg atc ttg tac gca gag atc gat ctg gag cag att ctg ctg gcg aag    864
Gly Ile Leu Tyr Ala Glu Ile Asp Leu Glu Gln Ile Leu Leu Ala Lys
        275                 280                 285 gct gga gcc gat ccg gtc ggg cac tat tcg cgg cct gac gtg ctg tcg    912
Ala Gly Ala Asp Pro Val Gly His Tyr Ser Arg Pro Asp Val Leu Ser
        290                 295                 300 gtc cag ttc gac ccg cgc aat cat acg cca gtt cat cgc atc ggc att    960
Val Gln Phe Asp Pro Arg Asn His Thr Pro Val His Arg Ile Gly Ile
305                 310                 315                 320 gac ggt cgc ttg gat gtg aat acc cgc agt cgc gtg gag aat ttc cga    1008
Asp Gly Arg Leu Asp Val Asn Thr Arg Ser Arg Val Glu Asn Phe Arg
                325                 330                 335 ctg cga caa gcg gct gag cag gag cgt cag gca tcc aag cgg ctc gga    1056
Leu Arg Gln Ala Ala Glu Gln Glu Arg Gln Ala Ser Lys Arg Leu Gly
                340                 345                 350
```

```
acg aaa ctc ttt gaa caa tcc ctt ctg gct gaa gaa ccg gtc cca gca    1104
Thr Lys Leu Phe Glu Gln Ser Leu Leu Ala Glu Glu Pro Val Pro Ala
        355                 360                 365 aag tag                                                             1110
Lys
```

<210> SEQ ID NO 43
<211> LENGTH: 369
<212> TYPE: PRT
<213> ORGANISM: Acidovorax facilis 72W

<400> SEQUENCE: 43

```
Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Ser Ser Ile Glu Ala Asn Ala Thr
        195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
    290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335
```

```
Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Glu Pro Val Pro Ala
            355                 360                 365

Lys

<210> SEQ ID NO 44
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 44
```

| | | | | | | | | | | | | | | | | |
|---|---|---|---|---|---|---|---|---|---|---|---|---|---|---|---|---|
| atg | gtt | tcg | tat | aac | agc | aag | ttc | ctc | gcg | gca | acc | gtt | cag | gca | gag | 48 |
| Met | Val | Ser | Tyr | Asn | Ser | Lys | Phe | Leu | Ala | Ala | Thr | Val | Gln | Ala | Glu | |
| 1 | | | | 5 | | | | | 10 | | | | | 15 | | |
| ccg | gta | tgg | ctc | gac | gca | gac | gca | acg | atc | gac | aag | tcg | atc | ggc | atc | 96 |
| Pro | Val | Trp | Leu | Asp | Ala | Asp | Ala | Thr | Ile | Asp | Lys | Ser | Ile | Gly | Ile | |
| | | | 20 | | | | | 25 | | | | | 30 | | | |
| atc | gaa | gaa | gct | gcc | caa | aag | ggc | gcg | agt | ctg | atc | gct | ttc | ccg | gaa | 144 |
| Ile | Glu | Glu | Ala | Ala | Gln | Lys | Gly | Ala | Ser | Leu | Ile | Ala | Phe | Pro | Glu | |
| | | 35 | | | | | 40 | | | | | 45 | | | | |
| gta | ttc | att | ccg | ggc | tac | ccc | tat | tgg | gcg | tgg | ctc | ggc | gac | gtg | aag | 192 |
| Val | Phe | Ile | Pro | Gly | Tyr | Pro | Tyr | Trp | Ala | Trp | Leu | Gly | Asp | Val | Lys | |
| | 50 | | | | | 55 | | | | | 60 | | | | | |
| tac | agc | cta | agc | ttt | act | tca | cgc | tat | cac | gag | aat | tcg | ttg | gag | cta | 240 |
| Tyr | Ser | Leu | Ser | Phe | Thr | Ser | Arg | Tyr | His | Glu | Asn | Ser | Leu | Glu | Leu | |
| 65 | | | | | 70 | | | | | 75 | | | | | 80 | |
| ggt | gac | gac | cgt | atg | cgt | cgc | ctc | cag | ctg | gcc | gcg | cgc | cgc | aac | aaa | 288 |
| Gly | Asp | Asp | Arg | Met | Arg | Arg | Leu | Gln | Leu | Ala | Ala | Arg | Arg | Asn | Lys | |
| | | | | 85 | | | | | 90 | | | | | 95 | | |
| atc | gca | ctc | gtc | atg | ggc | tat | tcg | gag | cgg | gaa | gcc | gga | tcg | cgc | tat | 336 |
| Ile | Ala | Leu | Val | Met | Gly | Tyr | Ser | Glu | Arg | Glu | Ala | Gly | Ser | Arg | Tyr | |
| | | | 100 | | | | | 105 | | | | | 110 | | | |
| ctg | agc | cag | gtg | ttc | atc | gac | gag | cgt | ggc | gag | atc | gtt | gcc | aat | cgg | 384 |
| Leu | Ser | Gln | Val | Phe | Ile | Asp | Glu | Arg | Gly | Glu | Ile | Val | Ala | Asn | Arg | |
| | | 115 | | | | | 120 | | | | | 125 | | | | |
| cgc | aag | ctg | aag | ccc | aca | cac | gtt | gag | cgt | acg | atc | tac | ggc | gaa | ggc | 432 |
| Arg | Lys | Leu | Lys | Pro | Thr | His | Val | Glu | Arg | Thr | Ile | Tyr | Gly | Glu | Gly | |
| | 130 | | | | | 135 | | | | | 140 | | | | | |
| aac | gga | acc | gat | ttc | ctc | acg | cac | gac | ttc | gcg | ttc | gga | cgc | gtc | ggt | 480 |
| Asn | Gly | Thr | Asp | Phe | Leu | Thr | His | Asp | Phe | Ala | Phe | Gly | Arg | Val | Gly | |
| 145 | | | | | 150 | | | | | 155 | | | | | 160 | |
| gga | ttg | aac | tgc | tgg | gaa | cat | aaa | caa | ccg | ctc | agc | aag | ttc | atg | atg | 528 |
| Gly | Leu | Asn | Cys | Trp | Glu | His | Lys | Gln | Pro | Leu | Ser | Lys | Phe | Met | Met | |
| | | | | 165 | | | | | 170 | | | | | 175 | | |
| tac | agc | ctc | ggt | gag | cag | gtc | cac | gtt | gca | tcg | tgg | ccg | gcg | atg | tcc | 576 |
| Tyr | Ser | Leu | Gly | Glu | Gln | Val | His | Val | Ala | Ser | Trp | Pro | Ala | Met | Ser | |
| | | | 180 | | | | | 185 | | | | | 190 | | | |
| cct | ctt | cag | ccg | gat | gtt | ttc | caa | ctg | agc | atc | gaa | gcc | aac | gcg | acg | 624 |
| Pro | Leu | Gln | Pro | Asp | Val | Phe | Gln | Leu | Ser | Ile | Glu | Ala | Asn | Ala | Thr | |
| | | 195 | | | | | 200 | | | | | 205 | | | | |
| gtc | acc | cgc | tcg | tac | gca | atc | gaa | ggc | caa | acc | ttt | gtg | ctt | tgc | tcg | 672 |
| Val | Thr | Arg | Ser | Tyr | Ala | Ile | Glu | Gly | Gln | Thr | Phe | Val | Leu | Cys | Ser | |
| | 210 | | | | | 215 | | | | | 220 | | | | | |
| acg | cag | gtg | atc | gga | cct | agc | gcg | atc | gaa | acg | ttc | tgc | ctc | aac | gac | 720 |
| Thr | Gln | Val | Ile | Gly | Pro | Ser | Ala | Ile | Glu | Thr | Phe | Cys | Leu | Asn | Asp | |
| 225 | | | | | 230 | | | | | 235 | | | | | 240 | |

```
gaa cag cgc gca ctg ttg ccg caa gga tgt ggc tgg gcg cgc att tac      768
Glu Gln Arg Ala Leu Leu Pro Gln Gly Cys Gly Trp Ala Arg Ile Tyr
            245                 250                 255 ggc ccg gat gga agc gag ctt gcg aag cct ctg gcg gaa gat gct gag      816
Gly Pro Asp Gly Ser Glu Leu Ala Lys Pro Leu Ala Glu Asp Ala Glu
        260                 265                 270 ggg atc ttg tac gca gag atc gat ctg gag cag att ctg ctg gcg aag      864
Gly Ile Leu Tyr Ala Glu Ile Asp Leu Glu Gln Ile Leu Leu Ala Lys
    275                 280                 285 gct gga gcc gat ccg gtc ggg cac tat tcg cgg cct gac gtg ctg tcg      912
Ala Gly Ala Asp Pro Val Gly His Tyr Ser Arg Pro Asp Val Leu Ser
290                 295                 300 gtc cag ttc gac ccg cgc aat cat acg cca gtt cat cgc atc ggc att      960
Val Gln Phe Asp Pro Arg Asn His Thr Pro Val His Arg Ile Gly Ile
305                 310                 315                 320 gac ggt cgc ttg gat gtg aat acc cgc agt cgc gtg gag aat ttc cga     1008
Asp Gly Arg Leu Asp Val Asn Thr Arg Ser Arg Val Glu Asn Phe Arg
                325                 330                 335 ctg cga caa gcg gct gag cag gag cgt cag gca tcc aag cgg ctc gga     1056
Leu Arg Gln Ala Ala Glu Gln Glu Arg Gln Ala Ser Lys Arg Leu Gly
            340                 345                 350 acg aaa ctc ttt gaa caa tcc ctt ctg gct gaa gaa ccg gtc cca gca     1104
Thr Lys Leu Phe Glu Gln Ser Leu Leu Ala Glu Glu Pro Val Pro Ala
        355                 360                 365 aag tag                                                             1110
Lys
```

<210> SEQ ID NO 45
<211> LENGTH: 369
<212> TYPE: PRT
<213> ORGANISM: Acidovorax facilis 72W

<400> SEQUENCE: 45

```
Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Lys Gln Pro Leu Ser Lys Phe Met Met
                165                 170                 175

Tyr Ser Leu Gly Glu Gln Val His Val Ala Ser Trp Pro Ala Met Ser
            180                 185                 190
```

```
Pro Leu Gln Pro Asp Val Phe Gln Leu Ser Ile Glu Ala Asn Ala Thr
        195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
    290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Glu Pro Val Pro Ala
        355                 360                 365

Lys

<210> SEQ ID NO 46
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 46 atg gtt tcg tat aac agc aag ttc ctc gcg gca acc gtt cag gca gag      48
Met Val Ser Tyr Asn Ser Lys Phe Leu Ala Ala Thr Val Gln Ala Glu
1               5                   10                  15 ccg gta tgg ctc gac gca gac gca acg atc gac aag tcg atc ggc atc      96
Pro Val Trp Leu Asp Ala Asp Ala Thr Ile Asp Lys Ser Ile Gly Ile
            20                  25                  30 atc gaa gaa gct gcc caa aag ggc gcg agt ctg atc gct ttc ccg gaa     144
Ile Glu Glu Ala Ala Gln Lys Gly Ala Ser Leu Ile Ala Phe Pro Glu
        35                  40                  45 gta ttc att ccg ggc tac ccc tat tgg gcg tgg ctc ggc gac gtg aag     192
Val Phe Ile Pro Gly Tyr Pro Tyr Trp Ala Trp Leu Gly Asp Val Lys
    50                  55                  60 tac agc cta agc ttt act tca cgc tat cac gag aat tcg ttg gag cta     240
Tyr Ser Leu Ser Phe Thr Ser Arg Tyr His Glu Asn Ser Leu Glu Leu
65                  70                  75                  80 ggt gac gac cgt atg cgt cgc ctc cag ctg gcc gcg cgc cgc aac aaa     288
Gly Asp Asp Arg Met Arg Arg Leu Gln Leu Ala Ala Arg Arg Asn Lys
                85                  90                  95 atc gca ctc gtc atg ggc tat tcg gag cgg gaa gcc gga tcg cgc tat     336
Ile Ala Leu Val Met Gly Tyr Ser Glu Arg Glu Ala Gly Ser Arg Tyr
            100                 105                 110 ctg agc cag gtg ttc atc gac gag cgt ggc gag atc gtt gcc aat cgg     384
Leu Ser Gln Val Phe Ile Asp Glu Arg Gly Glu Ile Val Ala Asn Arg
        115                 120                 125 cgc aag ctg aag ccc aca cac gtt gag cgt acg atc tac ggc gaa ggc     432
```

```
                Arg Lys Leu Lys Pro Thr His Val Glu Arg Thr Ile Tyr Gly Glu Gly
                    130                 135                 140 aac gga acc gat ttc ctc acg cac gac ttc gcg ttc gga cgc gtc ggt        480
Asn Gly Thr Asp Phe Leu Thr His Asp Phe Ala Phe Gly Arg Val Gly
145                 150                 155                 160 gga ttg aac tgc tgg gaa cat atg caa ccg ctc agc aag ttc atg atg        528
Gly Leu Asn Cys Trp Glu His Met Gln Pro Leu Ser Lys Phe Met Met
                165                 170                 175 tac agc ctc ggt gag cag gtc cac gtt gca tcg tgg ccg gcg atg tcc        576
Tyr Ser Leu Gly Glu Gln Val His Val Ala Ser Trp Pro Ala Met Ser
            180                 185                 190 cct ctt cag ccg gat gtt ttc caa ctg agc atc gaa gcc aac gcg acg        624
Pro Leu Gln Pro Asp Val Phe Gln Leu Ser Ile Glu Ala Asn Ala Thr
        195                 200                 205 gtc acc cgc tcg tac gca atc gaa ggc caa acc ttt gtg ctt tgc tcg        672
Val Thr Arg Ser Tyr Ala Ile Glu Gly Gln Thr Phe Val Leu Cys Ser
    210                 215                 220 acg cag gtg atc gga cct agc gcg atc gaa acg ttc tgc ctc aac gac        720
Thr Gln Val Ile Gly Pro Ser Ala Ile Glu Thr Phe Cys Leu Asn Asp
225                 230                 235                 240 gaa cag cgc gca ctg ttg ccg caa gga tgt ggc tgg gcg cgc att tac        768
Glu Gln Arg Ala Leu Leu Pro Gln Gly Cys Gly Trp Ala Arg Ile Tyr
                245                 250                 255 ggc ccg gat gga agc gag ctt gcg aag cct ctg gcg gaa gat gct gag        816
Gly Pro Asp Gly Ser Glu Leu Ala Lys Pro Leu Ala Glu Asp Ala Glu
            260                 265                 270 ggg atc ttg tac gca gag atc gat ctg gag cag att ctg ctg gcg aag        864
Gly Ile Leu Tyr Ala Glu Ile Asp Leu Glu Gln Ile Leu Leu Ala Lys
        275                 280                 285 gct gga gcc gat ccg gtc ggg cac tat tcg cgg cct gac gtg ctg tcg        912
Ala Gly Ala Asp Pro Val Gly His Tyr Ser Arg Pro Asp Val Leu Ser
    290                 295                 300 gtc cag ttc gac ccg cgc aat cat acg cca gtt cat cgc atc ggc att        960
Val Gln Phe Asp Pro Arg Asn His Thr Pro Val His Arg Ile Gly Ile
305                 310                 315                 320 gac ggt cgc ttg gat gtg aat acc cgc agt cgc gtg gag aat ttc cga       1008
Asp Gly Arg Leu Asp Val Asn Thr Arg Ser Arg Val Glu Asn Phe Arg
                325                 330                 335 ctg cga caa gcg gct gag cag gag cgt cag gca tcc aag cgg ctc gga       1056
Leu Arg Gln Ala Ala Glu Gln Glu Arg Gln Ala Ser Lys Arg Leu Gly
            340                 345                 350 acg aaa ctc ttt gaa caa tcc ctt ctg gct gaa gaa ccg gtc cca gca       1104
Thr Lys Leu Phe Glu Gln Ser Leu Leu Ala Glu Glu Pro Val Pro Ala
        355                 360                 365 aag tag                                                                1110
Lys

<210> SEQ ID NO 47
<211> LENGTH: 369
<212> TYPE: PRT
<213> ORGANISM: Acidovorax facilis 72W

<400> SEQUENCE: 47

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45
```

-continued

```
Val Phe Ile Pro Gly Tyr Pro Tyr Trp Ala Trp Leu Gly Asp Val Lys
 50                  55                  60

Tyr Ser Leu Ser Phe Thr Ser Arg Tyr His Glu Asn Ser Leu Glu Leu
 65                  70                  75                  80

Gly Asp Asp Arg Met Arg Arg Leu Gln Leu Ala Ala Arg Arg Asn Lys
                 85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
130                 135                 140

Asn Gly Thr Asp Phe Leu Thr His Asp Phe Ala Phe Gly Arg Val Gly
145                 150                 155                 160

Gly Leu Asn Cys Trp Glu His Met Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Leu Ser Ile Glu Ala Asn Ala Thr
        195                 200                 205

Val Thr Arg Ser Tyr Ala Ile Glu Gly Gln Thr Phe Val Leu Cys Ser
210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Pro Val Pro Ala
        355                 360                 365

Lys
```

<210> SEQ ID NO 48
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 48

```
atg gtt tcg tat aac agc aag ttc ctc gcg gca acc gtt cag gca gag      48
Met Val Ser Tyr Asn Ser Lys Phe Leu Ala Ala Thr Val Gln Ala Glu
 1               5                  10                  15 ccg gta tgg ctc gac gca gac gca acg atc gac aag tcg atc ggc atc      96
Pro Val Trp Leu Asp Ala Asp Ala Thr Ile Asp Lys Ser Ile Gly Ile
```

-continued

```
                    20                  25                  30
atc gaa gaa gct gcc caa aag ggc gcg agt ctg atc gct ttc ccg gaa      144
Ile Glu Glu Ala Ala Gln Lys Gly Ala Ser Leu Ile Ala Phe Pro Glu
             35                  40                  45 gta ttc att ccg ggc tac ccc tat tgg gcg tgg ctc ggc gac gtg aag      192
Val Phe Ile Pro Gly Tyr Pro Tyr Trp Ala Trp Leu Gly Asp Val Lys
 50                  55                  60 tac agc cta agc ttt act tca cgc tat cac gag aat tcg ttg gag cta      240
Tyr Ser Leu Ser Phe Thr Ser Arg Tyr His Glu Asn Ser Leu Glu Leu
 65                  70                  75                  80 ggt gac gac cgt atg cgt cgc ctc cag ctg gcc gcg cgc cgc aac aaa      288
Gly Asp Asp Arg Met Arg Arg Leu Gln Leu Ala Ala Arg Arg Asn Lys
                 85                  90                  95 atc gca ctc gtc atg ggc tat tcg gag cgg gaa gcc gga tcg cgc tat      336
Ile Ala Leu Val Met Gly Tyr Ser Glu Arg Glu Ala Gly Ser Arg Tyr
            100                 105                 110 ctg agc cag gtg ttc atc gac gag cgt ggc gag atc gtt gcc aat cgg      384
Leu Ser Gln Val Phe Ile Asp Glu Arg Gly Glu Ile Val Ala Asn Arg
            115                 120                 125 cgc aag ctg aag ccc aca cac gtt gag cgt acg atc tac ggc gaa ggc      432
Arg Lys Leu Lys Pro Thr His Val Glu Arg Thr Ile Tyr Gly Glu Gly
       130                 135                 140 aac gga acc gat ttc ctc acg cac gac ttc gcg ttc gga cgc gtc ggt      480
Asn Gly Thr Asp Phe Leu Thr His Asp Phe Ala Phe Gly Arg Val Gly
145                 150                 155                 160 gga ttg aac tgc tgg gaa cat acc caa ccg ctc agc aag ttc atg atg      528
Gly Leu Asn Cys Trp Glu His Thr Gln Pro Leu Ser Lys Phe Met Met
                165                 170                 175 tac agc ctc ggt gag cag gtc cac gtt gca tcg tgg ccg gcg atg tcc      576
Tyr Ser Leu Gly Glu Gln Val His Val Ala Ser Trp Pro Ala Met Ser
            180                 185                 190 cct ctt cag ccg gat gtt ttc caa ctg agc atc gaa gcc aac gcg acg      624
Pro Leu Gln Pro Asp Val Phe Gln Leu Ser Ile Glu Ala Asn Ala Thr
            195                 200                 205 gtc acc cgc tcg tac gca atc gaa ggc caa acc ttt gtg ctt tgc tcg      672
Val Thr Arg Ser Tyr Ala Ile Glu Gly Gln Thr Phe Val Leu Cys Ser
       210                 215                 220 acg cag gtg atc gga cct agc gcg atc gaa acg ttc tgc ctc aac gac      720
Thr Gln Val Ile Gly Pro Ser Ala Ile Glu Thr Phe Cys Leu Asn Asp
225                 230                 235                 240 gaa cag cgc gca ctg ttg ccg caa gga tgt ggc tgg gcg cgc att tac      768
Glu Gln Arg Ala Leu Leu Pro Gln Gly Cys Gly Trp Ala Arg Ile Tyr
                245                 250                 255 ggc ccg gat gga agc gag ctt gcg aag cct ctg gcg gaa gat gct gag      816
Gly Pro Asp Gly Ser Glu Leu Ala Lys Pro Leu Ala Glu Asp Ala Glu
            260                 265                 270 ggg atc ttg tac gca gag atc gat ctg gag cag att ctg ctg gcg aag      864
Gly Ile Leu Tyr Ala Glu Ile Asp Leu Glu Gln Ile Leu Leu Ala Lys
            275                 280                 285 gct gga gcc gat ccg gtc ggg cac tat tcg cgg cct gac gtg ctg tcg      912
Ala Gly Ala Asp Pro Val Gly His Tyr Ser Arg Pro Asp Val Leu Ser
       290                 295                 300 gtc cag ttc gac ccg cgc aat cat acg cca gtt cat cgc atc ggc att      960
Val Gln Phe Asp Pro Arg Asn His Thr Pro Val His Arg Ile Gly Ile
305                 310                 315                 320 gac ggt cgc ttg gat gtg aat acc cgc agt cgc gtg gag aat ttc cga     1008
Asp Gly Arg Leu Asp Val Asn Thr Arg Ser Arg Val Glu Asn Phe Arg
                325                 330                 335 ctg cga caa gcg gct gag cag gag cgt cag gca tcc aag cgg ctc gga     1056
```

```
Leu Arg Gln Ala Ala Glu Gln Glu Arg Gln Ala Ser Lys Arg Leu Gly
            340                 345                 350 acg aaa ctc ttt gaa caa tcc ctt ctg gct gaa gaa ccg gtc cca gca      1104
Thr Lys Leu Phe Glu Gln Ser Leu Leu Ala Glu Glu Pro Val Pro Ala
            355                 360                 365 aag tag                                                              1110
Lys

<210> SEQ ID NO 49
<211> LENGTH: 369
<212> TYPE: PRT
<213> ORGANISM: Acidovorax facilis 72W

<400> SEQUENCE: 49

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Thr Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Leu Ser Ile Glu Ala Asn Ala Thr
        195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
    290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
```

```
                        325                 330                 335
Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Glu Pro Val Pro Ala
            355                 360                 365

Lys

<210> SEQ ID NO 50
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 50 atg gtt tcg tat aac agc aag ttc ctc gcg gca acc gtt cag gca gag      48
Met Val Ser Tyr Asn Ser Lys Phe Leu Ala Ala Thr Val Gln Ala Glu
1               5                  10                  15 ccg gta tgg ctc gac gca gac gca acg atc gac aag tcg atc ggc atc      96
Pro Val Trp Leu Asp Ala Asp Ala Thr Ile Asp Lys Ser Ile Gly Ile
            20                  25                  30 atc gaa gaa gct gcc caa aag ggc gcg agt ctg atc gct ttc ccg gaa     144
Ile Glu Glu Ala Ala Gln Lys Gly Ala Ser Leu Ile Ala Phe Pro Glu
        35                  40                  45 gta ttc att ccg ggc tac ccc tat tgg gcg tgg ctc ggc gac gtg aag     192
Val Phe Ile Pro Gly Tyr Pro Tyr Trp Ala Trp Leu Gly Asp Val Lys
    50                  55                  60 tac agc cta agc ttt act tca cgc tat cac gag aat tcg ttg gag cta     240
Tyr Ser Leu Ser Phe Thr Ser Arg Tyr His Glu Asn Ser Leu Glu Leu
65                  70                  75                  80 ggt gac gac cgt atg cgt cgc ctc cag ctg gcc gcg cgc cgc aac aaa     288
Gly Asp Asp Arg Met Arg Arg Leu Gln Leu Ala Ala Arg Arg Asn Lys
                85                  90                  95 atc gca ctc gtc atg ggc tat tcg gag cgg gaa gcc gga tcg cgc tat     336
Ile Ala Leu Val Met Gly Tyr Ser Glu Arg Glu Ala Gly Ser Arg Tyr
            100                 105                 110 ctg agc cag gtg ttc atc gac gag cgt ggc gag atc gtt gcc aat cgg     384
Leu Ser Gln Val Phe Ile Asp Glu Arg Gly Glu Ile Val Ala Asn Arg
        115                 120                 125 cgc aag ctg aag ccc aca cac gtt gag cgt acg atc tac ggc gaa ggc     432
Arg Lys Leu Lys Pro Thr His Val Glu Arg Thr Ile Tyr Gly Glu Gly
    130                 135                 140 aac gga acc gat ttc ctc acg cac gac ttc gcg ttc gga cgc gtc ggt     480
Asn Gly Thr Asp Phe Leu Thr His Asp Phe Ala Phe Gly Arg Val Gly
145                 150                 155                 160 gga ttg aac tgc tgg gaa cat gtg caa ccg ctc agc aag ttc atg atg     528
Gly Leu Asn Cys Trp Glu His Val Gln Pro Leu Ser Lys Phe Met Met
                165                 170                 175 tac agc ctc ggt gag cag gtc cac gtt gca tcg tgg ccg gcg atg tcc     576
Tyr Ser Leu Gly Glu Gln Val His Val Ala Ser Trp Pro Ala Met Ser
            180                 185                 190 cct ctt cag ccg gat gtt ttc caa ctg agc atc gaa gcc aac gcg acg     624
Pro Leu Gln Pro Asp Val Phe Gln Leu Ser Ile Glu Ala Asn Ala Thr
        195                 200                 205 gtc acc cgc tcg tac gca atc gaa ggc caa acc ttt gtg ctt tgc tcg     672
Val Thr Arg Ser Tyr Ala Ile Glu Gly Gln Thr Phe Val Leu Cys Ser
    210                 215                 220 acg cag gtg atc gga cct agc gcg atc gaa acg ttc tgc ctc aac gac     720
Thr Gln Val Ile Gly Pro Ser Ala Ile Glu Thr Phe Cys Leu Asn Asp
225                 230                 235                 240
```

```
                 225                 230                 235                 240
gaa cag cgc gca ctg ttg ccg caa gga tgt ggc tgg gcg cgc att tac       768
Glu Gln Arg Ala Leu Leu Pro Gln Gly Cys Gly Trp Ala Arg Ile Tyr
                245                 250                 255 ggc ccg gat gga agc gag ctt gcg aag cct ctg gcg gaa gat gct gag       816
Gly Pro Asp Gly Ser Glu Leu Ala Lys Pro Leu Ala Glu Asp Ala Glu
            260                 265                 270 ggg atc ttg tac gca gag atc gat ctg gag cag att ctg ctg gcg aag       864
Gly Ile Leu Tyr Ala Glu Ile Asp Leu Glu Gln Ile Leu Leu Ala Lys
                275                 280                 285 gct gga gcc gat ccg gtc ggg cac tat tcg cgg cct gac gtg ctg tcg       912
Ala Gly Ala Asp Pro Val Gly His Tyr Ser Arg Pro Asp Val Leu Ser
            290                 295                 300 gtc cag ttc gac ccg cgc aat cat acg cca gtt cat cgc atc ggc att       960
Val Gln Phe Asp Pro Arg Asn His Thr Pro Val His Arg Ile Gly Ile
305                 310                 315                 320 gac ggt cgc ttg gat gtg aat acc cgc agt cgc gtg gag aat ttc cga      1008
Asp Gly Arg Leu Asp Val Asn Thr Arg Ser Arg Val Glu Asn Phe Arg
                325                 330                 335 ctg cga caa gcg gct gag cag gag cgt cag gca tcc aag cgg ctc gga      1056
Leu Arg Gln Ala Ala Glu Gln Glu Arg Gln Ala Ser Lys Arg Leu Gly
            340                 345                 350 acg aaa ctc ttt gaa caa tcc ctt ctg gct gaa gaa ccg gtc cca gca      1104
Thr Lys Leu Phe Glu Gln Ser Leu Leu Ala Glu Glu Pro Val Pro Ala
                355                 360                 365 aag tag                                                              1110
Lys
```

<210> SEQ ID NO 51
<211> LENGTH: 369
<212> TYPE: PRT
<213> ORGANISM: Acidovorax facilis 72W

<400> SEQUENCE: 51

```
Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Val Gln Pro Leu Ser Lys Phe Met Met
                165                 170                 175

Tyr Ser Leu Gly Glu Gln Val His Val Ala Ser Trp Pro Ala Met Ser
```

-continued

```
                180                 185                 190
Pro Leu Gln Pro Asp Val Phe Gln Leu Ser Ile Glu Ala Asn Ala Thr
            195                 200                 205
Val Thr Arg Ser Tyr Ala Ile Glu Gly Gln Thr Phe Val Leu Cys Ser
        210                 215                 220
Thr Gln Val Ile Gly Pro Ser Ala Ile Glu Thr Phe Cys Leu Asn Asp
225                 230                 235                 240
Glu Gln Arg Ala Leu Leu Pro Gln Gly Cys Gly Trp Ala Arg Ile Tyr
                245                 250                 255
Gly Pro Asp Gly Ser Glu Leu Ala Lys Pro Leu Ala Glu Asp Ala Glu
            260                 265                 270
Gly Ile Leu Tyr Ala Glu Ile Asp Leu Glu Gln Ile Leu Leu Ala Lys
        275                 280                 285
Ala Gly Ala Asp Pro Val Gly His Tyr Ser Arg Pro Asp Val Leu Ser
    290                 295                 300
Val Gln Phe Asp Pro Arg Asn His Thr Pro Val His Arg Ile Gly Ile
305                 310                 315                 320
Asp Gly Arg Leu Asp Val Asn Thr Arg Ser Arg Val Glu Asn Phe Arg
                325                 330                 335
Leu Arg Gln Ala Ala Glu Gln Glu Arg Gln Ala Ser Lys Arg Leu Gly
            340                 345                 350
Thr Lys Leu Phe Glu Gln Ser Leu Leu Ala Glu Glu Pro Val Pro Ala
        355                 360                 365
Lys
```

<210> SEQ ID NO 52
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 52

```
atg gtt tcg tat aac agc aag ttc ctc gcg gca acc gtt cag gca gag       48
Met Val Ser Tyr Asn Ser Lys Phe Leu Ala Ala Thr Val Gln Ala Glu
1               5                   10                  15 ccg gta tgg ctc gac gca gac gca acg atc gac aag tcg atc ggc atc       96
Pro Val Trp Leu Asp Ala Asp Ala Thr Ile Asp Lys Ser Ile Gly Ile
                20                  25                  30 atc gaa gaa gct gcc caa aag ggc gcg agt ctg atc gct ttc ccg gaa      144
Ile Glu Glu Ala Ala Gln Lys Gly Ala Ser Leu Ile Ala Phe Pro Glu
            35                  40                  45 gta ttc att ccg ggc tac ccc tat tgg gcg tgg ctc ggc gac gtg aag      192
Val Phe Ile Pro Gly Tyr Pro Tyr Trp Ala Trp Leu Gly Asp Val Lys
        50                  55                  60 tac agc cta agc ttt act tca cgc tat cac gag aat tcg ttg gag cta      240
Tyr Ser Leu Ser Phe Thr Ser Arg Tyr His Glu Asn Ser Leu Glu Leu
65                  70                  75                  80 ggt gac gac cgt atg cgt cgc ctc cag ctg gcc gcg cgc cgc aac aaa      288
Gly Asp Asp Arg Met Arg Arg Leu Gln Leu Ala Ala Arg Arg Asn Lys
                85                  90                  95 atc gca ctc gtc atg ggc tat tcg gag cgg gaa gcc gga tcg cgc tat      336
Ile Ala Leu Val Met Gly Tyr Ser Glu Arg Glu Ala Gly Ser Arg Tyr
            100                 105                 110 ctg agc cag gtg ttc atc gac gag cgt ggc gag atc gtt gcc aat cgg      384
Leu Ser Gln Val Phe Ile Asp Glu Arg Gly Glu Ile Val Ala Asn Arg
        115                 120                 125
```

```
cgc aag ctg aag ccc aca cac gtt gag cgt acg atc tac ggc gaa ggc      432
Arg Lys Leu Lys Pro Thr His Val Glu Arg Thr Ile Tyr Gly Glu Gly
    130                 135                 140 aac gga acc gat ttc ctc acg cac gac ttc gcg ttc gga cgc gtc ggt      480
Asn Gly Thr Asp Phe Leu Thr His Asp Phe Ala Phe Gly Arg Val Gly
145                 150                 155                 160 gga ttg aac tgc tgg gaa cat ttc caa ccg ctc agc aag ttc atg atg      528
Gly Leu Asn Cys Trp Glu His Phe Gln Pro Leu Ser Lys Phe Met Met
                165                 170                 175 tac agc ctc ggt gag cag gtc cac gtt gca tcg tgg ccg gcg atg tcc      576
Tyr Ser Leu Gly Glu Gln Val His Val Ala Ser Trp Pro Ala Met Ser
            180                 185                 190 cct ctt cag ccg gat gtt ttc caa ctg agc atc gaa gcc aac gcg acg      624
Pro Leu Gln Pro Asp Val Phe Gln Leu Ser Ile Glu Ala Asn Ala Thr
        195                 200                 205 gtc gcc cgc tcg tac gca atc gaa ggc caa acc ttt gtg ctt tgc tcg      672
Val Ala Arg Ser Tyr Ala Ile Glu Gly Gln Thr Phe Val Leu Cys Ser
    210                 215                 220 acg cag gtg atc gga cct agc gcg atc gaa acg ttc tgc ctc aac gac      720
Thr Gln Val Ile Gly Pro Ser Ala Ile Glu Thr Phe Cys Leu Asn Asp
225                 230                 235                 240 gaa cag cgc gca ctg ttg ccg caa gga tgt ggc tgg gcg cgc att tac      768
Glu Gln Arg Ala Leu Leu Pro Gln Gly Cys Gly Trp Ala Arg Ile Tyr
                245                 250                 255 ggc ccg gat gga agc gag ctt gcg aag cct ctg gcg gaa gat gct gag      816
Gly Pro Asp Gly Ser Glu Leu Ala Lys Pro Leu Ala Glu Asp Ala Glu
            260                 265                 270 ggg atc ttg tac gca gag atc gat ctg gag cag att ctg ctg gcg aag      864
Gly Ile Leu Tyr Ala Glu Ile Asp Leu Glu Gln Ile Leu Leu Ala Lys
        275                 280                 285 gct gga gcc gat ccg gtc ggg cac tat tcg cgg cct gac gtg ctg tcg      912
Ala Gly Ala Asp Pro Val Gly His Tyr Ser Arg Pro Asp Val Leu Ser
    290                 295                 300 gtc cag ttc gac ccg cgc aat cat acg cca gtt cat cgc atc ggc att      960
Val Gln Phe Asp Pro Arg Asn His Thr Pro Val His Arg Ile Gly Ile
305                 310                 315                 320 gac ggt cgc ttg gat gtg aat acc cgc agt cgc gtg gag aat ttc cga     1008
Asp Gly Arg Leu Asp Val Asn Thr Arg Ser Arg Val Glu Asn Phe Arg
                325                 330                 335 ctg cga caa gcg gct gag cag gag cgt cag gca tcc aag cgg ctc gga     1056
Leu Arg Gln Ala Ala Glu Gln Glu Arg Gln Ala Ser Lys Arg Leu Gly
            340                 345                 350 acg aaa ctc ttt gaa caa tcc ctt ctg gct gaa gaa ccg gtc cca gca     1104
Thr Lys Leu Phe Glu Gln Ser Leu Leu Ala Glu Glu Pro Val Pro Ala
        355                 360                 365 aag tag                                                              1110
Lys

<210> SEQ ID NO 53
<211> LENGTH: 369
<212> TYPE: PRT
<213> ORGANISM: Acidovorax facilis 72W

<400> SEQUENCE: 53

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
```

```
                    35                  40                  45
Val Phe Ile Pro Gly Tyr Pro Tyr Trp Ala Trp Leu Gly Asp Val Lys
 50                  55                  60

Tyr Ser Leu Ser Phe Thr Ser Arg Tyr His Glu Asn Ser Leu Glu Leu
 65                  70                  75                  80

Gly Asp Asp Arg Met Arg Arg Leu Gln Leu Ala Ala Arg Arg Asn Lys
                 85                  90                  95

Ile Ala Leu Val Met Gly Tyr Ser Glu Arg Glu Ala Gly Ser Arg Tyr
                100                 105                 110

Leu Ser Gln Val Phe Ile Asp Glu Arg Gly Glu Ile Val Ala Asn Arg
                115                 120                 125

Arg Lys Leu Lys Pro Thr His Val Glu Arg Thr Ile Tyr Gly Glu Gly
            130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                165                 170                 175

Tyr Ser Leu Gly Glu Gln Val His Val Ala Ser Trp Pro Ala Met Ser
                180                 185                 190

Pro Leu Gln Pro Asp Val Phe Gln Leu Ser Ile Glu Ala Asn Ala Thr
                195                 200                 205

Val Ala Arg Ser Tyr Ala Ile Glu Gly Gln Thr Phe Val Leu Cys Ser
            210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
                260                 265                 270

Gly Ile Leu Tyr Ala Glu Ile Asp Leu Glu Gln Ile Leu Leu Ala Lys
                275                 280                 285

Ala Gly Ala Asp Pro Val Gly His Tyr Ser Arg Pro Asp Val Leu Ser
            290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
                340                 345                 350

Thr Lys Leu Phe Glu Gln Ser Leu Leu Ala Glu Glu Pro Val Pro Ala
            355                 360                 365

Lys

<210> SEQ ID NO 54
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 54 atg gtt tcg tat aac agc aag ttc ctc gcg gca acc gtt cag gca gag    48
Met Val Ser Tyr Asn Ser Lys Phe Leu Ala Ala Thr Val Gln Ala Glu
  1               5                  10                  15
```

```
ccg gta tgg ctc gac gca gac gca acg atc gac aag tcg atc ggc atc         96
Pro Val Trp Leu Asp Ala Asp Ala Thr Ile Asp Lys Ser Ile Gly Ile
         20                  25                  30 atc gaa gaa gct gcc caa aag ggc gcg agt ctg atc gct ttc ccg gaa        144
Ile Glu Glu Ala Ala Gln Lys Gly Ala Ser Leu Ile Ala Phe Pro Glu
             35                  40                  45 gta ttc att ccg ggc tac ccc tat tgg gcg tgg ctc ggc gac gtg aag        192
Val Phe Ile Pro Gly Tyr Pro Tyr Trp Ala Trp Leu Gly Asp Val Lys
 50                  55                  60 tac agc cta agc ttt act tca cgc tat cac gag aat tcg ttg gag cta        240
Tyr Ser Leu Ser Phe Thr Ser Arg Tyr His Glu Asn Ser Leu Glu Leu
 65                  70                  75                  80 ggt gac gac cgt atg cgt cgc ctc cag ctg gcc gcg cgc cgc aac aaa        288
Gly Asp Asp Arg Met Arg Arg Leu Gln Leu Ala Ala Arg Arg Asn Lys
                 85                  90                  95 atc gca ctc gtc atg ggc tat tcg gag cgg gaa gcc gga tcg cgc tat        336
Ile Ala Leu Val Met Gly Tyr Ser Glu Arg Glu Ala Gly Ser Arg Tyr
             100                 105                 110 ctg agc cag gtg ttc atc gac gag cgt ggc gag atc gtt gcc aat cgg        384
Leu Ser Gln Val Phe Ile Asp Glu Arg Gly Glu Ile Val Ala Asn Arg
         115                 120                 125 cgc aag ctg aag ccc aca cac gtt gag cgt acg atc tac ggc gaa ggc        432
Arg Lys Leu Lys Pro Thr His Val Glu Arg Thr Ile Tyr Gly Glu Gly
     130                 135                 140 aac gga acc gat ttc ctc acg cac gac ttc gcg ttc gga cgc gtc ggt        480
Asn Gly Thr Asp Phe Leu Thr His Asp Phe Ala Phe Gly Arg Val Gly
145                 150                 155                 160 gga ttg aac tgc tgg gaa cat ttc caa ccg ctc agc aag ttc atg atg        528
Gly Leu Asn Cys Trp Glu His Phe Gln Pro Leu Ser Lys Phe Met Met
                 165                 170                 175 tac agc ctc ggt gag cag gtc cac gtt gca tcg tgg ccg gcg atg tcc        576
Tyr Ser Leu Gly Glu Gln Val His Val Ala Ser Trp Pro Ala Met Ser
             180                 185                 190 cct ctt cag ccg gat gtt ttc caa ctg agc atc gaa gcc aac gcg acg        624
Pro Leu Gln Pro Asp Val Phe Gln Leu Ser Ile Glu Ala Asn Ala Thr
         195                 200                 205 gtc tgc cgc tcg tac gca atc gaa ggc caa acc ttt gtg ctt tgc tcg        672
Val Cys Arg Ser Tyr Ala Ile Glu Gly Gln Thr Phe Val Leu Cys Ser
     210                 215                 220 acg cag gtg atc gga cct agc gcg atc gaa acg ttc tgc ctc aac gac        720
Thr Gln Val Ile Gly Pro Ser Ala Ile Glu Thr Phe Cys Leu Asn Asp
225                 230                 235                 240 gaa cag cgc gca ctg ttg ccg caa gga tgt ggc tgg gcg cgc att tac        768
Glu Gln Arg Ala Leu Leu Pro Gln Gly Cys Gly Trp Ala Arg Ile Tyr
                 245                 250                 255 ggc ccg gat gga agc gag ctt gcg aag cct ctg gcg gaa gat gct gag        816
Gly Pro Asp Gly Ser Glu Leu Ala Lys Pro Leu Ala Glu Asp Ala Glu
             260                 265                 270 ggg atc ttg tac gca gag atc gat ctg gag cag att ctg ctg gcg aag        864
Gly Ile Leu Tyr Ala Glu Ile Asp Leu Glu Gln Ile Leu Leu Ala Lys
         275                 280                 285 gct gga gcc gat ccg gtc ggg cac tat tcg cgg cct gac gtg ctg tcg        912
Ala Gly Ala Asp Pro Val Gly His Tyr Ser Arg Pro Asp Val Leu Ser
     290                 295                 300 gtc cag ttc gac ccg cgc aat cat acg cca gtt cat cgc atc ggc att        960
Val Gln Phe Asp Pro Arg Asn His Thr Pro Val His Arg Ile Gly Ile
305                 310                 315                 320 gac ggt cgc ttg gat gtg aat acc cgc agt cgc gtg gag aat ttc cga       1008
Asp Gly Arg Leu Asp Val Asn Thr Arg Ser Arg Val Glu Asn Phe Arg
                 325                 330                 335
```

```
ctg cga caa gcg gct gag cag gag cgt cag gca tcc aag cgg ctc gga      1056
Leu Arg Gln Ala Ala Glu Gln Glu Arg Gln Ala Ser Lys Arg Leu Gly
        340                 345                 350 acg aaa ctc ttt gaa caa tcc ctt ctg gct gaa gaa ccg gtc cca gca      1104
Thr Lys Leu Phe Glu Gln Ser Leu Leu Ala Glu Glu Pro Val Pro Ala
            355                 360                 365 aag tag                                                              1110
Lys

<210> SEQ ID NO 55
<211> LENGTH: 369
<212> TYPE: PRT
<213> ORGANISM: Acidovorax facilis 72W

<400> SEQUENCE: 55

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Leu Ser Ile Glu Ala Asn Ala Thr
        195                 200                 205

Val Cys Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
    290                 295                 300

Val Gln Phe Asp Pro Arg Asn His Thr Pro Val His Arg Ile Gly Ile
305                 310                 315                 320
```

```
Asp Gly Arg Leu Asp Val Asn Thr Arg Ser Arg Val Glu Asn Phe Arg
            325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Pro Val Pro Ala
        355                 360                 365

Lys

<210> SEQ ID NO 56
<211> LENGTH: 1110
<212> TYPE: DNA
<213> ORGANISM: Escherichia coli SS1001
<220> FEATURE:
<221> NAME/KEY: CDS
<222> LOCATION: (1)..(1110)

<400> SEQUENCE: 56 atg gtt tcg tat aac agc aag ttc ctc gcg gca acc gtt cag gca gag      48
Met Val Ser Tyr Asn Ser Lys Phe Leu Ala Ala Thr Val Gln Ala Glu
1               5                   10                  15 ccg gta tgg ctc gac gca gac gca acg atc gac aag tcg atc ggc atc      96
Pro Val Trp Leu Asp Ala Asp Ala Thr Ile Asp Lys Ser Ile Gly Ile
            20                  25                  30 atc gaa gaa gct gcc caa aag ggc gcg agt ctg atc gct ttc ccg gaa     144
Ile Glu Glu Ala Ala Gln Lys Gly Ala Ser Leu Ile Ala Phe Pro Glu
        35                  40                  45 gta ttc att ccg ggc tac ccc tat tgg gcg tgg ctc ggc gac gtg aag     192
Val Phe Ile Pro Gly Tyr Pro Tyr Trp Ala Trp Leu Gly Asp Val Lys
    50                  55                  60 tac agc cta agc ttt act tca cgc tat cac gag aat tcg ttg gag cta     240
Tyr Ser Leu Ser Phe Thr Ser Arg Tyr His Glu Asn Ser Leu Glu Leu
65                  70                  75                  80 ggt gac gac cgt atg cgt cgc ctc cag ctg gcc gcg cgc cgc aac aaa     288
Gly Asp Asp Arg Met Arg Arg Leu Gln Leu Ala Ala Arg Arg Asn Lys
                85                  90                  95 atc gca ctc gtc atg ggc tat tcg gag cgg gaa gcc gga tcg cgc tat     336
Ile Ala Leu Val Met Gly Tyr Ser Glu Arg Glu Ala Gly Ser Arg Tyr
            100                 105                 110 ctg agc cag gtg ttc atc gac gag cgt ggc gag atc gtt gcc aat cgg     384
Leu Ser Gln Val Phe Ile Asp Glu Arg Gly Glu Ile Val Ala Asn Arg
        115                 120                 125 cgc aag ctg aag ccc aca cac gtt gag cgt acg atc tac ggc gaa ggc     432
Arg Lys Leu Lys Pro Thr His Val Glu Arg Thr Ile Tyr Gly Glu Gly
    130                 135                 140 aac gga acc gat ttc ctc acg cac gac ttc gcg ttc gga cgc gtc ggt     480
Asn Gly Thr Asp Phe Leu Thr His Asp Phe Ala Phe Gly Arg Val Gly
145                 150                 155                 160 gga ttg aac tgc tgg gaa cat ttc caa ccg ctc agc aag ttc atg atg     528
Gly Leu Asn Cys Trp Glu His Phe Gln Pro Leu Ser Lys Phe Met Met
                165                 170                 175 tac agc ctc ggt gag cag gtc cac gtt gca tcg tgg ccg gcg atg tcc     576
Tyr Ser Leu Gly Glu Gln Val His Val Ala Ser Trp Pro Ala Met Ser
            180                 185                 190 cct ctt cag ccg gat gtt ttc caa ctg agc atc gaa gcc aac gcg acg     624
Pro Leu Gln Pro Asp Val Phe Gln Leu Ser Ile Glu Ala Asn Ala Thr
        195                 200                 205 gtc acc cgc tcg tac gca atc gaa ggc caa acc ttt gtg ctt tgc tcg     672
Val Thr Arg Ser Tyr Ala Ile Glu Gly Gln Thr Phe Val Leu Cys Ser
    210                 215                 220
```

-continued

```
acg cag gtg atc gga cct agc gcg atc gaa acg ttc tgc ctc aac gac      720
Thr Gln Val Ile Gly Pro Ser Ala Ile Glu Thr Phe Cys Leu Asn Asp
225                 230                 235                 240 gaa cag cgc gca ctg ttg ccg caa gga tgt ggc tgg gcg cgc att tac      768
Glu Gln Arg Ala Leu Leu Pro Gln Gly Cys Gly Trp Ala Arg Ile Tyr
            245                 250                 255 ggc ccg gat gga agc gag ctt gcg aag cct ctg gcg gaa gat gct gag      816
Gly Pro Asp Gly Ser Glu Leu Ala Lys Pro Leu Ala Glu Asp Ala Glu
        260                 265                 270 ggg atc ttg tac gca gag atc gat ctg gag cag att ctg ctg gcg aag      864
Gly Ile Leu Tyr Ala Glu Ile Asp Leu Glu Gln Ile Leu Leu Ala Lys
    275                 280                 285 gct gga gcc gat ccg gtc ggg cac tat tcg cgg cct gac gtg ctg tcg      912
Ala Gly Ala Asp Pro Val Gly His Tyr Ser Arg Pro Asp Val Leu Ser
290                 295                 300 gtc cag ttc gac ccg cgc aat cat acg cca gtt cat cgc atc ggc att      960
Val Gln Phe Asp Pro Arg Asn His Thr Pro Val His Arg Ile Gly Ile
305                 310                 315                 320 gac ggt cgc ttg gat gtg aat acc cgc agt cgc gtg gag aat ttc cga     1008
Asp Gly Arg Leu Asp Val Asn Thr Arg Ser Arg Val Glu Asn Phe Arg
            325                 330                 335 ctg cga caa gcg gct gag cag gag cgt cag gca tcc aag cgg ctc gga     1056
Leu Arg Gln Ala Ala Glu Gln Glu Arg Gln Ala Ser Lys Arg Leu Gly
        340                 345                 350 acg aaa ctc ttt gaa caa tcc ctt ctg gct gaa gaa ccg gtc tca gca     1104
Thr Lys Leu Phe Glu Gln Ser Leu Leu Ala Glu Glu Pro Val Ser Ala
    355                 360                 365 aag tag                                                            1110
Lys
```

<210> SEQ ID NO 57
<211> LENGTH: 369
<212> TYPE: PRT
<213> ORGANISM: Escherichia coli SS1001

<400> SEQUENCE: 57

```
Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                165                 170                 175
```

-continued

```
Tyr Ser Leu Gly Glu Gln Val His Val Ala Ser Trp Pro Ala Met Ser
            180                 185                 190

Pro Leu Gln Pro Asp Val Phe Gln Leu Ser Ile Glu Ala Asn Ala Thr
        195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
            275                 280                 285

Ala Gly Ala Asp Pro Val Gly His Tyr Ser Arg Pro Asp Val Leu Ser
    290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Glu Pro Val Ser Ala
            355                 360                 365

Lys
```